(12) United States Patent
Ott

(10) Patent No.: US 8,217,084 B2
(45) Date of Patent: *Jul. 10, 2012

(54) MEDICINAL PRODUCTS INCORPORATING BOUND ORGANOSULFUR GROUPS

(75) Inventor: David M. Ott, Oakland, CA (US)

(73) Assignee: Allium Vitalis Incorporated, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/137,747

(22) Filed: May 24, 2005

(65) Prior Publication Data

US 2005/0260250 A1    Nov. 24, 2005

Related U.S. Application Data

(60) Provisional application No. 60/574,374, filed on May 24, 2004.

(51) Int. Cl.
  *A23L 1/30* (2006.01)
  *A61K 31/10* (2006.01)
  *A61K 38/02* (2006.01)

(52) U.S. Cl. ......... 514/706; 514/707; 514/1.1; 424/439; 426/547; 426/648

(58) Field of Classification Search .................. 424/489, 424/465, 456, 754
  See application file for complete search history.

(56) References Cited

U.S. PATENT DOCUMENTS

| | | | | |
|---|---|---|---|---|
| 3,615,597 | A * | 10/1971 | Durst et al. ................... | 426/650 |
| 5,451,412 | A | 9/1995 | Bounous et al. | |
| 6,159,500 | A * | 12/2000 | Demopoulos et al. ........ | 424/456 |
| 6,270,803 | B1 * | 8/2001 | Blatt et al. ..................... | 424/489 |
| 2003/0068372 | A1 * | 4/2003 | Kirschner et al. ............ | 424/465 |
| 2004/0170707 | A1 * | 9/2004 | Kannar ......................... | 424/754 |

FOREIGN PATENT DOCUMENTS

WO    WO 01/36450 A1    5/2001

OTHER PUBLICATIONS

Garlic and Onion Burger recipe. <www.allrecipes.com>.*
Yeh, Y-Y., et al. 2001 The Journal of Nutrition supplement: 989S-993S.*
O'Hara, MA., et al. 1998 Arch Fam Med 7: 523-536.*
Ali, M., et al. 2000 Prostaglandins, Leukotrienes and Essential Fatty Acids 62(2): 55-73.*
Morioka, N., et al. 1993 Cancer Immunol Immunother 37: 316-322.*
Lawson, "Garlic: A Review of Its Medicinal Effects and Indicated Active Compounds", in "Phytomedicines of Europe—Chemistry and Biological Activity", 1998; American Chemical Society, Washington, DC.
White et al., "Toxicity evaluations of L-cysteine and Procysteine, a cysteine prodrug, given once intravenously to neonatal rats", Toxicol Lett. 1993;69(1):15-24.
Ludescher, "Physical and Chemical Properties of Amino Acids and Proteins", in "Food Proteins—Properties and Characterization", 1996; VCH Publishers, Inc. New York, NY.
Friedman, "Nutrition", in "Physical and Chemical Properties of Amino Acids and Proteins", in "Food Proteins—Properties and Characterization", 1996; VCH Publishers, Inc. New York, NY.
Cayot et al., "Structure-Function Relationships of Whey Proteins", in "Food Proteins and Their Applications", 1997; Marcel Dekker, Inc., New York, NY.
Orringer et al., "An ascorbate-mediated transmembrane-reducing system of the human erythrocyte", J Clin Invest. 1979;63(1):53-8.
Wierzbicka et al., "Glutatione in Food", J Food Compost Anal. 1989;2:327-337.
Kyung et at., "Antimicrobial activity of sulfur compounds derived from cabbage", J Food Prot. 1997;60(1):67-71.
Barnhart et al., "Concentration-dependent antioxidant activity of probucol in low density lipoproteins in vitro: probucol degradation precedes lipoprotein oxidation", J Lipid Res. 1989;30(11):1703-10.
Friedman et al., "Nutritional improvement of soy flour", J Nutr. 1984;114(12):2241-6.
Amagase et al., "Intake of garlic and its bioactive components", J Nutr. 2001;131(3s):955S-62S.
Lau, "Suppression of LDL oxidation by garlic", J Nutr. 2001;131(3s):985S-8S.
Borek, "Antioxidant health effects of aged garlic extract", J Nutr. 2001;131(3s):1010S-5S.
Lamm et al., "Enhanced immunocompetence by garlic: role in bladder cancer and other malignancies", J Nutr. 2001;131(3s):1067S-70S.
Hoshino et al., "Effects of garlic preparations on the gastrointestinal mucosa", J Nutr. 2001;131(3s):11095-13S.
Luo et al,. "Kinetics and mechanism of the reaction of cysteine and hydrogen peroxide in aqueous solution", J Pharm Sci. 2005;94(2):304-16.
Prasad et al., "Antioxidant activity of allicin, an active principle in garlic", Mol Cell Biochem. 1995;148(2):183-.
Miron et al., "Inhibition of tumor growth by a novel approach: in situ allicin generation using targeted alliinase delivery", Mol Cancer Ther. 2003;2(12):1295-301.
Ankri et al., "Antimicrobial properties of allicin from garlic", Microbes Infect. 1999;1(2):125-9.
Hamm et al., "Changes in the sulphydryl and disulphide groups in beef muscle proteins during heating", Nature. 1965;207(3):1269-71.
Reicks et al., "Modulation of rat hepatic cytochrome P-450 activity by garlic organosulfur compounds", Nutr Cancer. 1996;25(3):241-8.
Munday et al., Low doses of diallyl disulfide, a compound derived from garlic, increase tissue activities of quinone reductase and glutathione transferase in the gastrointestinal tract of the rat, Nutr Cancer. 1999;34(1):42-8.

(Continued)

Primary Examiner — Marsha Tsay

(57) ABSTRACT

Nutraceutical and dietary supplement formulations for delivering bioavailable thiols to a host, comprising certain organosulfur radicals, such as the allyl mercapto radical, bound to larger molecules such as proteins, resulting in the formation in the host's body of various *allium*-related compounds such as allicin. The formulations are produced by treating an ingestible material comprising a cysteine-containing protein with a thiol, disulfide, mixed disulfide, thiosufinate or mixed thiosulfinate so as to cause thiol residues to become disulfide bonded to cysteines contained in the protein.

12 Claims, 9 Drawing Sheets

OTHER PUBLICATIONS

Chance et al., "Hydroperoxide metabolism in mammalian organs", Physiol Rev. 1979;59(3):527-605.

Nakagawa et al., "Prevention of Liver Damage by Aged Garlic Extract and Its Components in Mice", Phytother Res. 1989;53:50-53.

Banerjee et al., "Garlic as an antioxidant: the good, the bad and the ugly", Phytother Res. 2003;17(2):97-106.

Mukherjee et al., "Prevention of bone loss by oil extract of garlic (*Allium sativum* Linn.) in an ovariectomized rat model of osteoporosis", Phytother Res. 2004 May;18(5):389-94.

Schuessler et al., "Cardiac Effects of Flavonoids from *Crataegus* Species", Planta Med. 1993;59:A668.

Imai et al., "Antioxidant and radical scavenging effects of aged garlic extract and its constituents, Planta Med", 1994;60(5):417-20.

Lawson et al., "Allicin release under simulated gastrointestinal conditions from garlic powder tablets employed in clinical trials on serum cholesterol", Planta Med. 2001;67(1):13-8.

Hammett et al., "The Influence of Sulfhydryl and Sulfoxide on Gross Regeneration in the Hermit Crab (*Pagurus longicarpus*)", Protaplasma 1931;13:261-267.

Hammett et al., "The Growth Reaction of Embryonic Marne Forms to Sulfhydryl and SUlfoxide", Protaplasma 1932;15:59-70.

Chung et al., "The inflammation hypothesis of aging: molecular modulation by calorie restriction", Ann N Y Acad Sci. 2001;928:327-35.

Singh, "Thiol-disulfide Interchange", Chapter 13 in "Supplement S—The Chemistry of Sulphur-containing Functional Groups", 1993; John Wiley & Sons, New York, NY.

Wardman, "Thiyl Radicalas in Biology: Their Role as a 'Molecular Switch' Central to Cellular Oxidative Stress", Chapter 10 in "S-Centered Radicals", 1999; John Wiley & Sons, New York, NY.

Daune, "Proton Exchange", Section 9.3 in "Molecular Biophysics—Structures in Motion", Oxford University Press, New York, NY.

Newstrom, "Cysteine", in "Nutrients Catalog", 1993; McFarland & Company Inc., Jefferson, NC.

Huie et al., "Chemistry of Reactive Oxygen Species" in "Reactive Oxygen Species in Biological Systems: An Interdisciplinary Approach", 1999; Kluwer Academic, New York, NY.

Bach, "Cystine and Methionine as Preventive Factors of Certain Liver Diseases" in "The Metabolism of Protein Constituents in the Mammalian Body", 1952; Oxford Press, London, UK.

Petsko et al., "Control by pH and Redox Environment", Section 3-3 in "Protein Structure and Function", 2004; New Science Press Ltd., London, UK.

Torchinskii, "Oxidation of S-S Groups, Identification of Cystine-Containing Peptides", Section 2.14 in "Sulfhydryl and Disulfide Groups of Proteins", Consultants Bureau, New York, NY.

Freedman, "The Formation of Disulfide Bonds in the Synthesis of Secretory Proteins: Properties and Role of Protein Disulfide Isomerase", Chapter 13 in "Glutathione: Metabolism and Physiological Functions", 1990; CRC Press, Boca Raton, FL.

Tatishi, "Regulation of Glutathione Level in Primary Cultured Hepatocytes", Chapter 4 in "Glutathione Centennial—Molecular Perspectives and Clinical Implications", 1988; Academic Press, Inc., San Diego, CA.

Gilbert, "Thermodynamic and Kinetic Constraints on Thiol/Disulfide Exchange Involving Glutathione Redox Buffers", Chapter 5 in "Glutathione Centennial—Molecular Perspectives and Clinical Implications", 1988; Academic Press, Inc., San Diego, CA.

Bannai et al., "Regulation of Glutathione Level by Amino Acid Transport", Chapter 29 in "Glutathione Centennial—Molecular Perspectives and Clinical Implications", 1988; Academic Press, Inc., San Diego, CA.

Kim, "Intestinal Mucosal Hydrolysis of Proteins and Peptides" in "Peptide Transport and Hydrolysis, Ciba Foundation Symposium 50", 1977; Elsevier, New York, NY.

Weisger et al., "S-Methylation: Thiol S-Methyltransferase", Chapter 7 in Enzymatic Basis of Detoxification, vol. II, 1980' Academic Press New York, NY.

Ishikawa et al., Transport of Glutathione S-Conjugates from Cancer Cells: Function and Structure of the GS-X Pump, Chapter 18 in "Glutathione S-Transferases -0 Structure, Function and Clinical Implications", 1996; Taylor & Frances Ltd., London, UK.

Packer et al., "Vitamin E: An Introduction", Chapter 9 in "The Antioxidant Vitamins C and E", 2002; AOCS Press, Champaign, IL.

Calvin, "Mercaptans and Disulfides: Some Physics, Chemistry, and Speculation", in "Glutathione—Proceesings of the Symposium Held at Ridgefeld, Conneticuit Nov. 1953", 1954; Academic Press, New York, NY.

Friedman, "Prevention of Adverse Effects of Food Browning", Chapter 15 of "Nutritional and Toxicological Consequences of Food Processing", 1991; Plenum Press, New York, NY.

Sarwar et al., "Influence of Feeding Alkaline/Heat Processed Proteins on Growth and Protein and Mineral Status of Rats", Chapter 11 in "Impact of Processing on Food Safety", 1999; Kluwer Academic, New York, NY.

Guhr et al., "Role of Phytochemicals in Chronic Disease Prevention", Chapter 32 in "Nutraceuticals: Designer Foods III Garlic, Soy and Licorice", 1997; Food & Nutrition Press Inc., Trumbull, CT.

Inoue et al., "Biochemical and Clinical Aspects of Extracellular Glutathione and Related Thiols", Chapter 13 in "Biothiols in Health and Disease", 1995; Marcel Dekker, Inc., New York, NY.

Meister, "The Antioxidant Effects of Glutathione and Ascorbic Acid", in "Oxidative Stress, Cell Activation, and Viral Infection", 1994; Birkhauser Verlag, Basel Switzerland.

Droge et al., "Abnormal Redox Regulation in HIV Infection and other Immunological Diseases", in "Oxidative Stress, Cell Activation, and Viral Infection", 1994; Birkhauser Verlag, Basel Switzerland.

Feldberg et al., "In vitro mechanism of inhibition of bacterial cell growth by allicin", Antimicrob Agents Chemother. 1988;32(12):1763-8.

Tada et al., "Nematicidal and Antimicrobial Constituents from *Allium grayi* Regel and *Allium fistulosum* L. var. *caespitosum*". Agric Biol Chem. 1988;52(9):2382-2385.

Droge, "Oxidative stress and aging", Adv Exp Med Biol. 2003;543:191-200.

Josling, "Preventing the Common Cold With a Garlic Supplement: A Double-Blind, Placebo-Controlled Study", Advances in Therapy. 2001;18(4):189-193.

Di Buno et al., Total sulfur amino acid requirement in young men as determined by indicator amino acid oxidation with L-[1-13C]phenylalanine, Am J Clin Nutr. 2001;74(6):756-60.

Elkayam, et al., "The effects of allicin on weight in fructose-induced hyperinsulinemic, hyperlipidemic, hypertensive rats", Am J Hypertens. 2003;16(12):1053-6.

Elkayam, et al., "The effects of allicin and enalapril in fructose-induced hyperinsulinemic hyperlipidemic hypertensive rats", Am J Hypertens. 2001;14(4 Pt 1):377-81.

Droge, et al. "Modulation of lymphocyte functions and immune responses by cysteine and cysteine derivatives", Am J Med. 1991;91(3C):140S-144S.

Johnson et al., "Death of *Salmonella typhimurium* and *Escherichia coli* in the presence of freshly reconstituted dehydrated garlic and onion", Appl Microbiol. 1969;17(6):903-5.

"Taurine—monograph", Altern Med Rev. 2001;6(1):78-82.

Barkholt et al., "Amino acid analysis: determination of cysteine plus half-cystine in proteins after hydrochloric acid hydrolysis with a disulfide compound as additive", Anal Biochem. 1989;177(2):318-22.

Meister et al., "Glutathione", Annu Rev Biochem. 1983;52:711-60.

Droge, "The plasma redox state and ageing", Ageing Res Rev. 2002;1(2):257-78.

Bremer et al., "Enzymatic Methylation of Foreign Sulfhydryl Compounds", Biochem Biophys Acta. 1961;46:217-224.

Napolitano et al., "2-Aryl-1,3-thiazolidines as masked sulfhydryl agents for inhibition of melanogenesis", Biochim Biophys Acta. 1991;1073(2):416-22.

Rabinkov et al., "The mode of action of allicin: trapping of radicals and interaction with thiol containing proteins" Biochim Biophys Acta. 1998;1379(2):233-44.

Rabinkov et al., "The mode of action of allicin: its ready permeability through phospholipid membranes may contribute to its biological activity", Biochim Biophys Acta. 2000;1463(1):20-30.

Seo et al., "Antibacterial Activity of S-Methyl Methanethiosulfinate and S-Methyl 2-Propene-1-thiosulfinate from Chinese Chive toward *Escherichia coli* O157:H7", Biosci Biotechnol Biochem. 2001;65(4):966-968.

Cotgreave et al., "Recent trends in glutathione biochemistry—glutathione-protein interactions: a molecular link between oxidative stress and cell proliferation?", Biochem Biophys Res Commun. 1998;242(1):1-9.

Saxena et al., "Formation of three-dimensional structure in proteins. I. Rapid nonenzymic reactivation of reduced lysozyme", Biochemistry. 1970;9(25):5015-23.

Wills, "Enzyme Inhibition by Allicin, the Active Principle of Garlic", Biochem J. 1956;63:514-520.

Crawhall et al., "The intracellular ratio of cysteine and cystine in various tissues", Biochem J. 1967;105(2):891-6.

Patarasakulchai et al., "Se-Aryl selenenylthiosulphates and S-aryl sulphenylthiosulphates as thiol-blocking reagents", Biochem J. 1984;221(3):797-801.

Gyamlani et al., "Acetaminophen toxicity: suicidal vs. accidental", Crit Care. 2002;6(2):155-9.

Das et al., "Nitric oxide synthase activation is a unique mechanism of garlic action", Biochem Soc Trans. 1995;23(1):136S.

Bahlis et al., "Feasibility and correlates of arsenic trioxide combined with ascorbic acid-mediated depletion of intracellular glutathione for the treatment of relapsed/refractory multiple myeloma", Clin Cancer Res. 2002;8 (12):3658-68.

Shirin et al., "Antiproliferative effects of S-allylmercaptocysteine on colon cancer cells when tested alone or in combination with sulindac sulfide", Cancer Res. 2001;61(2):725-31.

Teyssier et al., "Metabolism of diallyl disulfide by human liver microsomal cytochromes P-450 and flavin-containing monooxygenases", Drug Metab Dispos. 1999;27(7):835-41.

Delany et al., "The Delany Sisters' Book of Everyday Wisdom", 1994; Kodansha International New York, NY.

Mitra et al., "Nutritional Factors and Susceptibility to Arsenic-Caused Skin Lesions in West Bengal, India", Environ Health Perspect. 2004;112(10)1104-1109.

Jocelyn, "The standard redox potential of cysteine-cystine from the thiol-disulphide exchange reaction with glutathione and lipoic acid", Eur J Biochem. 1967;2(3):327-31.

Reuter et al., "*Allium sativum* and *Allium ursinum*: Chemistry, Pharmacology and Medicinal Applications" Econimic and Medicinal Plant Research. 1994;6:55-113.

Breu et al., "*Allium cepa* L. (Onion): Chemistry, Analysis and Pharmacology" Econimic and Medicinal Plant. Research. 1994;6:115-147.

Stoewsand, "Bioactive organosulfur phytochemicals in *Brassica oleracea* vegetables—a review", Food Chem Toxicol. 1995;33(6):537-43.

Focke et al., "Allicin, a naturally occurring antibiotic from garlic, specifically inhibits acetyl-CoA synthetase", FEBS Lett. 1990;261(1):106-8.

Shashikanth et al., "A comparative study of raw garlic extract and tetracycline on caecal microflora and serum proteins of albino rats", Folia Microbiol (Praha). 1984;29(4):348-52.

Mendiratta et al., "Erythrocyte ascorbate recycling: antioxidant effects in blood", Free Radic Biol Med. 1998;24(5):789-97.

Sharma et al., "Antibacterial property of *Allium sativum* Linn.: in vivo & in vitro studies", Indian J Exp Biol. 1977;15(6):466-8.

Augusti, "Therapeutic values of onion (*Allium cepa* L.) and garlic (*Allium sativum* L.)", Indian J Exp Biol. 1996;34(7):634-40.

Fuchin et al., "Ginger, Garlic & Green Onion as Medicine" Chapter 2 (pp. 15-86), 1998; Pelanduk Publications, Malaysia.

Cavallito et al., "Allicin, the Antibacterial Principle of *Allium sativum*. I. Isolation, Physical Properties and Antibacterial Action", J Am Chem Soc. 1944;66:1950-1951.

Cavallito et al., "Allicin, the Antibacterial Principle of *Allium sativum*. II. Determination of the Chemical Structure", J Am Chem Soc. 1944;66:1952-1954.

Small et al., "Alkyl Thiosulfinates", J Am Chem Soc. 1947;69:1710-1713.

Block et al., "The Chemistry of Alkyl Thiosulfinate Esters. VII. Mechanistic Studies and Synthetic Applications", J Am Chem Soc. 1974;96:3929-3944.

Wall et al., "Protein in Varietally Derived Apple Juice", J Agric Food Chem. 1996;44:3413-3415.

Cao et al., "Antioxidant Capacity of Tea and Common Vegetables", J Agric Food Chem. 1996;44:3426-3431.

Lawson et al., "Low allicin release from garlic supplements: a major problem due to the sensitivities of alliinase activity", J Agric Food Chem. 2001;49(5):2592-9.

Xiao et al., "Antioxidant functions of selected allium thiosulfinates and S-alk(en)yl-L-cysteine sulfoxides", J Agric Food Chem. 2002;50(9):2488-93.

Negishi et al., "Effects of food materials on removal of Allium-specific volatile sulfur compounds", J Agric Food Chem. 2002;50(13):3856-61.

Lawson et al., "Allicin and allicin-derived garlic compounds increase breath acetone through allyl methyl sulfide: use in measuring allicin bioavailability", J Agric Food Chem. 2005;53(6):1974-83.

\* cited by examiner

MEDICINAL PRODUCTS INCORPORATING BOUND ORGANOSULFUR GROUPS

This application claims the benefit of provisional application No. 60/574,374 filed May 24, 2004.

1. BACKGROUND OF THE INVENTION

1.1 Field of the Invention

The present invention relates generally to the maintenance of good health through the consumption of *allium*-related medicinal products.

2. DEFINITIONS, ORGANOSULFUR GLOSSARY, AND ABBREVIATIONS

Allicin: Chemical name DiAllylThioSulfinate; chemical formula:

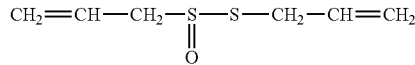

A compound formed by crushing garlic (which allows the enzymatic conversion by alliinase of alliin to allicin) that produces many of the medicinal benefits that are attributed to garlic. For the exposition of the present invention, allicin is used as a model compound representative of a larger class of thiosulfinate compounds set out below. (Other thiosulfinates share the general formula RS(O)SR', with the R and R' groups of the particular compound substituting for the allyl groups of allicin). In general, a compound is referred to herein as a "model" compound when it is representative of a more general class of compounds defined herein.

*Allium*-related compounds: Organosulfur compounds that are either derived from an *allium* (e.g. garlic or onion) through chemical or metabolic means, or are related to such compounds in specific ways such that they can reasonably be expected to exhibit similar medicinal properties. In a historical context, these compounds have been associated with alliums. In the context of this invention, this term is used to refer to the general class of compounds containing one or more organosulfur groups that can metabolize to thiols and thiosulfinates or mixed thiosulfinates.

Allyl mercaptan: AllylSH, chemical name AllylThiol; chemical formula:

$$CH_2=CH-CH_2-SH$$

The primary pre-hepatic metabolite of allicin, diallyl disulfide, SAMC, and various other *allium* related compounds containing thioallyl groups. Within a red blood cell (RBC), an allicin molecule will metabolize quickly into two allyl mercaptan molecules. In the present exposition allyl mercaptan is the model thiol compound.

AllylMercapto radical: AllylS*, allyl mercaptan without the terminal hydrogen atom of the SH group, resulting in an unpaired electron on the sulfur atom which is available for covalent bonding to the remainder of a larger molecule. Also called a thioallyl group.

$$CH_2=CH-CH_2-S*$$

Cysteine: CySH, a sulfur containing amino acid with the formula:

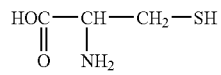

Cysteinyl radical: CyS*, cysteine without the terminal hydrogen atom of the SH group, resulting in an unpaired electron on the sulfur atom. A cysteinyl radical will typically be covalently bonded to another atom that is part of the larger molecule (e.g. with the sulfur atom of an AllylMercapto radical to form an S-AllylMercaptoCysteine molecule).

Cystine: CySSCy, cysteine disulfide. The most common form of oxidized cysteine. The term cyst(e)ine is used herein to refer to cysteine or to cystine or to any combination of cysteine and cystine. The particular meaning will be clear from the context.

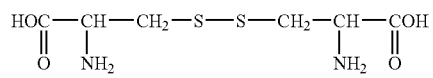

Diallyl Disulfide: DADS, (also abbreviated as AllylSSAllyl or ASSA), the disulfide formed from two AllylMercapto radicals bonded together. Equivalent to deoxygenated allicin. In the present exposition diallyl disulfide is the model disulfide compound.

$$CH_2=CH-CH_2-S-S-CH_2-CH=CH_2$$

Diallyl Trisulfide: DATS, (also abbreviated as AllylSSSAllyl or ASSSA), the trisulfide formed from two AllylMercapto radicals bonded to a sulfur atom.

$$CH_2=CH-CH_2-S-S-S-CH_2-CH=CH_2$$

Free radical: R*, a group of atoms with an unpaired electron. Free radicals are typically very reactive, with a tendency to either capture an electron, to donate an electron, or to covalently bond with other atoms to form a larger molecule.

Glutathione: A tripeptide composed of the amino acids glutamic acid, cysteine, and glycine. Glutathione is present in biological systems in a variety of forms, the most important of which are reduced glutathione (GSH), the anion of reduced glutathione (GS⁻), the glutathiyl free radical (GS*), glutathione disulfide (GSSG), mixed glutathione disulfides (GSSR), and protein-glutathione mixed disulfides (PSSG). The term "glutathione" by itself refers to all of the above, although others sometimes use it to refer to GSH only (presumably because GSH is the predominant form of glutathione within normal cells). The term "oxidized glutathione" usually refers to GSSG (the typical end product of oxidation, even when GS* is the initial oxidation product).

Mercaptan: A small molecule that contains an exposed "SH" group. Mercaptans are thiols that are typically volatile and very smelly.

Oxidation: The removal of an electron (or a hydrogen atom) from an atom or a molecule. Oxidation can also refer to any transformation that tends to occur when something is exposed to reactive oxygen (e.g. the formation of rust), without necessarily specifying the reaction mechanism.

Oxidized: The reaction product that tends to be produced when the reactants are exposed to reactive oxygen, such as the conversion of thiols to disulfides, typically due to the removal of electrons (or hydrogen atoms). For example, if two cysteine molecules together in solution are exposed to oxygen, they tend to eventually form a cysteine disulfide molecule (cystine).

Oxygenated: Another form of oxidation product, where an oxygen atom has been added to a molecule.

Reactive Oxygen Species: ROS, oxygen containing molecules that are capable of producing oxidative damage to other molecules. Many, but not all, ROS are free radicals. Examples include (QP535.O1R43:33):

$H_2O_2$ (hydrogen peroxide), $*O_2^-$ (superoxide radical), $*OH$ (hydroxyl radical), $HOCl$ (hypoclorus acid), $ONOO^-$ (peroxynitrite), $O_2^1$ (singlet oxygen), $O_3$ (ozone), $*NO$ (nitric oxide), and $*NO_2$ (nitrogen dioxide).

Reduced: The converse of oxidized. When a thiyl radical is covalently bonded to a hydrogen atom, it is said to be in its "reduced state". For example, when the terminal sulfur of a cystienal radical is bonded to a hydrogen atom to form a cysteine molecule, it is in its reduced state.

SAMC: S-AllylMercaptoCysteine (also shown as AllylSSCy), the molecule formed by a Cysteinyl radical disulfide bonded to an AllylMercapto radical. In the present exposition SAMC is the model mixed disulfide molecule.

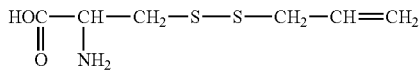

SAMG: S-AllylMercaptoGlutathione (also shown as AllylSSG), the molecule formed by a glutathione radical disulfide bonded to an AllylMercapto radical.

Thiol: RSH, Any molecule that includes one or more terminal sulfhydrate (SH) group.

3. REFERENCES

For articles contained in books, the first listing (typically by Dewey decimal number or ISBN number) contains retrieval information for the book and the actual reference(s) are the listings for the article(s) or pages that follow.

AAC32:1763; R. Feldberg et al; In Vitro Mechanism of Inhibition of Bacterial Cell Growth by Allicin; Antimicrobial Agents and Chemotherapy 32:1763.

ABC52:2383; M. Tada et al; Nematicidal and Antimicrobial Constituents from *Allium grayi* Regel and *Allium fistulosum* L. var. *caespiitosum*; Agricultural and Biological Chemistry 52:2383.

AEMB543:191; W. Droge; Oxidative Stress and Aging; Advances in Experimental and Medical Biology 543:191.

AIT18:189; P. Josling; Preventing the Common Cold With a Garlic Supplement: A Double-Blind, Placebo-Controlled Survey; Advances In Therapy 18:189.

AJM91:3C-140S; W. Droge et al. Modulation of Lymphocyte Functions and Immune Response by Cysteine and Cysteine Derivatives; The American Journal of Medicine 91:3C-140S.

AJCN74:756; M. Buono et at; Total Sulfur Amino Acid Requirement in Young Men as Determined by Indicator Amino Acid Oxidation; American Journal of Clinical Nutrition 74:756.

AJH14:377; A. Elkayam et al; The Effects of Allicin and Enapril in Fructose-Induced Hyperinsulinemic Hyperlippidemic Hypertensive Rats; The American Journal of Hypertension 14:377.

AJH16:1054; A. Elkayam et al; The Effects of Allicin on Weight in Fructose-Induced Hyperinsulinemic, Hyperlippidemic, Hypertensive Rats; The American Journal of Hypertension 16:1053.

AM17:903; M. G. Johnson and R. H. Vaughn; Death of *Salmonella typhimurium* and *Escherichia coli* in the Presence of Freshly Reconstituted Dehydrated Garlic and Onion; Applied Microbiology 17:903.

AMR6:78; Taurine; Alternative Medicine Review 0.6:78.

ANBC177:318; Amino Acid Analysis: Determination of the Cystiene plus Half-Cysteine in Proteins after Hydrolic Acid Hydrolysis with a Disulfide Compound as an Additive; Analytical Biochemistry 177:318.

ARB52:711; A. Meister and M. Anderson; Glutathione; Annual Review of Biochemistry 52:711.

ARR1:257; W. Droge; The Plasma Redox State and Ageing; Ageing Research Reviews 1:257.

BBA46:217; J. Bremer and D. Greenberg; Enzymic Methylation of Foreign Sulfhydryl Compounds; Biochimica et Biophysica Acta 46:217.

BBA1073.416; A. Napolitano et al; 2-Aryl-1,3-thiazolidines as masked sulfhydryl agents for inhibition of melanogenesis; Biochimica et Biophysica Acta 1073:416.

BBA1379:233; A. Rabinkov, et al; The mode of action of allicin: trapping of radicals and interaction with thiol containing proteins; Biochimica et Biophysica Acta 1379:233.

BBA1463:20; T. Miron, et al; The mode of action of allicin: its ready permeability through phospholipid membranes may contribute to its biological activity. Biochimica et Biophysica Acta 1463:20.

BBBIO65:966; K. Seo, et al; Antibacterial activity of S-Methyl Methanethiosulfinate and S-Methyl 2-Propene-1-thiosulfinate from Chinese Chive towards *Escherichia coli* O.0157:H7; Bioscience, Biotechnology and Biochemistry 65:966.

BBRC242:1; I. Cotgreave and R. Gerdes; Recent Trends in Glutathione Biochemistry—Glutathione-Protein Interactions: A Molecular Link between Oxidative Stress and Cell Proliferation?; Biochemical and Biophysical Research Communications 242:1.

BICH9:5105; V. Saxena and D. Wetlaufer; Formation of Three-Dimensional Structure in Proteins. I. Rapid Nonenzymic Reactivation of Reduced Lysozome; Biochemistry 9:5015.

BIJ63:514; E. D. Wills; Enzyme Inhibition by Allicin, the Active Principle of Garlic; Biochemical Journal 63:514.

BIJ105:891; J. Crawhall and S. Segal; The intracellular Ratio of Cysteine to Cystine in Various Tissues; Biochemical Journal 105:891.

BIJ221:797; N. Patarasakulchai et al; Se-Aryl selenylthiosulphates and S-aryl sulphenylthiosu; phates as thiol-blocking reagents; Biochemical Journal 221:797.

BMCCC6:155; G. G. Gyamlani et al; Acetaminophen toxicity: suicidal vs accidental; BioMed Central Critical Care 6:155.

BST23:S136; I. Das et al; Nitric Oxide Synthase is a Unique Mechanism of Garlic Action; Biochemical Society Transactions 23:S136.

CCR8:3658; N. Bahlis et al; Feasibility and Correlates of Arsenic Trioxide Combined with Ascorbic Acid-mediated Depletion of Intrecellular Glutathone for the Treatment of Relapsed/Refractory Multiple Myeloma; Clinical Cancer Research 8:3658.

CR61:725; H. Shirin et al; Antiproliferative Effects of S-Allylmercaptocysteine on Colon Cancer, Cells When Tested Alone or in Combination with Sulindac Sulfide; Cancer Research 61:725.

DMD27:835; Metabolism of Diallyl Disulfide by Human Liver Microsomal Cytochromes P-450 and Flavin-containing Monooxygenases; Drug Metabolism and Disposition 27:835.

E185.96.D368; S. and E. Delany with A. Hearth, 1994; The Delany Sisters' Book of Everyday Wisdom; Kodansha International, New York, N.Y.

E185.96.D368:107; The Order of the Day (in E185.96.D368).

EHP112:1104; S. Mitra, et al; Nutritional Factors and Susceptibility to Arsenic Caused Skin Lesions in West Bengal, India; Environmental Health Perspectives 112:1104.

EJB2:327; P. Jocelyn; The Standard Redox Potential of Cysteine-Cystine from the Thiol-Disulfide Exchange Reaction with Glutathione and Lipolic Acid; European. Journal of Biochemistry 2:327.

EMPR6:56; H. Reuter, A. Sendl; Allium sativum and Allium ursinum: Chemistry, Pharmacology and Medicinal Applications; Economic and Medicinal Plant Research 6:56.

EMPR6:115; W. Breu, W. Dorsch; Allium cepa L. (Onion): Chemistry, Analysis and Pharmacology; Economic and Medicinal Plant Research 6:115.

FCT33:537; G. Stoewsand; Bioactive Organosulfur Phytochemicals in Brassica oleracea Vegetables—A Review; Food and Chemical Toxicology 33:537.

FEBS261:106; M. Focke, et al; Allicin, a naturally occurring antibiotic from garlic, specifically inhibits acetyl-CoA synthase; FEBS Letters 261:106.

FM29:348; K. N. Silashikanth, et al; A Comparative Study of Raw Garlic Extract and Tetracycline on Caecal Microflora and Serum Proteins of Albino Rats; Folia Microbiologica 29:348.

FRBM24:789; S. Mendiratta et al; Erythrocyte Ascorbate Recycling: Antioxidant Effects in Blood; Free Radicals in Biology and Medicine 24:789.

IJEB15:466; V. Sharma et al; Antibacterial Property of Allium SativumLinn.: in vivo & in vitro Studies; Indian Journal of Experimental Biology 15:466.

IJEB34:634; K. T. Agusti; Therapeutic values of onion (Allium cepa L.) and garlic (Allium sativum L.); Indian Journal of Experimental Biology 34:634.

ISBN9679786846; W. Fuchin and D. Yuhua 1998; Ginger, Garlic & Green Onion as Medicine; Pelanduk Publications, Malaysia.

ISBN9679786846:15; Chapter 2: Medical Diseases (in ISBN9679786846).

JACS66:1950; C. Cavallito and J. Bailey; Allicin, the Antibacterial Principle of Allium sativum. I. Isolation, Physical Properties and Antibacterial Action; Journal of the American Chemical Society 66:1950.

JACS66:1952; C. Cavallito, et al; Allicin, the Antibacterial Principle of Allium sativum. II. Determination of the Chemical Structure; Journal of the American Chemical Society 66:1952.

JACS69:1710; L. Small et al; Alkyl Thiosulfinates; Journal of the American Chemical Society 69:1710.

JACS96:3929; E. Block and J. O'Conner; The Chemistry of Alkyl Thiolsulfinate Esters. VII. Mechanistic Studies and Synthetic Applications; Journal of the American Chemical Society 96:3929.

JAFC44:3413; K. M. Wall et al; Protein in Varietally Derived Apple Juices; Journal of Agricultural and Food Chemistry 44:3413.

JAFC44:3426; G. Cao, et al; Antioxidant Capacity of Tea and Common Vegetables; Journal of Agricultural Food Chemistry 44:3426.

JAFC49:2592; L. Lawson and Z. Wang; Low Allicin Release from Garlic Supplements: a Major Problem Due to the Sensitivities of Allinase Activity; Journal of Agricultural and Food Chemistry 49:2592.

JAFC50:2488; H. Xiao and K. Parkin; Antioxidant Functions of Selected Allium Thiosulfinates and S-Alk(en)yl-L-Cysteine Sulfoxides; Journal of Agricultural and Food Chemistry 50:2488.

JAFC50:3856; 0. Negishi, et al; Effects of Food Materials on Removal of Allium-Specific Volatile Sulfur Compounds; Journal of Agricultural and Food Chemistry 50:3856.

JAFC53:1974; L. Lawson and Z. Wang; Allicin and Allicin-Derived Garlic Compounds Increase Breath Acetone through Allyl Methyl Sulfide: Use in Measuring Allicin Bioavailability; Journal of Agricultural and Food Chemistry 53:1974.

JBC279:13272; Q. Guo, et al; Protein Radical Formation during Lactoperoxidase-mediated Oxidation of the Suicide Substrate Glutathione; The Journal of Biological Chemistry 279:13272.

JCI63:53; E. Orringer and M. Roer; An Ascorbate-Mediated Transmembrane-Reducing System of the Human Erythrocyte; Journal of Clinical Investigation 63:53.

JFCA2:327; G. Wierzbicka et al; Glutathione in Food; Journal of Food Composition and Analysis 2:327.

JFP60:67; K. Kyung and H. Fleming; Antimicrobial Activity of Sulfur Compounds Derived from Cabbage; Journal of Food Protection 60:67.

JLRPAW30:1703; R. Barnhart et al; Concentration-dependent antioxidant activity of probucol in low density lipoproteins in vitro: probucol degradation precedes lipoprotein oxidation; Journal of Lipid Research 30:1703.

JN114:2241; M. Friedman et al; Nutritional Improvement of Soy Flour; The Journal of Nutrition 114:2241.

JN131:955S; H. Amagase et al; Intake of Garlic and its Bioactive Components; Journal of Nutrition 131, supplement 3S:955S.

JN131:985S; B. Lau; Suppression of LDL Oxidation by Garlic; The Journal of Nutrition 131, supplement 3S:985S.

JN131:1010S; C. Borek; Antioxidant Health Effects of Aged Garlic Extract; The Journal of Nutrition 131, supplement 3S:1010S.

JN131:1067S; D. Lamm and D. Riggs; Enhanced Immunocompetence by Garlic: Role in Bladder Cancer and Other Malignancies; The Journal of Nutrition 131, supplement 3S:1067S.

JN131:1109S; T. Hoshino et al; Effects of Garlic Preparations on the Gastrointestinal Mucosa; The Journal of Nutrition 131:1109S, supplement 3S.

JOPS94:304; D. Luo, et al; Kinetics and Mechanism of the Reaction of Cysteine and Hydrogen Peroxide in Aqueous Solution; Journal of Pharmaceutical Sciences 94:304.

MCB148:183; K. Prasad et al; Antioxidant Activity of Allicin, an active Principle in Garlic; Molecular and Cellular Biochemistry 148:183.

MCT2:1295; T. Miron, et al; Inhibition of tumor growth by a novel approach: In situ allicin generation using targeted alliinase delivery; Molecular Cancer Therapeutics 2:1295.

MI2:125; S. Ankri and D. Mirelman; Antimicrobial properties of allicin from garlic; Microbes and Infection 2:125.

N207:1269; R. Hamm and K Hoffman; Changes in the Sulphydryl and Disulfide Groups in Beef Muscle Proteins During Heating; Nature 207:1269.

NC1993; Nutrients Catalog; H. Newstrom; McFarland & Company, Inc., London

NUCA25:241; M. Reicks and D. Crankshaw; Modulation of Rat Hepatic Cytochrome P-450 Activity by Garlic Organosulfur Compounds; Nutrition and Cancer 25:241.

NUCA34:42; R. Munday and C. Munday; Low Doses of Diallyl Disulfide, a Compound Derived From Garlic, Increase Tissue Activities of Quinone Reductase and Glutathone Transferase in the Gastrointestinal Tract of the Rat; Nutrition and Cancer 34:42.

PHRE59:527; B. Chance et al; Hydroperoxide Metabolism in Mammalian Organs; Physiological Reviews 59:527.

PHYRES3:50; S. Nakagawa et al; Prevention of Liver Damage by Aged Garlic Extract and Its Components in Mice; Phytotherapy Research 3:50.

PHYRES17:97; S. Banerjee, et al; Garlic as an Antioxidant: The Good, The Bad and The Ugly; Phytotherapy Research 17:97.

PHYRES18:389; M. Mukherjee et al; Prevention of Bone Loss by Oil Extract of Garlic (*Allium sativum* Linn.) in an Ovariectomized Rat Model of Osteoporosis; Phytotherapy Research 18:389.

PM59:A688; L. Lawson and Z. Wang; Pre-Hepatic Fate of the Organosulfur Compounds Derived from Garlic (*Allium sativum*); Planta Medica 59:A688.

PM60:417; J. Imai, et al; Antioxidant and Radical Scavenging effects of Aged Garlic Extract and its Constituents; Planta Medica 60:417.

PM67:13; L. Lawson, et al; Allicin Release under Simulated Gastrointestinal Conditions from Garlic Powder Tablets Employed in Clinical Trials on Serum Cholesterol; Planta Medica 67:13.

PPLAS13:261; F. Hammett and D. Wall Smith; The Influence of Sulfhydryl and Sulfoxide on Gross Regeneration in the Hermit Crab (*Pagurus Longicarpus*); Protoplasma 13:261.

PPLAS15:59; D. Wall Hammett and F. Hammett; The Growth Reaction of Embryonic Marine Forms to Sulfhydryl and Sulfoxide; Protoplasma 15:59.

Q11.N5V928; Edited by S. Park et al; Healthy Aging for Functional Longevity: Molecular and Cellular Interactions in Senescence; Annals of the New Your Academy of Sciences, Volume 928.

Q11.N5V928:327; H. Chung et al; The Inflammation Hypothesis of Aging: Molecular Modulation by Caloric Restriction; (in ISBN1573312851).

QD305.S3C48; Edited by S. Patai and Z. Rappoport 1993; Supplement S: The Chemistry of Sulphur-containing Functional Groups; John Wiley & Sons, New York, N.Y.

QD305.S3C48:633; R. Singh and G. Whitesides; Thiol-Disulfide Interchange (in QD305.S3C48).

QD305.S3S14; Edited by Z. Alfassi, 1999; S-Centered Radicals; John Wiley & Sons, New York, N.Y.

QD305.S3S14:289; P. Wardman; Thiyl Radicals in Biology: Their Role as a "Molecular Switch" Central to Cellular Oxidative Stress (in QD305.S3S14).

QH506.D384; M. Daune, 1999; Molecular biophysics—Structures in motion; Oxford University Press Inc., New York, N.Y.

QH506.D384:211; M. Daune; Proteins (in QH506.D384).

QP141.N48; H. Newstrom, 1993; Nutrients Catalog; McFarland & Company Inc. Jefferson, N.C.

QP141.N48:249; Cysteine (in QP141.N48).

QP535.O1R43; Edited by D. L. Gilbert and C. A. Colton; Reactive Oxygen in Biological Systems, 1999; Kluwer Academic, New York, N.Y.

QP535.O1R43:33; R. Huie and P. Neta; Chemistry of Reactive Oxygen Species (in QP535.O1R43).

QP551.B27; S. Bach, 1952; The Metabolism of Protein Constituents in the Mammalian Body; Clarendon Press, Oxford England.

QP551.B27:227; Deficiency Diseases of the Liver (in QP551.B27).

QP552.P4S93; Chaired by D. Parsons, 1976; Peptide Transport and Hydrolysis; Van Gorcum, Assen, The Netherlands.

QP552.P4S93:151; Y. Kim; Intestinal mucosal hydrolysis of proteins and peptides (in QP552.P4S93:151).

QP551.P48; G. Petsko and D. Ringe, 2004; Protein Structure and Function; New Science Press Ltd, London, UK.

QP551.P48:92; Control by pH and Redox Environment (in QP551.P48).

QP551.T6913; Translated from Russian by H. Dixon, Y. Torchinskii, 1974; Sulfhydryl and Disulfide Groups of Proteins; Consultants Bureau, New York.

QP551.T6913:94; Oxidation of S—S Groups (in QP551.T6913).

QP552.G58F585; edited by J. Vina, 1990; Glutathione: Metabolism and Physiological Functions; CRC Press, Boca Raton, Fla.

QP552.G58F585:125; R. Freedman; The Formation of Disulfide Bonds in the Synthesis of Secretory Proteins: Properties and Role of Protein Disulfide-Isomerase (in QP552.G58G585).

QP552.G58G54; Edited by N. Taniguchi et al, 1989; Glutathione Centennial: Molecular Perspectives and Clinical Implications; Academic Press, New York, N.Y.

QP552.G58G54:57; N. Tateishi and Y. Sakamoto; Regulation of Glutathione Level in Primary Cultured Hepatocytes (in QP552.G58G54).

QP552.G58G54:73; H. Gilbert; Thermodynamic and Kinetic Constraints on Thiol/Disulfide Exchange Involving Glutathione Redox Buffers (in QP552.G58G54).

QP552.G58G54:407; S. Bannai et al; Regulation of Glutathione Level by Amino Acid Transport (in QP552.G58G54).

QP601.E515; Edited by W. Jakoby, 1980; Enzymatic Basis of Detoxification Volume II; Academic Press, New York, N.Y.

QP601.E515:131; R. Weisiger and W. Jakoby; S-Methylation: Thiol S-Methyltransferase (in QP601.E515).

QP606.G59G59; N. Vermeulen et al, 1996; Glutathione S-Transferases: Structure, Function and Clinical Implications; Taylor & Francis Ltd., London, England.

QP606.G59G59:199; T. Ishikawa and K. Akimaru; Transport of Glutathione S-Conjugates from Cancer Cells: Function and Structure of the GS-X Pump (in QP606.G59G59).

QP722.A8A586; Edited by L. Packer, et al, 2002; The Antioxidant Vitamins C and E; AOCS Press, Champaign, Ill.

QP722.A8A586:133; L. Packer and U. Obermuller-Jevic; Vitamin E: An Introduction (in QP722.A8A586).

QP801.G6C6; Edited by S. Colowick et al, 1954; Glutathione; Academic Press, New York, N.Y.

QP801.G6C6:3; M. Calvin; Mercaptans and Disulfides: Some Physics, Chemistry, and Speculation (in QP801.G6C6).

R850.A1A3V289; Edited by M. Friedman, 1990; Nutritional and Toxicological Consequences of Food Processing; Plenum Press, New York, N.Y.

R850.A1A3V289:171; M. Friedman; Prevention of Adverse Effects of Food Browning (in R850.A1A3V289).

R850.A1A3V459; edited by Jackson et al, 1999; Impact of Food Processing on Food Safety; Kluwer Academic, New York, N.Y.

R850.A1A3V459:161; G. Sarwar et al; Influence of Feeding Alkaline/Heat Processed Proteins on Growth and Protein and Mineral Status of Rats (in R850.A1A3V459:161).

RA784.N836; Edited by P. Lachance, 1997; Nutraceuticals: Designer Foods III Garlic, Soy and Licorice; Food & Nutrition Press, Inc. Trumbull, Conn.

RA784.N836:311; G. Guhr and P. Lachance; Role of Phytochemicals in Chronic Disease Prevention (in RA784.N836).

RB170.B57; Edited by L. Packer and E. Cadenas, 1995; Biothiols in Health and Disease; Marcel Dekker Inc, New York, N.Y.

RB170.B57:287; M, Inoue, et al; Biochemical and Clinical Aspects of Extracellular Glutathione and Related Thiols;

RB170.O96; Edited by C. Pasquier, R. Oliver, C. Auclair and 1. Packer, 1994; Oxidative Stress, Cell Activation and Viral Infection; Birkhauser Verlag, Basel Switzerland.

RB170.O96:101; A. Meister; The Antioxidant Effects of Glutathione and Ascorbic Acid (in RB170.O96).

RB170.O96:285; W. Droge et al; Abnormal Redox Regulation in HIV Infections and other Immunodeficiency Diseases (in RB17O.96).

RM666.G15K6313; H. P. Koch and L. D. Lawson, 1996; GARLIC The Science and Therapeutic Application of *Allium sativum* L. and Relates Species; Williams & Wilkins, Baltimore, Md.

RM666.G15K6313:148; H. P. Koch and L. D. Lawson; Effects on Blood Pressure, Vascular Resistance, and Heart Function (in RM666.G15K6313).

RM666.G15K6313:190; H. P. Koch and L. D. Lawson; Antioxidant Effects: Active Compounds (in RM666.G15K6313).

RM666.G15K6313:235; H. P. Koch and L. D. Lawson; References (in RM666.G15K6313).

RM666.H33P49; Edited by L. Lawson and R. Bauer, 1998; Phytomedicines of Europe. Chemical and Biological Activity; American Chemical Society, Washington, D.C.

RM666.H33P49:176; L. Lawson; Garlic: A Review of Its Medicinal Effects and Indicated Active Compounds (in RM666.H33P49).

RR2:392; P. Alexander et al; Mode of Action of Some Substances Which Protect against the Lethal Effects of X-Rays; Radiation Research 2:392.

TL69:15; R. White et al; Toxicity Evaluations of L-cysteine and Procysteine, a Cysteine Prodrug, Given Once Intravenously to Neonatal Rats; Toxicology Letters 69:15.

TP453.P7F68; Edited by S. Nakai and H. Modler 1996; Food Proteins: Properties and Characterization; VHC Publishers, New York, N.Y.

TP453.P7F68:23; R. Ludescher; Physical and Chemical Properties of Amino Acids and Proteins (in TP453.P7F68).

TP453.P7F68:281; M. Friedman, Nutrition (in TP453.P7F68)

TP453.P7F665'; Edited by S. Damodaran and A. Paraf 1997; Food Proteins and their Applications; Marcel Decker Inc., New York, N.Y.

TP453.P7F665:225; P. Cayot and D. Lorient; Structure-Function Relationships of Whey Proteins (in TP453.P7F665).

U.S. Pat. No. 5,451,412A; G. Bounous et al; Biologically Active Undenatured Whey Protein Concentrate as Food Supplement; U.S. Pat. No. 5,451,412.

WO:01/36450; T. Miron et al; S-Allylmercaptoglutathione and Uses Thereof; World Intellectual Property Organization WO 01/36450 A1.

4. DESCRIPTION OF THE PRIOR ART

4.1 Alliums and their Medicinal Benefits

Garlic, onions, and other alliums have been reputed to have beneficial medicinal properties for thousands of years. Traditional medicine has yielded a vast number of compositions containing garlic and/or onions for the treatment of a wide variety of conditions (EPMR6:56, EPMR6:115, IJEB34:634, ISBN9679786846:15). Medicinal uses include the prevention and treatment of diseases related to the heart and circulatory system, microbial infections, cancer, respiratory diseases, hypoglycemia, and as a detoxicant for heavy metal poisoning and other toxins (RM666.G15K6313, pages 135-211). In the prevention of bacterial infections, alliums (e.g. garlic) are unique as an antibiotic because they simultaneously produce a pro-biotic response, encouraging the maintenance of a healthy intestinal flora. At the same time that garlic inhibits the "bad" bacteria (streptococci, coliforms, *e. coli*, salmonellae) by a large factor (100×) it inhibits the "good" lactobacteria by a much lower amount (10×) (FM29:348). The result is that enough good bacteria are maintained to aid in digestion and vitamin formation, while suppressing the bad bacteria. Another interesting aspect is the apparent inability of most bacteria to develop resistance to garlic (MI2:125), although apparently the lactobacteria have evolved a tolerance.

In addition to disease prevention, garlic and other alliums have been used to provide general health benefits such as antioxidant protection, strengthened immune system, anti-hepitoxic protection, anti-inflammatory protection, improved digestion, and for repelling insects (RM666.G15K6313, pages 135-211).

Within the last two decades, there have been various significant discoveries relating to the importance of nitric oxide (NO) in biological systems. Nitric oxide and its metabolites have been shown to play a significant role in the circulatory and immune systems, to regulate enzyme activation/deactivation, and to act as oxidants and antioxidants. Several of the health benefits from garlic are related to its interactions with nitric oxide in vivo. For example, garlic has been shown to increase the activity of the eNOS enzyme that synthesizes the nitric oxide that dilates blood vessels, thereby promoting good blood flow (BST23:S136). Interestingly, garlic simultaneously decreases the activity of the INOS enzyme that synthesizes the nitric oxide that damages tissue during an immune response, thereby reducing chronic inflammation (BST23:S136).

Daily garlic consumption has been associated with health maintenance and is recommended for successful aging (E185.96.D368:107). Literally thousands of scientific articles have been published on garlic, allicin, and related compounds, with 2240 references listed in RM666.G15K6313, pages 235-319.

Hundreds of animal studies have been performed with many clearly demonstrating beneficial effects from the consumption of garlic, allicin, or related compounds, as illustrated by the following examples.

When rats are fed a high fructose diet, they tend to gain weight significantly. In an experiment of 5 weeks duration that fed a high fructose diet to rats (AJH16:1053), for the first 3 weeks both the control and experimental groups had a weight gain of approximately 10%. For the remaining 2 weeks the control group continued to gain another 10% in weight, but the group that was also fed allicin (8 mg/kg) had a 3% loss in weight (despite continuing to eat all the food). While these results are impressive, their utility is limited because a comparable dosage for a 70 kg human would be 560 mg of allicin, or 56 cloves of raw garlic per day.

In addition to causing weight gain, a high fructose diet causes rats to become hyperinsulinemic, hyperlipidemic, and hypertensive. In an experiment (AJH14:377) that was nearly identical to the previous one, at the end of 5 weeks the rats that were also fed allicin (8 mg/kg) during the final 2 weeks had a significantly smaller percentage increases than the control group in insulin (+62% versus +252%), triglycerides (+6.8% versus +113%), and blood pressure (+5.2% versus +13.5%). Again, the dosage was equivalent to 56 cloves of garlic/day in humans.

Another experiment shows that an oil extract of garlic (primarily DADS) could exhibit an estrogenic property (i.e. mimic the hormone) in ovariectomized rats (PHYRES18: 389). A dosage of 100 mg/kg eliminated the weight gain and substantially reduced the loss of bone density and the changes in urinary and serum parameters that were seen in the control group. Again, the dosage utilized (equivalent to hundreds of cloves of garlic per day for a person) limits the utility of these results.

4.2 Allicin—an Effective Ingredient from Alliums, Especially Garlic.

The first medicinal property of garlic to be studied with modern scientific methods was its antibacterial action (JACS66:1950). The active ingredient was isolated and given the name allicin.

The chemical structure of allicin was determined to be (JACS66:1952):

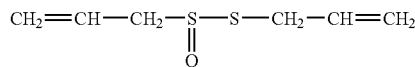

Numerous allicin derived organosulfur compounds have also been found to provide medicinal benefits; however, the benefits attributed to allicin tend to be the superset of these, in part because many of these compounds produce similar metabolites in vivo (PM59:A688).

Allicin is a thiosulfinate, with R and R' being allyl groups in the following formula:

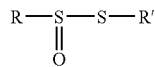

Other thiosulfinates have been found to also provide medicinal benefits, such as the anti-tumor properties of methyl methane thiosulfinate (R and R' being methyl groups), a compound formed by the crushing of onions or garlic, and a metabolite of the cruciferae vegetables (cabbage, broccoli, etc.) (FCT33:537). However, the sulfur content of other common fruits and vegetables is at most 25% that of garlic (onions and broccoli contain this amount (RM666.G15K6313, page 39)), so in the context of this invention garlic is the model dietary source of thiosulfinates and other *allium* related compounds.

The extremely high permeability of biological membranes to allicin also contributes to its biological activity (BBA1463: 20).

Allicin has a garlic-like taste and odor and burns the mouth if consumed directly.

4.2.1 Allicin is a Broad Spectrum Anti-Microbial Agent that is Effective in Preventing Infections, Including the Common Cold Allicin has been shown to be a broad spectrum antimicrobial agent that significantly inhibits many strains of bacteria, fungi, viruses, and parasites (MI2:125). It has even been shown to be effective in the prevention and treatment of the common cold (AIT15:189), reducing the frequency of infection (24 vs. 65 for the placebo group), and reducing the duration of symptoms to an average of 1.5 days (vs. 5 days for the placebo group).

The mechanism of antimicrobial action was initially proposed to be related to allicin's reaction with cysteine (JACS66:1952), eliminating the free SH groups essential to bacterial proliferation. Allicin was subsequently shown to be a very potent inhibitor of "SH-enzymes" (BIJ63:514). This model for its mode of action is still commonly accepted (MI2:125) and is well supported by experimental evidence. The activity of the well-known sulfhydryl-dependent enzyme papain was shown to be rapidly inhibited to 1% of its initial activity by allicin and to rapidly be completely restored by an SH-reducing agent (BBA1379:233).

But there is some question whether enzyme inhibition by allicin is universally due to sulfhydryl blocking. An investigation of the inhibition of acetyl-CoA synthase that compared the effect of allicin with that of another well known thiol-group blocker of acetyl-CoA synthase (p-hydroxymercuribenzoate) found that allicin was unexplainably effective (FEBS261:106). Their conclusion was that allicin must be a specific inhibitor of acetyl-CoA synthase.

In another example, allicin has been shown to reduce the rate of bacterial RNA synthesis to below 1% of that of control cells. The effect on RNA synthesis was so dramatic that the authors suggested that allicin is acting not as a general inhibitor of sulfhydryl-dependent enzymes but rather as a specific inhibitor of RNA synthesis (AAC32:1763).

Other thiosulfinates have been shown to have similar antimicrobial properties, such as methyl methane thiosulfinate (R and R' methyl) and methyl allyl thiosulfinate (R methyl and R' allyl), which have been shown to be effective against *E-coli* O157:H7 (BBBIO65:966). Tests comparing the activity of 8 types of thiosulfinates against 25 types of bacteria and fungi found that they were all active, with the lower molecular weight compounds (2, 4, and 6 carbons) being most effective against the gram-negative bacteria and the longer carbon chain compounds more active against gram-positive bacteria (JACS69:1710), which the authors attribute to the increased lipid solubility of molecules with longer carbon chains. Branched compounds were active, but less so than the unbranched compounds, which was attributed to the better ability of smaller molecules to gain access to the critical —SH groups of enzymes.

4.2.2 Garlic and Allicin have Powerful Antioxidant and Oxidant Properties

Studies of garlic, allicin and other *allium* related compounds have shown both antioxidant and oxidant activity.

The sulfur atom (and molecules containing sulfur) can have oxidation states in the range of −2 to +6. Therefore, sulfur can participate in a wide variety of redox reactions. A table of the oxidation states of sulfur compounds (QP801.G6C6:4) shows the oxidation states of the various sulfur compounds that are relevant to the present invention, including RSH (−2), RSR' (−2), RSSR' (−1), RSOH (0), RSOSR' (0), and RS(O)SR' (0). From this list, it can be seen that the thiol (RSH) has the lowest oxidation state, the disulfide (RSSR') is more oxidized, and the thiosulfinate (RS(O)SR') is still more oxidized.

In a study of the suppression of LDL oxidation by garlic related compounds (JN131:985S), S-allylcysteine, N-acetyl-S-allylcysteine, alliin, and especially S-AllylMercaptoCysteine (SAMC) were shown to significantly reduce Cu2+ induced LDL oxidation, but allicin increased the LDL oxidation to almost 3× the level of the control.

In a study of the total antioxidant capacity of 22 vegetables measuring the reduction of peroxyl radicals (*OOH), hydroxyl radicals (*OH), and of Cu2+ catalyzed free-radical chain reactions, garlic homogenate rated a "total antioxidant score" of 23.2 (second only to kale), approximately 3 times the average, showing that garlic is an excellent antioxidant (JAFC44:3426). Interestingly, the garlic homogenate showed significant antioxidant capacity against Cu2+ induced oxidation (contrary to the effect of allicin alone, as reported in JN131:985S), which implies that additional compounds in the garlic homogenate were active.

In a chemiluminescence assay of the antioxidant properties of eight commercial garlic products, only "AGE" (Aged Garlic Extract, a garlic supplement product from Kyolic Research) had net antioxidant activity (JN131:1010S). The AGE product contains primarily the water-soluble compound S-allylcysteine (SAC), but it also contains S-AllylMercaptoCysteine (SAMC) and the lipid-soluble compounds diallyl sulfide, diallyl disulfide (DADS) and diallyl trisulfide. The other products all contained garlic powder and produced allicin upon ingestion.

In another study comparing the constituents of AGE with garlic extract, a chemiluminescence assay showed raw or heated garlic extract to be pro-oxidant, but AGE to be a potent antioxidant (PM60:417). Of the 11 various organosulfur components derived from garlic that were analyzed, SAMC and glutathione were shown to be the most effective antioxidants (by approximately a factor of two, compared to the other compounds).

But AGE also contains protein F4 from garlic which is an immunostimulant that can cause inflammation (JN131:1067S). In this case, the oxidants are produced in vivo by the immune system itself, which is why they don't show up in other in vitro experiments utilizing AGE.

Garlic extract (crushed fresh garlic in water) at a moderate dosage (25 mg/kg, corresponding to 0.05 mg/kg of allicin) has been shown to significantly protect against chromosomal aberrations induced by mutagenic agent cyclophosphamide (CL176:31) without introducing any significant chromosomal damage in the controls. But a more extended study (sampling at 6 hr, 12 hr, 18 hr, 24 hr, 7 days, 30 days and 60 days) has shown that the garlic extract itself can introduce chromosomal damage, especially at higher doses (50 or 100 mg/kg). Interestingly, although some chromosomal damage appeared for a few days at the lowest dosage tested (25 mg/kg), after 30 days there was no significant difference in chromosomal damage relative to the controls (FST34:43).

A skeptical study on the antioxidant properties of allicin and several other thiosulfinates (JAFC50:2488), after noting that many other investigators have attributed antioxidant effects to thiosulfinates (e.g. BBA1379:233), proceeded to test these thiosulfinates against $*O_2^-$ (superoxide radical), $H_2O_2$ (hydrogen peroxide), $O_2^1$ (singlet oxygen), $*OH$ (hydroxyl radicals). The study found no significant antioxidant activity other than the ability to scavenge $*OH$ (a somewhat meaningless result in itself because almost all organic molecules can do this).

Another study (MCB148:183) on the ability of garlic powder to scavenge $*OH$ also shows (although not noted by the authors) that high concentrations of garlic powder actually increase the level of $*OH$ in their control group (garlic powder administered but no added $*OH$).

These various studies show that the results depend on which antioxidant or pro-oxidant property is being tested, which garlic related compounds are being tested, the concentration, and the method of testing. From the published literature it appears that neither garlic, allicin, nor AGE is an antioxidant under all circumstances, but they are each effective antioxidants in many circumstances.

An extensive review, titled "Garlic as an Antioxidant: The Good, The Bad and The Ugly" (PHYRES17:97), illustrates the diversity of reported antioxidant, oxidant, and paradoxical effects, including a reversal of antioxidant effect with an increasing dose of raw garlic homogenate.

Another summary of the antioxidant effects of allicin and related compounds (RM666.G15K6313:190) concludes that at most concentrations in vivo, allicin (generally a pro-oxidant compound) is metabolized to allyl mercaptan (a strong antioxidant), but at higher concentrations the conversion saturates and allicin displays its pro-oxidant effects.

4.2.3 Toxicity of Allicin and Raw Garlic Powder

Because different garlic preparations contain different garlic constituents, a study of their toxicity was performed (JN131:1109S). Endoscopic examination of the stomach mucosa of dogs 24 hours after the direct administration of raw garlic powder detected erosion at 15 out of 18 sites. But if the garlic powder had been boiled (to inactivate the alliinase, thereby eliminating any allicin), no erosion was observed, but there was some redness. When the "AGE" garlic product was used (which contains no allicin), no erosion or redness was observed.

Enteric-coated garlic products release their contents (including enzymatically produced allicin) into the intestine (instead of the stomach). The examination of the intestine of a dog 3 hours after the administration of three tablets showed damaged and lost epithelial cells at the top of crypts (JN131:1109S). The authors concluded that the safety of enteric-coated garlic products was questionable and recommended the use of AGE instead.

4.2.4 Sources of Allicin 4.2.4.1 Raw Garlic

Upon crushing garlic and breaking its cell walls, the enzyme alliinase converts the previously separately compartmentalized S-allylcysteine sulfoxide (alliin) instantly to allicin (RM666.G15K6313, page 48). Interestingly, for the garlic plant itself this produces the antimicrobial agent precisely when and where it is needed: in response to the destruction of its cell walls by bacteria or fungi. (For humans it tends to burn the mouth when chewed.) Other species of alliums also contain one or more S-alk(en)cysteine sulfoxides with the general formula $RS(O)CHC_2H(NH_2)COOH$ which are also converted to the corresponding thiosulfinates by an alliinase when crushed. For Chinese chives (*A. tuberosum*) the primary substituted group (R) is methyl, for scallion (*A. fistulosum*) and chives (*A. schoenoprasum*) R=propyl, and for onions (*A. cepa*) R=1-propenyl (JAFC50:3856). All of these are representative of the range of compounds related to the present invention, however the discussion here concentrates on allicin derived from garlic (*A. sativum*, R=allyl) because this is the most researched compound of its class.

It is important that they be crushed while still raw because the enzyme alliinase is rapidly destroyed by cooking. The analysis of cooked garlic that was not crushed prior to cooking shows that it does not provide any allicin at all (RM666.G15K6313, page 68), although the other organosulfur compounds in cooked garlic probably provide some health benefits, to the extent that they survive being cooked.

Even if allicin is formed prior to cooking, there is significant loss of organosulfur compounds during cooking. For example, stir-frying smashed garlic cloves in hot soybean oil for 1 minute in a Chinese wok eliminated all of the allicin and only retained 16% of the other sulfides (RM666.G15K6313, page 68). The same set of tests showed that boiling for 20 minutes eliminated 93% of the thiosulfinates and 97% of the sulfides.

Average daily consumption of garlic by Americans is reported to be less than ⅓ of a clove per clay (1.4 g/day, average clove 5 g, NUCA34:42). Indian food commonly contains garlic and onions, especially in dishes cooked with meat. A population in China has been reported to consume 4 cloves of garlic per day (RA784.N836:311, presumably this garlic has been cooked!). Some garlic is contained in processed foods. It is unlikely that any population consumes more than one clove a day of fresh garlic and 10 cloves a day of cooked garlic.

For dosage calculation purposes, assuming that cooking retains 10% activity, the maximum equivalent dietary consumption of *allium* related foodstuffs is estimated to be the sum of 10 cloves of cooked garlic and one clove of raw garlic, which equals 2 cloves of raw garlic, or 20 mg of bioequivalent allicin per day (see below for the definition of allicin bioequivalence).

4.2.4.2 Garlic Supplements that Produce Allicin from Alliin

The poor stability of allicin has traditionally prevented it from being incorporated directly into dietary supplements. Instead, these products contain the allicin precursor alliin along with the enzyme alliinase, with an enteric coating utilized to prevent their mixing together until they reach the intestine. The allicin release from these products has been problematical, because if the coating dissolves too soon the stomach acids will instantly deactivate the alliinase enzyme, but if the coating lasts too long, the reaction never occurs. In a survey of dietary supplements published in 2001, only one supplement achieved its claimed bioavailable allicin (JAFC49:2592).

For example, in 1993 a change in the manufacturing process for "Kwai" garlic tablets caused their allicin yield to change from 73% of the theoretical yield to only 23%. This was discovered only after several clinical trials were conducted using these tablets (on the serum cholesterol lowering ability of garlic). In retrospect, the results of the various clinical trials can be seen to correlate with the actual allicin release from the various products tested (PM67:13).

The lack of consistent ability of garlic tablets to meet their claimed allicin yield remains a problem even today (see www.consumerlab.com/results/garlic.asp).

4.2.4.3 Allicin Supplements Containing "Pure" Allicin

A proprietary process has been developed for stabilizing allicin, allowing the non-enzymatic delivery of allicin in a capsule. These capsules are currently only available from Allicin International (www.allimax.com). The actual allicin content is not printed on the label, nor is this information available from the manufacturer. Instead, the allicin content of each Allimax capsule is described as "the same amount of allicin that you get from 1 clove of top quality garlic" (Peter Josling, response to inquiry).

4.2.4.4 Dietary Supplements Containing Garlic Oil

Garlic oil capsules contain various allyl sulfides, of which DADS has the highest concentration (RM666.G15K6313, Table 3.20). These products produce more consistent "bioavailable allicin" (see below) than the typical garlic powder tablet, however the garlic oil capsules themselves are less standardized. The taste and odor of DADS and the other constituents of garlic oil significantly limit the concentration of active ingredients (the garlic oil is typically heavily diluted, e.g. the capsules contain over 99% vegetable oil). A comparison of commercial garlic oil products found a 50 to 1 range in their total content of allyl sulfides (RM666.G15K6313, Table 3.21).

4.2.5 Metabolites of Allicin

The primary direct metabolite of allicin has been determined to be allyl mercaptan (PM59:A688). The disappearance of allicin is so rapid and so complete that it is undetectable in blood, urine, or stool, even after consuming large amounts of fresh garlic (e.g. 25 g) or pure allicin (60 mg) (JAFC53:1974).

Because of the rapid formation of allyl mercaptan from allicin, other direct metabolites are not readily detected. However, the consumption of allicin and various allicin-derived compounds have been shown to lead to the rapid metabolic formation of allyl methyl sulfide (AMS) and the eventual formation of acetone, either of which can be measured in breath. Therefore, breath analysis for AMS or acetone provides a non-invasive method for verifying the allicin equivalent bioavailability of these compounds (JAFC53:1974). (The term "bioavailable allicin" is used for this, although no allicin is necessarily involved. A more accurate term would have been "allicin bioequivalence".)

Other garlic related organosulfur compounds that metabolize directly in blood to allyl mercaptan (disappearing in the process) include diallyl disulfide, diallyl trisulfide, ajoene, and S-AllylMercaptoCysteine (SAMC) (PM59:A688). These have all also been shown to produce both breath AMS and acetone, but interestingly the compound DAS (similar to DADS, but with only one sulfur atom) only produces breath acetone and the compound. SAC (similar to SAMC but with only one sulfur atom) produces no breath AMS or acetone (JAFC53:1974).

It has been proposed that in vitro or ex vivo studies of the mechanism of action of these compounds should not use these compounds themselves, but rather should use allyl mercaptan, or possibly a further metabolite of allyl mercaptan (RM666.G15K6313, page 214). In other words, compounds which disappear rapidly in the body can lead to misleading results if they are used by themselves in experiments outside of the body. However there are no dietary supplements based on allyl mercaptan itself, presumably due in part to its strong odor (which is much worse than the odor of garlic itself).

4.2.5.1 The Pre-Hepatic Fate of the Organosulfur Compounds Derived from Garlic

While there sometimes seems to be a confusing variety of garlic-derived organosulfur compounds, when they are consumed they all are exposed to the reactive cysteine of proteins (including the cysteine in foods being simultaneously consumed) and they are all exposed to blood (e.g. during transport from the intestine to the liver). An in vitro study was performed (PM59:A688) to determine their primary reaction products in these environments.

In the presence of glutathione and an active glutathione-reductase system (e.g. within most types of cells), allicin is rapidly metabolized to allyl mercaptan. This can be shown to occur in less than one minute by the analysis of red blood cells that have been exposed to allicin (PM59:A688). The results are given in Table 1 of PM59:A688 and are summarized here in Table I for the compounds most relevant to the present invention:

TABLE I

Reactions of organosulfur compounds in the presence of blood or cysteine

| Compound | Reaction with Cysteine | | Reaction in Blood | |
|---|---|---|---|---|
| | Half-life (min) | Product (moles) | Half-life (min) | Product (moles) |
| Allicin (1.6) | <1 | SAMC (2) | <1 | AllylSH |
| DATS (0.8) | <2 | SAMC (1), AllylSH (0.6) | 4 | AllylSH |
| DADS (0.8) | 45 | SAMC (1), AllylSH (1) | 60 | AllylSH |
| SAMC (0.8) | NR | | 3 | AllylSH |
| AllylSH | 80 | SAMC (0.8) | NR | |

These results show that regardless of which compound is consumed, SAMC can be formed as an intermediate and allyl mercaptan (AllylSH) is the primary final product in blood.

4.2.5.2 Metabolites of Allyl Mercaptan

The primary direct metabolites of allyl mercaptan are the disulfide DADS and various mixed disulfides, especially those involving cysteine. The disulfide can form via oxidation, but the more likely path is through various thiol-disulfide exchange reactions (see below). The mixed disulfides are also formed primarily via exchange reactions. The exchange reactions do not require "metabolism" per se, because the mere presence of other disulfides (or mixed disulfides) is sufficient for these reactions to occur.

Although finding allicin or its metabolites in the blood or urine after garlic consumption has been elusive, it has been known for some time that allyl mercaptan and AMS are components of the breath soon after garlic consumption, with the allyl mercaptan disappearing by 1 hour and the AMS having substantially disappeared in 20 hours (JAFC53:1974). Because AMS is S-methylated allyl mercaptan, the "thiol S-methyltransferase" enzymes are likely to be involved (QP601.E515:131, BBA46:217). These enzymes are distributed in a variety of tissues, but the concentrations are highest in the digestive and excretory tract (stomach mucosa, cecal mucosa, colonic mucosa, liver, and kidney) and lung, indicating that their primary purpose is probably detoxification (QP601.E515:131).

Concurrent with the disappearance of AMS, a significant increase in breath acetone appears, remaining substantially elevated for almost 40 hours, perhaps due to increased triglyceride metabolism (QP601.E515:131). However, no metabolites beyond AMS have been linked to this effect.

The S-conjugation between allyl mercaptan and nitric oxide (forming a nitrosothiol) has also been shown to be biologically significant. Nitrosothiol formation increases the effective lifetime of nitric oxide in circulation from a half life of about 5 seconds to many minutes, potentiating its systemic effects (RB170.B57:287 FIG. 3). Many of the biological effects of nitric oxide have been found to involve nitrosothiols, rather than nitric oxide itself.

4.2.5.3 In Vivo Allicin Production from DADS

Allicin has been shown to be produced in the liver from diallyl disulfide (DADS) via several cytochrome P-450 enzymes (e.g. CYP2E1) and flavin-containing monooxygenases (DMD27:835). Thus the in vivo production of allicin can be accomplished by any mechanism that delivers DADS molecules to the liver. (Note: the DADS molecule is identical to an allicin molecule with the oxygen atom removed. Conversely, the monooxygenation of a sulfur atom in a DADS molecule results in the formation of an allicin molecule.)

The activity of the enzymes is moderate (up to $8 \times 10^{-8}$ pmol/min/pmol CYP2D6), resulting in approximately 30% conversion of DADS to allicin in 30 minutes (DMD27:835). Although not mentioned in the reference, it is interesting to note that because any DADS in circulation is likely to pass through the liver multiple times, this results in a "sustained release" of allicin. In comparison, if 100% of the DADS was converted to allicin in the first pass, the release would be much more rapid (and of shorter duration). Also, because Cytochrome P-450 enzymes are present in a variety of cell types, the enzymatic production of allicin from DADS may also occur in cells throughout the body ("distributed release").

4.2.5.4 Targeted Delivery of Allicin

By chemically conjugating the enzyme alliinase to an antibody to a specific tumor marker (ErbB2) that is present on the surface of tumor cells, and also administering alliin into circulation, allicin is produced at the specific location of the tumor (MCT2:1295), and only at this location. This was shown to inhibit tumor growth nearly completely, without significantly affecting the rest of the body. It should also be effective as a preventive of metastases because the general circulation of both the conjugated alliinase and the alliin can find the tumor cells before they are otherwise detectable.

4.3 Cysteine—Amino Acid, Biothiol, and Glutathione Precursor

Cysteine is a sulfur containing amino acid which is an important constituent of proteins. In fact, the SH group of cysteine (when ionized) is the most reactive group in proteins (TP453.P7F68:23). The active site of many enzymes (e.g. proteases) involves cysteine, where the reactivity of the SH group contributes to the activity of the enzyme.

Cysteine is a thiol (it has a terminal "SH" group) and shares many properties with other biothiols (thiols in biological systems). It is able to participate in thiol-disulfide exchange reactions with almost all types of disulfides, resulting in a wide variety of mixed disulfides (QD305.S3C48:633). Thiol-disulfide exchange reactions allow the formation of disulfide bonds (which are covalent bonds, so they are quite strong) and their later separation, with no energy involved other than the thermal energy that brings them together or apart.

The formation of the tertiary structure of proteins (protein folding) depends upon the proper formation of disulfide bonds between pairs of cysteines within the polypeptide chain of the protein. These disulfide bonds can stabilize or regulate the protein structure and activity. Disulfide bonds can also link adjacent proteins, providing structure to tissues. Disulfide bonds also affect the stiffness of the eye lens, and the excessive formation of disulfide bonds is implicated in the development of cataracts (BBRC242:1).

Cysteine tends to auto-oxidize to cysteine disulfide (cystine, CySSCy) in the presence of oxygen. Inside cells, the "reductive" environment provided by the maintenance of reduced glutathione (by glutathione reductase) tends to keep the cysteine reduced (CySH), but in an extracellular environment, cysteine disulfide forms. The low solubility of cysteine disulfide can result in the formation of kidney stones.

Cysteine exhibits toxicity in large dosage, but non-toxic prodrugs exist (TL69:15), such as N-acetylcysteine (NAC) and L-2-Oxo-thiazolidine (OTZ) (JSR65:165).

4.4 Glutathione, the Mother of all Antioxidants

Glutathione is a tripeptide composed of the amino acids glutamic acid, cysteine, and glycine. An advantage of glutathione for the storage and transport of cysteine is that it is far less toxic than cysteine at high concentrations (QP552.G58G54:57). Due to the available SH group of the cysteine, glutathione is a biothiol and shares the antioxidant properties that are common to thiols. But there are also various enzymes that specifically utilize glutathione, giving it some unique antioxidant (and oxidant) properties as well.

Glutathione has a high concentration (1-5 mM) in the aqueous environments of most cells and organelles (e.g. in the cytoplasm and inside mitochondria). Glutathione does not pass freely through lipid membranes, but transport systems allow its constituent amino acids to enter cells (and organelles) and also allow GSSG, other glutathione conjugates (GS-X), and in some cases reduced glutathione (GSH) to be excreted from cells.

Glutathione has a broad diversity of functions in biological systems (too many to do justice to here, see the many examples throughout this application). An extensive treatise on glutathione is available (ARB52:711).

4.4.1 Antioxidant and Oxidant Properties of Glutathione

Like other thiols, reduced glutathione (GS⁻, or GSH) will readily donate the electron (or the hydrogen atom) of its SH group, even to relatively weak oxidants. For example, reduced glutathione can react non-enzymatically to reduce $H_2O_2$ and other hydroperoxides, scavenge *$O_2$ (superoxide) radicals, and detoxify other reactive oxygen species (ROS). The conventional view is that this is via electron or hydrogen atom donation, resulting in the formation of the glutathiyl free radical (GS*). Examples of the formation of GS* from the non-enzymatic reduction of a wide variety of ROS are common in the literature (e.g. QD305.S3S14:289). The formation of GS* radicals from a large variety of antioxidant activities of GSH and the fate of these GS* radicals is explored in depth in QP552.G58G566:43. The newly formed free radical is usually a weaker oxidant than the original oxidant and tends to be short lived because it rapidly dimerizes to form oxidized glutathione (GSSG).

Further analysis has shown that the dimerization of GS* to GSSG can not be by simple conjugation because in normal biological systems the concentration of GS* is always low compared to the concentration of other possible reactants. In other words, before a newly formed GS* can encounter another GS* it will encounter a variety of other molecules that it can readily react with. Given the observed preferential formation of GSSG, the probable reaction paths have been investigated (QP552.G58G566:43, QD305.S3S14:289). In the absence of oxygen, GS* will react readily with the GS⁻ molecules that are readily available. This conjugation of GS* with GS⁻ produces GSSG*⁻ which is a powerful reductant. The formation of a powerful reductant from even a mild oxidant has been described as a "molecular switch" that is central to the biological response to oxidative stress. In the presence of oxygen, GSSG*⁻ rapidly reacts with $O_2$ to form superoxide (*$O_2$) and GSSG. Alternatively, the GS* free radical can react directly with $O_2$ to form GSOO* (another free radical). Further reactions of the GSOO* with (for example) GSH produce products such as GSO* and GSOH (a sulfenic acid) along with the formation of GSSG (QD305.S3S14:289).

In any case, despite some controversy about the path from GSH to GSSG, GSH has been clearly shown to be an effective (and essential) antioxidant in almost all life forms, so the potentially damaging reaction products just discussed must either not form in vivo, or they are effectively managed and have a negligible effect.

Unlike other thiols, there are a variety of enzymes that are specific to glutathione that augment the antioxidant (and oxidant) activity of glutathione and, indirectly, the other intracellular antioxidants.

Glutathione's antioxidant properties are augmented by various GSH-peroxidase enzymes that use GSH to reduce peroxides (e.g. hydrogen peroxide, $H_2O_2$), producing GSSG in the process, which in turn is reduced back to 2 GSH by GSH-reductase (ARB52:711). Glutathione transferases (see below) also have peroxidase activity.

Glutathione (GSH) serves as a critical antioxidant and is perhaps the only molecular antioxidant whose total depletion can directly cause death (RB170.O96:101). The central antioxidant role of glutathione is due to its ability, via the "antioxidant network" (QP772.A8:139, FIG. 9.2), to recycle almost all other antioxidants to their reduced state. Therefore, insufficient GSH can also result in the accumulated oxidation of the various other antioxidants.

Glutathione has two major roles in the antioxidant network (See FIG. 1, derived from FIG. 9.2 of QP722.A8A586:133), the first of which is the participation in a sequence of oxidation/reduction reactions originating with the original oxidant and terminating in the formation of GSSG. For example, an original oxidant (or an intermediate antioxidant, such as oxidized vitamin E) may oxidize an ascorbate molecule (vitamin C), becoming reduced in the process. The newly oxidized vitamin C (ascorbyl radical) is less reactive than the original oxidant. The oxidized vitamin C can in turn oxidize a GSH molecule, becoming a reduced (ascorbate) molecule again (FRBM20:543). The oxidized GSH molecule (GS*) is rapidly dimerized to GSSG. Hence the original oxidant has caused the formation of a relatively non-reactive GSSG molecule, with vitamin C being used (and recycled) in the process.

The GSSG can in turn be recycled to 2 GSH by the enzyme glutathione reductase. This enzyme uses NADPH+H⁺ as a reductant, producing NADP⁺ which is typically recycled back to NADPH as part of the pentose pathway of energy metabolism. The net effect is that the energy input (e.g. from glucose) drives the reduction of GSSG, which in turn drives the reduction of most of the other antioxidants that participate in the antioxidant network.

Many other antioxidants (e.g. vitamin E, QP722.A8A586:133) can also serve as an intermediate in an oxidation/reduction pathway, still leading to the formation of oxidized glutathione (GSSG) and its ultimate reduction by NADPH. Interestingly, vitamin C has been shown to be able to pass through the cellular membrane of red blood cells and to thereby couple the intracellular antioxidant network to the external environment (JCI63:53). The uptake of oxidized vitamin C (DHA) is active via the glucose transporter in the cell membrane and can operate against a concentration gradient, while the reduced vitamin C (ascorbate) diffuses from the cell through the cell membrane back to the extracellular environment (FRBM24:789). The capacity for this "ascorbate cycling" by red blood cells is substantial (plasma vitamin C can be completely recycled in 3 minutes). The recycled ascorbate also protects the vitamin E in LDL from oxidizing (FRBM24:789).

Similarly, macrophages, fibroblasts, and hepatocytes have been found to be able to uptake cystine (CySSCy) via a membrane transport protein and reduce it to cysteine (2 CySH) via thiol-disulfide exchange reactions with GSH inside the cell and to subsequently release the cysteine to the extracellular environment (RB170.O96:285).

The present inventor notes that for this limited number of cell types, active transport through the cell membrane couples the intracellular antioxidant network to the extracellular environment via the following mechanism. In the extracellular environment diffusion and exchange reactions can semi-randomly transform the nature of the product of an oxidation event until it shows up as cystine at the outer surface of the cell membrane and is taken up for transport. Then inside the cell, diffusion and exchange reactions can semi-randomly transform the nature of the oxidized intermediate until it shows up as intracellular GSSG, which is then rapidly removed by the enzyme glutathione reductase, producing 2 GSH. Following further semi-random exchange reactions, reduced cysteine is passed back through the cell membrane to the extracellular environment. This contributes to the creation and maintenance of a generally reductive environment, including the local environment outside the cell, at the expense of the energy provided to glutathione reductase to drive the system.

In addition to its antioxidant function, this intracellular transport of cysteine (QP552.G58G54:407) is important because almost all other cell types only have the ability to uptake cysteine, and would "starve" if only provided with cystine (BCHS370:109). Proper function and immune response of lymphocytes appears to require a local supply of extracellular cysteine (e.g. from adjacent macrophage cells) because these cells need a higher cysteine concentration than that in circulation (AJM91__3C:140S).

Glutathione's oxidant properties are augmented by the enzyme Protein Disulfide Isomerase (PDI), which accelerates the formation of intramolecular disulfide bonds, using GSSG as the proximate oxidant (QP552.G58F585:125). Other essential oxidant properties of glutathione include its redox regulatory roles, including the control of proteins and enzymes via glutathionylation (the S-thiolation of exposed thiols on proteins) (BBRC242:1).

4.4.2 Detoxification Properties of Glutathione

Glutathione is also necessary for the detoxification of a wide variety of toxic substances (ARB52:711), including pesticides, herbicides, and industrial solvents. As a biothiol, it shares the various detoxification properties of biothiols, including the formation of complexes with metals that would otherwise be more toxic (e.g. mercury, the ability of which to to be captured by thiols was observed by alchemists, hence the name "mercaptan"). But there are also various glutathione specific enzymes, especially the GSH-transferases, that greatly enhance the detoxification properties of glutathione.

The GSH-transferase enzymes bind electrophilic substances to glutathione molecules, which are then excreted from the cell (and ultimately from the body). In some instances an electrophilic center was previously introduced by another reaction, such as those catalyzed by the cytochrome P-450 "phase I detoxification" enzymes. The subsequent conjugation of the now electrophilic molecule to glutathione is "phase II" of the detoxification system.

The resulting conjugate may also be toxic, but it can be more readily excreted than the original molecule. This is especially the case for hydrophobic compounds (which could otherwise accumulate in cells) because the conjugates (being water soluble) are more easily transported to the liver and kidneys by the circulatory system.

Cell walls use a special transport system (the "GS-X pump") that can excrete via exocytosis (QP606.G59G59:199) any glutathione conjugate with a molecular weight over ~350 (GSH itself has an MW of 307 Daltons). This constitutes the "phase III" of the detoxification system. Glutathione chelate complexes of metals (e.g. arsenic) are also excreted by the GS-X pump. The GS-X pump has been extensively studied due to its role in the detoxification of various antitumor chemotherapeutic drugs, such as Cisplatin (QP606.G59G59:199). Tumor cells with increased expression of the GS-X pump are termed "multidrug resistant".

Glutathione is also a required coenzyme for other detoxification processes, including the methylation of arsenic. Insufficient GSH (e.g. from depletion due to alcohol consumption) is responsible for acetaminophen toxicity, which is the second largest class of toxic drug ingestions in the United States (BMCCC6:155).

Because exposure to toxins is normally rare, people with glutathione deficiency can seem well nourished (until exposed to a toxic substance). However, in regions where there is chronic exposure to toxins, such as arsenic contaminated well water (EHP112:1104), toxicity correlates inversely with low consumption of animal protein, the most significant dietary precursor of glutathione.

4.5 Glutathione and/or Cysteine Deficiency.

4.5.1 Dietary Sources Glutathione, Cysteine, Methionine, and Taurine

Cysteine deficiency may be common even in people who eat "enough" protein. Many sources of dietary protein have low content of cysteine and methionine (another amino acid that can be converted to cysteine in vivo). People who don't eat much animal protein are at risk because most other foods have low content of sulfur amino acids (SAA=cysteine, cystine, methionine, and taurine).

The Nutrients Catalog (QP141.N48:249) lists the amino acid contents of a wide variety of food sources. The cysteine content of animal tissue protein sources, seeds and some types of legumes and nuts tend to range from ~40 mg/kg (fried chicken) down to ~20 mg/kg (beef lunch meat). Cereals (corn flakes, wheat flakes, shredded wheat) have ~20 mg/kg. Cheeses, evaporated milk, tofu, and some types of beans and nuts tend to be in the range of 12 mg/kg down to 4 mg/kg. Fruits and vegetables tend to be in the range of 3 mg/kg down to 1 mg/kg. Beverages, foods with a high water content, some processed foods, and some fruits have less than 1 mg/kg (e.g. orange juice, watermelon, cucumbers, pumpkin, canned carrots, and apples). As a rule of thumb, animal protein has 10× the cysteine content of fruits and vegetables, with cheeses and legumes in between.

In 2001, it was reported that the current recommendations for daily dietary sulfur amino acid (cysteine+methionine) consumption were low by almost a factor of two (13 mg/kg instead of 25 mg/kg) due to an arithmetic error when the requirements were determined experimentally in 1955 (AJCN74:756). Another problem with the way that dietary cysteine+methionine requirements were determined is that the experiments were based on "nitrogen balance" which only measures the amount of the amino acid that is needed for protein formation (weight maintenance) and does not take into account other biological requirements for cysteine (such as glutathione synthesis and taurine synthesis).

The need for dietary sulfur amino acid consumption continues to receive little emphasis in dietary recommendations, and in the opinion of the present inventor, it is much too easy for people who think that they are eating well to actually not be consuming enough SAA. Regarding dietary protein, the newly published "Dietary Guidelines for Americans 2005" (www.healthierus.gov/dietaryguidelines) states that "most Americans are already consuming enough. . . . As such, protein consumption, while important for nutritional adequacy, is not a focus of this document."

Their recommendations for fruits, vegetables, and other nutrients seem reasonable in most respects, but what percentage of the American population will actually consume 3 cups of milk a day? And what about those who don't? Those who avoid milk consumption are specifically recommended to find other sources rich in calcium, potassium, magnesium, zinc, iron, riboflavin, vitamin A, folate, and vitamin D, but protein is not mentioned in the list. In the section on "Vegetarian Choices", it is stated that "½ ounce of nuts or ¼ cup of legumes is considered equivalent to 1 ounce of meat, poultry or fish", which is correct in terms of total protein content, but does not take into account that the bioavailable content of SAA in nuts and legumes can be very low (or even negative, see below). Glutathione in food varies dramatically, such that well fed Americans can have a 40:1 range in its consumption (JFCA2:327). However, dietary glutathione probably has no special significance other than as a source of cysteine. The glutathione inside cells is created from its constituent amino acids (glutamic acid, cysteine, and glycine). Of these, cysteine is almost always the limiting amino acid, because glutamic acid and glycine are relatively common in foods.

Dietary taurine comes exclusively from animal sources (there is no taurine in plants), but the body can produce taurine if necessary from excess cysteine. In other words, without enough taurine consumption, or extra cysteine consumption (beyond the requirements for protein and glutathione synthesis), taurine deficiency can occur. One effect of taurine deficiency is impaired cholesterol metabolism, which can lead to cardiovascular disease (AMR6:78).

A particularly good source of dietary cysteine is whey protein, which has been shown to increase glutathione levels, with a wide variety of associated health benefits (U.S. Pat. No. 5,451,412A, www.glutathione.com). It has also been claimed that the undenatured cystine in whey protein is more bioavailable than other dietary sources of cysteine (U.S. Pat. No. 5,451,412A).

Dietary alliums are a good source of cysteine, but their unpleasant side effects when consumed in other than small quantities limit their ability to serve as a primary source of cysteine. But *allium* related compounds (e.g. garlic) can partially compensate for cysteine deficiency, both by providing biothiols and by increasing the effectiveness of glutathione. For example, dietary garlic or onion powder has been shown to increase the liver glutathione level in chickens by 40% (RM666.G15K6313, page 190). And administration of SAMC has been shown to significantly increase the total glutathione level of cells (CR61:725). Consumption of garlic produces an increase in the reduced glutathione level by increasing the activity of the GSH reductase enzyme by up to 87% (RM666.G15K6313, page 190), thereby increasing the proportion of GSH to GSSG.

4.5.2 Cysteine Degradation from Food Processing and Cooking.

While whey protein is an excellent source of cysteine, its bioavailable cysteine is very sensitive to denaturation from heat or mechanical shock, requiring a microfiltration process to be used during its manufacture. If not prevented, this denaturation causes a significant decrease in the ability of whey protein to raise the glutathione level (U.S. Pat. No. 5,451, 412A).

The sulfhydryl and disulfide groups of proteins (i.e. the cysteine and cystine) are the most vulnerable amino acids to food processing, and have been shown to be easily damaged by heat during cooking. Heating above 30 degrees C. causes the progressive denaturation of cystine, and heating above 70 degrees C. causes the progressive irreversible destruction of cysteine (N207:1269). Interestingly, although cooking increases the digestibility of protein in general, the damage to the cysteine can lower the net protein quality of cooked food.

Foods are treated with heat and alkali for many purposes such as to sterilize/pasteurize, to improve flavor or texture, to destroy toxic or anti-nutritional factors, to promote desirable physical properties, and to solubilize proteins (R850.A1A3V459:161). The formation of lysinoalanine (LAL) mainly via the reaction between the lysine and cysteine residues that occurs during heat treatment in the presence of alkaline not only results in cysteine loss, but the LAL itself is toxic and can cause kidney damage. Experimentally, the alkaline treatment with 0.1N NaOH at room temperature for 1 hour followed by heat treatment at 75 degrees C. for 3 hours and then neutralization with 10N HCl resulted in the loss of 20% of the lysine and 75% of the cysteine, along with the HPLC detectable formation of LAL (R850.A1A3V459: 161). The anti-nutritional factors formed during alkaline/heat treatment also caused a reduction of weight gain of rats of 25% compared to those fed untreated diets (R850.A1A3V459:161).

Other chemical treatments of foods that affect the cysteine content include browning (e.g. the Maillard reaction), acetylation, and glycosylation. The sulfhydryl and disulfide groups of proteins are also the most easily damaged components of food from anti-microbial radiation treatment.

4.5.3 Anti-Nutritional Foods 4.5.3.1 Foods that Inhibit Digestive Enzymes

Legumes, especially soy beans, inhibit digestive enzymes so much that they not only have poor digestibility themselves but they also reduce the digestion of other proteins being consumed in the same meal unless the enzyme inhibitors are completely deactivated (TP453.P7F68:281). The digestive enzymes that are secreted by the digestive system are rich in cysteine and are normally "recycled" (i.e. digested) along with the food, but the inhibitors in legumes prevent these enzymes from being successfully digested and reabsorbed, so there can be a net cysteine loss from the digestive process itself. Therefore, protease inhibitors and lectins in raw soybean meal are found to be anti-nutritional (they cause weight loss when consumed along with other food).

Most commercially available soy flours have been heat treated but still retain 5-20% of the original inhibitor activity because more heat treatment would cause excessive damage to the nutritive value of soy proteins (in addition to the cysteine loss that has already occurred due to even the lesser amount of heat treatment).

Supplementation with cysteine or NAC prior to heat treatment deactivates the enzyme inhibitors more than the heat treatment alone, allowing a lower temperature to be used and providing some cysteine supplementation. For example, adding cysteine (2% by weight) and then heating the soy flour at 65 degrees C. for 1 hour deactivates the trypsin enzyme inhibitor by over 90%, improving the protein efficiency ratio (PER) by a factor of 2.43 (JN114:2241). Much of this PER improvement is presumably due to the cysteine supplementation, given that cysteine is typically the limiting amino acid in soy flour.

Experiments with rats show that when added to a casein (milk protein) diet, beans decrease growth, diet efficiency, protein digestibility and protein utilization. Although heat treatment (to deactivate the inhibitors) improved the nutritional value of the mixed bean-casein diet, the values were still lower that a diet of 10% casein alone (TP453.P7F68: 281).

4.5.3.2 Unbalanced or Excessive Amino Acid Consumption

Unbalanced amino acid concentrations can cause a variety of anti-nutritive conditions. As an interesting side note, although rice and black beans are each unbalanced protein sources individually, they complement each other and can form a well balanced source of protein when consumed together. However, the protein content of rice is low (5-7% by weight) compared to most other cereals (TP453.P7F68:281).

Even at the cellular level, an unbalanced amino acid concentration can cause pathology. Because cystine and glutamate share the same membrane transport system (RB170.O96:285), glutamate competitively inhibits the cellular uptake of cystine (QP552.G58G54:407). An imbalance between extracellular glutamate and cystine is implicated in the lethality of lung cancer (RB170.O96:285), the pathology of AIDS (RB170.O96:285) and the progression of aging (ARR1:257).

4.5.3.3 Unbalanced or Excessive Vitamin Consumption

Although vitamin C and glutathione in many ways work together, excessive vitamin C consumption has been shown to significantly decrease the glutathione content of cells. This effect has been utilized in a clinical trial where the goal was to increase the cytotoxicity of the chemotherapeutic drug arsenic trioxide (which is normally detoxified by glutathione within cells) against the cancer multiple myeloma (CCR8: 3658). A daily dosage of 1000 mg of vitamin C caused significant glutathione depletion, resulting in a mean percentage decrease of 60% among the patients.

An example of the toxicity of unbalanced vitamin consumption relative to other nutrients is that although vitamin E and cysteine when administered together in rats prevent the development of "fatty liver" from excessive alcohol consumption, vitamin E by itself appears to sensitizes the rats to liver damage (QP551.B27:227). This indicates that in the presence of cysteine deficiency (a common problem with alcoholics), the intake of vitamin E may need to be reduced relative to the normal dietary amount (or their alcohol consumption should be reduced instead, if possible).

4.5.4 Intense Delivery of Cysteine

Normally, the primary source of cysteine is dietary protein, but in some cases it is desirable to supply more cysteine than can reasonably be supplied through the consumption of protein. For example, the standard treatment for acetaminophen poisoning (which causes severe glutathione depletion) is the oral administration of N-acetylcysteine (NAC) (BMCCC6: 155). Of necessity, the NAC dosage is high (an initial dose of 140 mg/kg (9800 mg for a 70 kg person), followed by 17 doses of 70 mg/kg every 4 hours). The low toxicity of NAC, combined with its rapid conversion to cysteine (which in turn is rapidly converted to glutathione inside liver cells) is important for this application.

SAMC is another compound that has been studied as a means to deliver cysteine. In vitro experiments show that when cells are administered SAMC (which contains a cysteinyl radical that can easily be converted to cysteine in vivo), the result is a significant increases the total glutathione level of cells (CR61:725). Pretreatment with SAMC has been shown to protect mice from acetaminophen poisoning, by suppressing the reduction in hepatic glutathione level after acetaminophen administration (PHYRES3:50). Post treatment with a single dose of SAMC (200 mg/kg) shortly after exposure to acetaminophen is also protective in mice (EJP433:177). Similar results were obtained in PHYRES3: 50, which shows that SAMC is much more effective than the other garlic related compounds contained in the "AGE" (Aged Garlic Extract) dietary supplement.

4.6 Thiol-Disulfide Exchange Reactions

Thiol-disulfide exchange reactions are a unique feature of organosulfur chemistry that provide a rapid, reversible, energy-neutral, highly specific covalent reaction for the bonding together (or the separating) of molecules that incorporate a thiol or a disulfide bond (QP551.T6913:54, QD305.S3C48:633).

The present inventor notes that more properly, this type of reaction should have been named the "thiolate-disulfide exchange reaction", because it always involves the ionized version of the thiol (RS⁻). If the disulfide is represented as R'SSR" the exchange is as follows:

In other words, the ion and the disulfide form a temporary complex with three interreacting sulfur atoms (and an electron), which soon separates with the resulting thiolate ion coming from any of the three thiyl radicals and the remaining disulfide molecule consisting of the other two thiyl radicals.

Like other thiol anions, the ionized form of reduced glutathione (GS⁻), will readily participate in thiol-disulfide exchange reactions with disulfides (oxidized thiols), reducing half of the disulfide in the process (QP552.G58G54:73). The resulting oxidized glutathione (either GSSG or RSSG depending on whether the other reactant contained glutathione) can it turn react with other thiol anions (R'S⁻) in further exchange reactions, becoming either GSSG, R'SSG, or GS⁻ depending on the nature of the other reactant and how they separate.

Of course, this brief description is somewhat of an oversimplification. Exchange reactions can be subject to steric constraints. And the products of the reaction depend on the relative redox potentials of the three thiyl radicals involved. But typically, the reaction is rapid and the product mix is random, resulting in the formation of every possible mixed disulfide (and every possible thiolate ion).

Thiol-disulfide reactions are important in the formation of the Cysteine to Cysteine bridges within proteins that help determine and stabilize the tertiary structure of the protein. They also are involved in the formation of Cysteine to Cysteine cross-links between proteins.

Many enzymes have an "SH" group at their active site (BIJ63:514), and their activity depends on whether this remains an exposed thiol (or an exposed thiolate ion), with the enzyme inactive if the thiol is "blocked" by an attached thiyl radical. This leads to the "redox regulation" of enzymes, which is considered to be an important mechanism for regulation, signaling, and control. Note that the inactivation of the enzyme is non-destructive, because a new thiol-disulfide exchange reaction between the blocked site and any thiolate ion that happens to float by can result in a disulfide floating away (leaving the SH group on the enzyme as a thiolate ion), and the enzyme becomes active again.

The majority of the organosulfur compounds that are discussed within this patent are thiols or disulfides, so exchange reactions are very relevant to their associated chemistry.

5. SUMMARY OF THE INVENTION

The present invention provides comestible compositions in the form of nutraceutical and dietary supplement formulations and methods for producing and administering such formulations having certain health or medicinal benefits. More particularly, the methods and formulations of the invention provide a compound or prodrug comprising certain organosulfur radicals, such as the allyl mercapto radical, bound to larger molecules such as proteins, resulting in the formation in the host's body of various *allium*-related compounds such as allicin. The use of bound organosulfur radicals avoids a variety of difficulties associated with alternative forms of administration of other *allium*-related compounds such as garlic, onions, or prior art dietary supplements such as garlic capsules.

The formulations of the present invention are suitable for continuous preventive use in either nutraceutical form or as a dietary supplement, providing general health benefits while offering some protection from various potential diseases. A higher dosage can be utilized when increased protection is desired, for example, in the event of exposure to an infectious disease, or during travel that could involve such exposure, or during low-level exposure to an environmental toxicant, or for the treatment of a chronic disease. A still higher dosage can be used for the treatment of an acute disease.

Particular embodiments are disclosed that are "low tech" in that they utilize inexpensive ingredients and a simple manufacturing process, allowing their widespread manufacture and use by economically disadvantaged groups.

Experiments with the resulting compounds have led to the discovery of several novel antioxidant and localized oxidant effects, including the coupling of extracellular antioxidants to the intracellular GSH reductase system and the localized formation of allicin from the oxidation of allylSH and/or DADS.

Other aspects, advantages, and novel features of the invention are described below or will be readily apparent to those skilled in the art from the following specifications and drawings of illustrative embodiments.

6. BRIEF DESCRIPTION OF THE DRAWINGS

7. DETAILED DESCRIPTION OF ILLUSTRATIVE EMBODIMENTS

Figure 1:
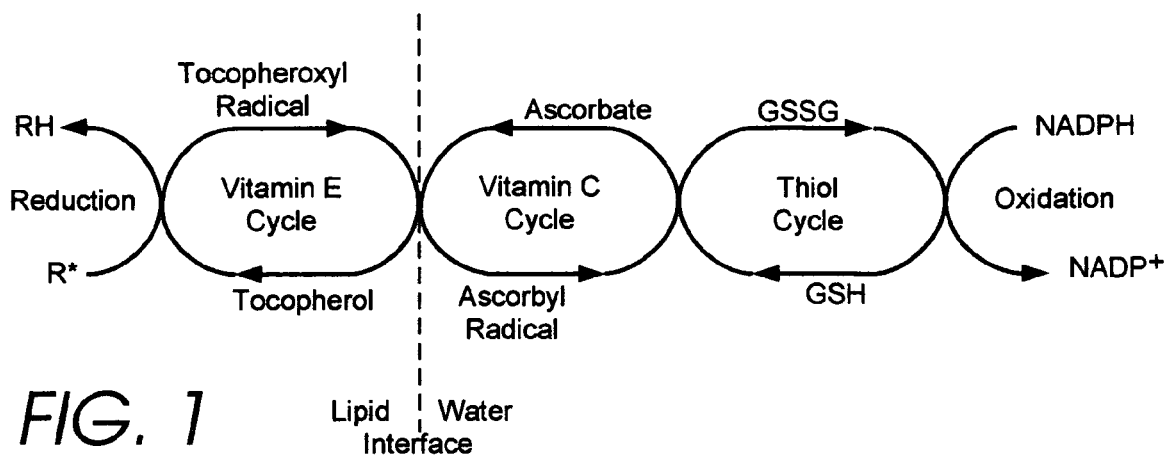
FIG. 1 is a diagram of the antioxidant network illustrating the participation of glutathione in the thiol cycle.

For a better understanding of the nature and functioning of the invention, it is instructive to relate here the historical development of the invention.

7.1 In Search of Bioavailable Allicin

An effort was undertaken to learn as much as possible about allyl mercaptan (AllylSH), given its apparent central role in the metabolism of various garlic related compounds. An initial investigation, including various web searches, yielded interesting results:

First, Allyl mercaptan is commercially available as an FDA approved food additive. It is classified as "Generally Recognized As Safe" (GRAS) for use as a flavoring agent. It is even available in "Kosher" form. Second, it has a stench that only a skunk could envy. I decided to order some, but to also investigate other alternatives.

It is well established that allicin reacts instantly with cysteine (PM59:A688). Similarly, allicin was found to react instantly with glutathione to form S-Allylmercaptoglutathione (SAMG, AllylSSG) (BBA1463:20, WO:01/36450). The resulting product is a mixed disulfide with an allylmercapto radical disulfide bonded to the cysteinyl radical of the glutathione. This is analogous to the bonding of allyl mercaptan with cysteine (forming SAMC) but in this case the cysteine is part of a glutathione molecule. SAMG has been shown to share many of the medicinal properties of allicin (WO:01/36450).

At the local GNC store, I bought "L-glutathione 50" tablets, "L-Cysteine 500" tablets, and "N-acetyl-L-cysteine 600" tablets. I quickly learned that I could get 500 mg of cysteine for about the same price as 50 mg of glutathione. I became interested in SAMC as a less expensive alternative to SAMG.

I did some "kitchen experiments" on the formation of SAMC and SAMG from ground-up tablets mixed with liquid allicin (from Allicin International, www.allimax.com). I also dissolved Allimax tablets to use as a source of allicin. And I used garlic power mixed with water as a natural source of allicin. The experiments showed that:

When the Allimax tablets are dissolved in water, they have a strong taste and there was a burning sensation in the mouth and stomach, similar to that obtained when garlic powder is dissolved in water (forming allicin).

The taste of the dissolved Allimax was greatly reduced by adding ground cysteine or glutathione, and the burning sensation was eliminated.

When using garlic powder or liquid allicin, the taste after adding ground cysteine or glutathione was still unpleasant.

Another realization that reinforced my decision to use cysteine along with allyl mercaptan was that consumption of allyl mercaptan by itself would form SAMC when exposed to free cysteine, which would decrease the amount of free cysteine available. Due to the importance of cysteine, even this temporary depletion was considered undesirable, especially if a significant dosage of allyl mercaptan was being used for the treatment of a disease. By using cysteine along with the allyl mercaptan, there is an equal supply of cysteine along with the allyl mercaptan being supplied, preventing depletion.

I was able to re-dry the "Allimax with cysteine" mixture in a non-stick baking pan. After grinding, the resulting powder could be put into capsules. The "SAMC Capsule" was born.

Meanwhile, the allyl mercaptan that I had ordered had arrived.

7.1.1 Experiments with Nutraceutical Formulations

I wanted to develop some nutraceutical formulations, so I started experimenting with beverage formulations.

In the context of the present invention, a nutraceutical is defined as being a fortified food (including beverages as well as solid foods) that is held to provide health or medical benefits (e.g. the prevention of a chronic condition or the cure of a disease) in addition to its basic nutritional value. The key points are first, that it is fortified (e.g. has contents beyond that contained in normal formulations of the food), secondly, that its medicinal properties are presented as a feature by the manufacturer and are perceived as a benefit by the consumer, and thirdly, that it can be consumed as a food according to its nutritional value (without the possibility of an overdose, regardless of the amount consumed for nutritional purposes).

Initially, my goal was to have the allyl mercaptan combine with something in the beverage (presumably cysteine) because I wanted to see if the bound form would have less "garlic" taste and smell. I knew that many proteins contain cysteine, and that in many cases these have the exposed "SH" groups that have the potential to form disulfide bonds with the allyl mercaptan. Similarly, the allyl mercaptan could form a bond to half of a cystine (cysteine disulfide) via a thiol-disulfide exchange reaction, and then additional allyl mercaptan molecules could disulfide bond to the newly exposed cysteine residues.

I researched the amino acid content of various foods to find those that were high in cysteine content, but did not restrict my experiments to these.

When I noticed that potatoes have a reasonable cysteine content, my wife and I made some hash-browned potatoes, marinating the shredded potatoes in diluted allyl mercaptan before cooking. The results tasted good (just like normal hash browns—although some more garlic flavor would have been nice).

For a standard dosage, I decided to first dilute the allyl mercaptan by a factor of 400 (to get the smell down to where I could bring it into the house), which gave a concentration of approximately 10 mg of allyl mercaptan per teaspoon (the equivalent of a single large clove of garlic's thioallyl potential).

I would add a teaspoon for every 8 oz of beverage into the bottle, shake it, and let it sit overnight in the refrigerator, taste testing it the next day. Many of the beverages had no objectionable "garlic" taste (listed in the order tested):

LOOZA Pear Nectar
Kern's All Nectar Strawberry Banana (which became a favorite of mine)
V8 Juice
Knudsen Organic Pear
Campbell's Tomato Juice
TAXO Lemon Ginger (a real favorite)
Dole Orange Peach Mango
Knudsen Pineapple Coconut
Kern's Strawberry Banana
Starbuck's Frappuchino
Earl Grey Tea with Lemon and Honey
Boylan Ginger Ale
Boylan Root Beer
SoBe Tsunami Orange Cream
SoBe Lizzard Lightning
Red Bull Energy Drink
Hansen's Energy Original Formula
Hansen's Energy Power Formula
Red Bull Sugar Free
Tropicana Mixed Berry Smoothie
Albertson's Apple Juice
LOOZA Peach
LOOZA Banana Nectar
LOOZA Mango Nectar
SoBe Power
Andronico's Natural Apple Juice (another favorite)
SoBe Energy
SoBe Nirvana
LOOZA Pear Nectar
Kern's Guava
Walnut Acres Organic Apple Juice
Nana Mae's Mid-season Apple Juice
Nana Mae's Gravensten Apple Juice
Nana Mae's Pear Juice
Kern's All Nectar Guava
Low fat milk
Stash Licorice Spice herbal tea There were also beverages with slight but objectionable garlic taste:

Fresh Squeezed Watermelon
Kern's All Nectar Apricot
TAZO Lemon Green
TAZO Enlightened Lemon Tea
TAZO Mango
Santa Cruz Berry Nectar
Knudsen Orange Mango Beverages with strongly objectionable taste were also observed:

Ocean Spray Cranberry Juice Blend
Fresh squeezed grapefruit juice
Fresh squeezed orange juice
Honey with Apple Cider Vinegar
Coca Cola Beverages that were indigestible:

Ocean Spray Ruby Red Grapefruit Blend
AW Root Beer

I also experimented with teas by soaking the leaves in a $\frac{1}{200}$ dilution of allyl mercaptan, then spreading the moist tea leaves out thinly on drying trays. Excellent results were obtained with:

The Tao of Tea Green Earl Grey
The Republic of Tea Orange Ginger Mint

One observation was that every beverage that contained ginger tasted great. Because ginger is a medicinal that is frequently used with garlic (ISBN9679786846), I decided to pre-mix 300 ml of $\frac{1}{400}$ allyl mercaptan with 6 teaspoons of ginger powder and use this liquid (which I called "fire water") as an additive to beverages. Adding 1 teaspoon of this for each 8 ounce serving in a bottle of Andronico's Natural Apple Juice produced a beverage that I and various taste testers agreed tasted better than the original. I liked it so well that I never got around to experimenting with other "fire water" augmented beverages (see below).

The theoretical maximum amount of allyl mercaptan per 8 oz serving is calculated to be:

$$\frac{1}{400} \times 5 \text{ ml (per teaspoon)} \times 0.925 \text{ g/ml (weight of AllylSH)} = 11.56 \text{ mg}$$

Further research into the metabolism of garlic-related compounds revealed that there are "monoxidase" enzymes in liver cells (and various other cell types) that can convert diallyl disulfide to allicin in vivo. Because diallyl disulfide is easily formed from allyl mercaptan (it is its disulfide form), this means that the allyl mercaptan that is consumed could end up producing allicin in the body. (See also section 4.2.5.3 above).

I found a company (Plant Bioactives Research, Orem Utah) that offers commercially the service of performing an "Allicin Bioavailability" assay of garlic related dietary supplements. I sent a sample of the apple-garlic-ginger beverage to them for testing.

The test involved having a "calibrated individual" consume the product and to analyze the individual's breath periodically over the period that it takes for the response from the product to disappear. The metabolite being measured is AllylMethyl-Sulfide (AMS), a compound whose total volume in the breath has been shown to be proportional to the allicin-equivalent thioallyl content of a variety of garlic-related compounds, including allicin, diallyl disulfide, allyl mercaptan, and SAMC. Thus, the test could more accurately be described as an "allicin bioequivalence" assay, given that no actual allicin need be involved.

Figure 2:
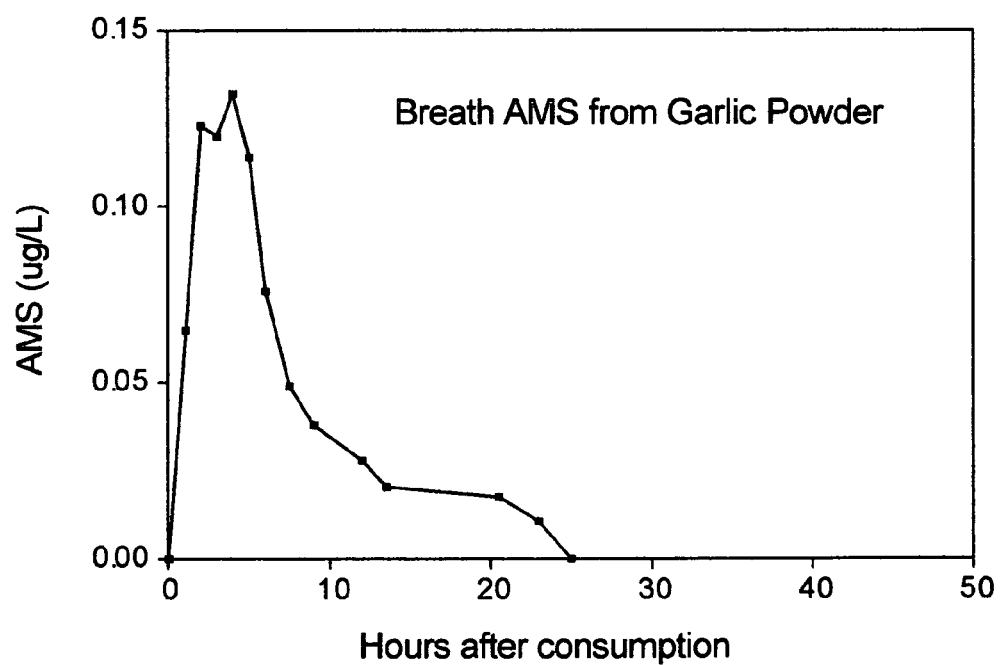
FIG. 2 is a graph showing the time profile of bioavailable allicin (as indicated by AMS in breath) provided by the prior art (garlic powder).

For example, FIG. 2 plots the AMS produced from ingesting wet garlic powder with an allicin content of 9 mg. Because the allicin was produced when the water was added to the powder (just before its consumption), the AMS starts showing up in the breath very quickly. The AMS level has a relatively constant peak from hours 2 to 5, declines rapidly to less than $\frac{1}{3}$ of the peak by hour 8, and then further declines at a reduced rate until it becomes undetectable at hour 25. (Consuming wet garlic powder in its pure form is painful because of its strong taste and the burning sensation it causes in the mouth and stomach. Its concentrated use is not recommended.)

Figure 3:
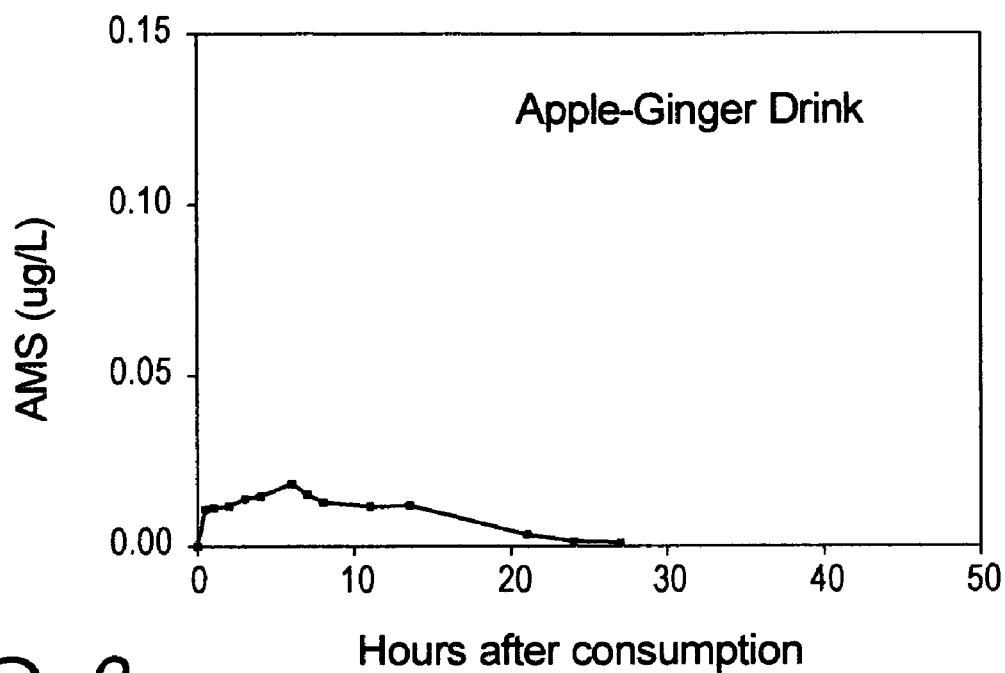
FIG. 3 is a graph showing the time profile of bioavailable allicin from an apple-ginger drink that is formulated to provide protein-bound SAMC.

In some ways the results for the apple-ginger beverage (shown in FIG. 3) were as I expected: significant AMS was detected, And the rate of AMS generation over time was much more uniform than the rate of AMS formation from ingested wet garlic powder (see FIG. 2). This is presumed to be because the *allium*-related compounds that result in AMS formation are released from the protein and further metabolized more gradually than the wet garlic powder was. The uniformity of AMS generation over time is excellent.

Unfortunately, the total volume of AMS was only about $\frac{1}{10}$ of the amount that would be expected from the amount of SAMC that I had intended to be produced. The area under the curve in FIG. 2 corresponds to that which would be obtained from approximately 1 mg of allicin from wet garlic powder, not 11.56 mg. The reason for this discrepancy was not determined at the time, but I suspected that it was related to how well the allyl mercaptan combined with the ginger. Perhaps it was not being released from the ginger during digestion as well as I had expected. If an undigested garlic-ginger compound is being excreted, the benefit of using ginger as an additive is dubious.

Figure 4:
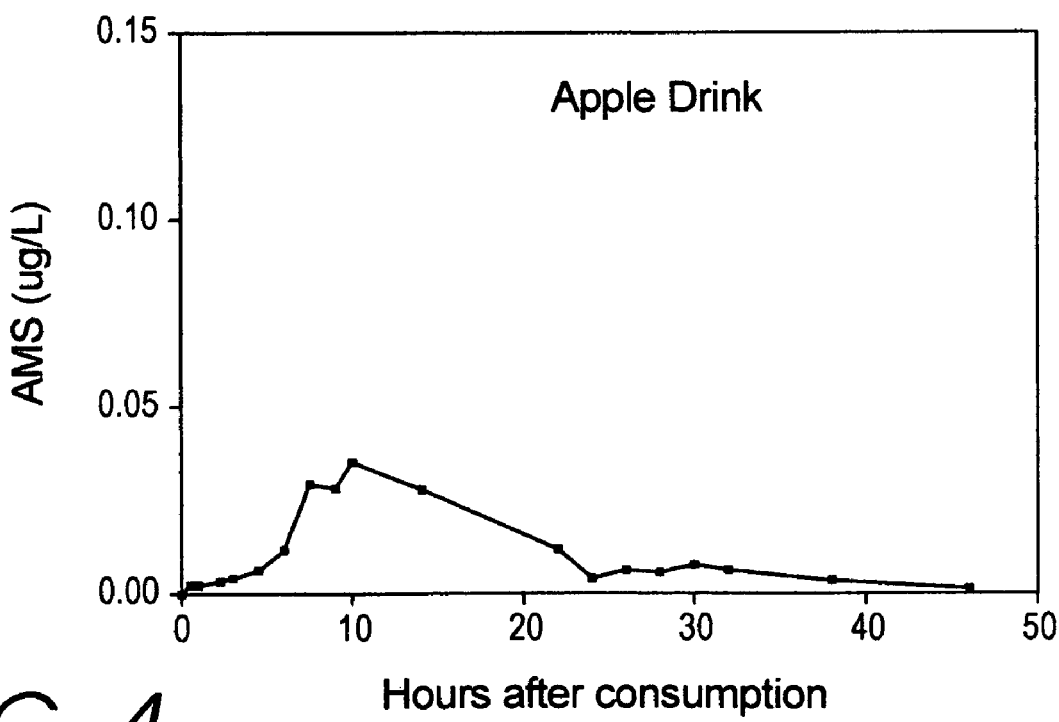
FIG. 4 is a graph showing the time profile of bioavailable allicin from an apple drink that is formulated to provide protein-bound SAMC.

So I made another apple juice beverage that omitted the ginger powder from the formulation. When tested (FIG. 4), it produced over twice the amount of AMS, indicating that I was now getting about $\frac{1}{5}$ of the expected amount. Now the area under the curve corresponds to that which would be obtained from approximately 2.8 mg of allicin from wet garlic powder. That represented significant progress, so I decided not to concentrate my effort on apple-ginger anymore.

Figure 5:
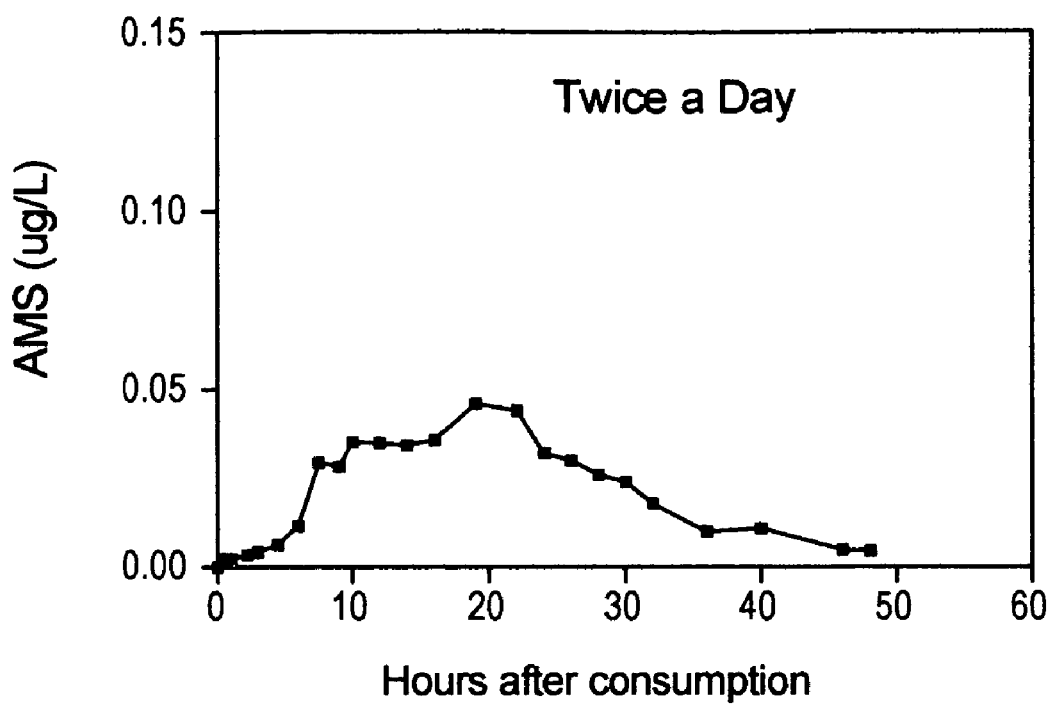
FIG. 5 is a graph showing a superposition of the time profile of bioavailable allicin for the apple drink consumed twice a day.

Interestingly, there was a significant delay before a steep rise to the peak, which I interpret as an indication that the allyl mercaptan was covalently bonded (e.g. disulfide bonded to cysteine) and was released late in the digestive process (presumably as SAMC). The duration of significant AMS response was from approximately hour 6 to hour 23. This raised the question of how uniform a response would be obtained from consumption twice a day (say at 8 AM and at 6 PM) so another plot of the data was made showing the superposition of two doses spaced by 10 hours (FIG. 5). The predicted response is reasonably uniform from hour 6 to hour 32 (more than 24 hours of duration).

Perhaps the low amount of AMS can be attributed to the difference in the digestive and/or metabolic pathway between protein-bound SAMC and the other (non-bound) *allium*-related compounds. The actual metabolic pathway that results in AMS generation has not been determined (JAFC53:1974), so this is a real possibility. To the best of my knowledge, the formulated allylmercapto groups remain in the product up to the point of consumption. The protein-bound SAMC could be being fully metabolized by a path that happens to produce less AMS, so I was hesitant to compensate for the low assay by just increasing the active ingredient concentration at this time.

Another consideration is that the food grade allyl mercaptan is likely to have a concentration of allyl mercaptan in the 50% range or below. Even the technical grade allyl mercaptan that is commercially available (e.g. product 06030 from Sigma-Aldrich) is only specified to contain ~60% allyl mercaptan (with the impurities expected to be primarily other allyl sulfides, such as diallyl sulfide, which are breakdown products of allyl mercaptan). The implication is that ideally the production of the allyl mercaptan would immediately precede the production of the beverage, but this was not practical for me to do.

In any case, sufficient bioavailability had now been shown to prove that protein-bound SAMC can metabolize into the thioallyl compounds that produce a breath AMS response.

I had observed that the beverage taste results did not always correspond with the published cysteine content of the various foods. For example, apple juice would be expected to do worse than orange juice, because apples have only 3 mg per 100 grams of food, but oranges have 11 mg/100 g (NC1993). But the "natural" apple juice did much better than fresh squeezed orange juice.

The pH sensitivity of the reaction rate of thiol-disulfide exchange reactions could explain why the more acidic beverages seem to do poorly. In this case, waiting a longer time (or creating a temporary shift in the pH to speed up the reaction) could result in the desired disulfide bond formation. Alternatively, the vitamin C could be "reducing" the disulfide bonds, resulting in less disulfide bound allylSH than would otherwise be formed. But I decided not to get distracted by "debugging" the acidic beverages at this time. (I had enough other beverages that worked well enough for now.)

7.1.2 Experiments with Dietary Supplement Formulations

Leaving nutraceuticals aside, I concentrated more on the development of dietary supplements, such as capsules, which needed to be more concentrated because they need to be much smaller. But I still wanted to use normal food proteins, if possible.

In the context of the present invention, a dietary supplement is defined as a product consisting of one or more ingestible substances that is held to provide health or medical benefits (e.g. the prevention of a chronic condition or the cure of a disease), such substance(s) being deemed as not being present in sufficient quantity in the consumer's unsupplemented diet. The key points are first, that it has ingestible contents beyond those contained in the unsupplemented diet, secondly, that its consumption involves a conscious act by the consumer, and thirdly, that the amount of consumption is known and can be controlled by the consumer (thereby avoiding the possibility of an overdose by conscious consideration of the amount being consumed).

Another experiment using cysteine from capsules showed that allyl mercaptan did not combine with cysteine as well as the Allimax capsules did (there was too much residual garlic taste).

I realized that I really wanted to combine the allyl mercaptan with cystine (cysteine disulfide) instead of cysteine, because thiol-disulfide exchange reactions involve both a thiol and a disulfide (not two thiols). The Allimax tablets worked well because the allicin behaved like a disulfide in this respect, reacting with the thiol (cysteine). But allyl mercaptan is a thiol, so it does not react with cysteine (another thiol), but it should react quickly with cysteine disulfide (cystine) via a thiol-disulfide exchange reaction. (With time, in the presence of oxygen, two thiols will oxidize and form a mixed disulfide, but I was worried that evaporation of the allyl mercaptan could be more rapid than this oxidation, lowering the concentration.)

Researching for good sources of cystine (vs. cysteine) was tricky because most publications do not distinguish between the two. But there are a series of patents on undenatured whey protein (e.g. U.S. Pat. No. 5,451,412) that point out that whey protein is perhaps the best dietary source for cystine. ("Denatured" proteins typically have broken disulfide bonds, no longer connecting the cysteines that would normally have been disulfide bonded together). Special low temperature processing is needed to preserve the bonds for the undenatured product. They claim that even mechanical stress can damage the bonds (don't drop it!).

Further research revealed that apple juice can also be a good source of cystine, as indicated by its vulnerability to protein denaturation during processing (JAFC44:3413). The source of the large amount of protein damage detected in the JAFC44:3414 reference was largely due to the loss of disulfide bonds between cysteines, so there must have been a lot of them to start with. This may also explain why apple juice does better than some other juices.

I decided to do more experiments using whey protein. I purchased some from Immunocal (www.glutathione.com), and also some whey protein dietary supplement powders from a local supermarket.

I found that the whey protein was very effective in combining with allyl mercaptan, and that after only a few minutes the smell of allyl mercaptan was diminished to about the same level as the smell of milk. The mixture could then be mixed with anything else. But I was most interested in using this mixture to make dietary supplement tablets.

A rough calculation of the maximum amount of allyl mercaptan that can form protein-bound SAMC with a typical whey protein (e.g. from Jarrow Formulas, Los Angeles, Calif.) shows that because each gram of whey protein has 20.4 mg of cysteine (label information), and the ratio of the molecular weight of allyl mercaptan to cysteine is 74/121, the maximum is 12.5 mg of allyl mercaptan per gram of whey protein. In addition to this, some allyl mercaptan could be non-covalently bound to the protein, e.g. in the hydrophobic pocket located on the surface of each molecule of beta-lactoglobulin (TP453.P7F665:225).

Alternatively, the allyl mercaptan could penetrate the protein and become bound within the hydrophobic regions that are common within almost all proteins. Proteins can be remarkably permeable to small molecules (even water molecules can enter into the middle of a protein due to the fluctuations of the matrix) (QH506.D384:211).

A "Garlic" dietary supplement tablet was produced by hand mixing 3 tablespoons of whey powder with 1 tablespoon of garlic powder and 1 tablespoon of 1/10 dilution allyl mercaptan. The resulting paste was put into the small depressions in some plastic sheets (formerly the top portions of pill packaging that had aluminum "pop-out" backing), resulting in 150 tablets. After drying, the tablets were popped out of the plastic.

The resulting tablets had sharp edges, so I decided to put them inside gelatin capsules to prevent their scratching the throat during swallowing.

Figure 6:
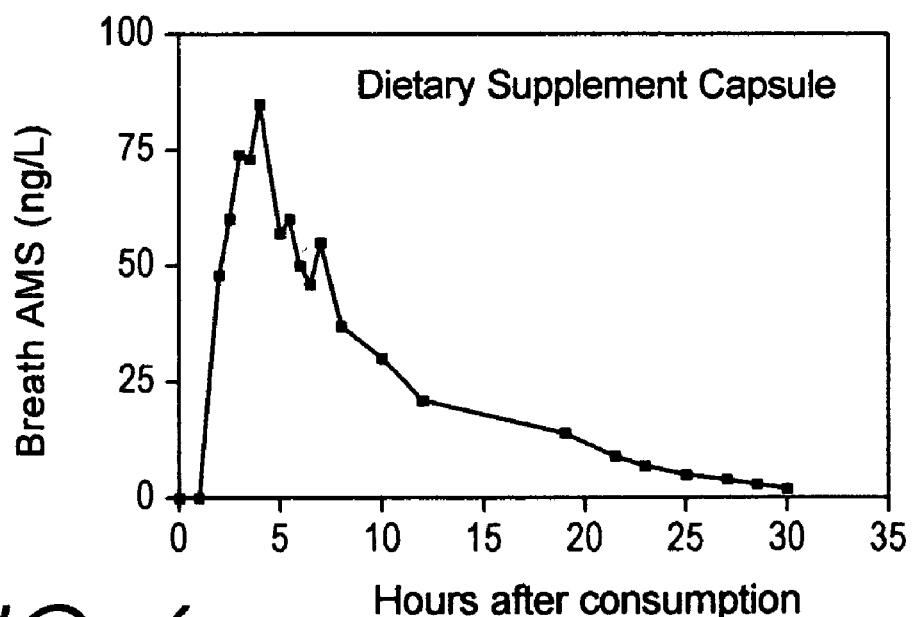
FIG. 6 is a graph showing the time profile of bioavailable allicin from a dietary supplement capsule that is formulated to provide protein-bound SAMC.

The capsules were then tested for their "bioavailable allicin" and the results (FIG. 6) were comparable to those obtained with the apple juice. I was now getting about 1/3 of the expected amount (1.6 mg out of an expected 5 mg for this formulation).

This performance is no worse than the performance achieved by most garlic dietary supplements in the past (JAFC49:2592). Of the 24 brands of enteric coated garlic powder tablets tested, their average allicin release was only 0.489 mg per capsule, which makes my 1.6 mg look pretty good. And the "AGE" product (which is well accepted) only has 2.14 mg/g of total sulfur compound content, of which only 0.14 mg is SAMC (RM666.G15K6313, page 104) Therefore a 100 mg AGE capsule would only have 0.21 mg of total sulfur compound and only 0.013 mg of SAMC.

My resulting whey-garlic-allyl-mercaptan product compares favorably with the dietary consumption of garlic and onions because many people do not like to consume them raw, and their medicinal benefit declines when they are cooked. (And even then, some people do not like cooked garlic and onions either.) The low cost and ease of manufacture of protein bound SAMC, coupled with the elimination of garlic's "side effects", makes the nutraceuticals or dietary supplements based on it a viable alternative. And it opens up the possibility of dosages that would not be practical from purely dietary sources of alliums.

Thus, it appeared I had an initial product, but the manufacturing process (or at least the determination of the appropriate "label claim" for dosage) could use improvement. One inconvenience was that the garlic powder that was used in the first batch of capsules made the mixture sticky and it was not easy to spread it uniformly in the drying pan. All subsequent capsule formulations omitted the garlic powder.

A "Nondisclosure and Product Evaluation Agreement" document was prepared to allow other people to evaluate these products and also some related products that are further described in my patent application entitled "Personal Care and Medicinal Applications of Products Incorporating Bound Organosulfur Groups" that is being filed contemporaneously herewith. Over twenty volunteers agreed to participate.

In order to quantify the amount of protein bound SAMC that was being formed in the capsules, samples were sent to IBC Labs (Tucson, Ariz.) for amino acid analysis. The analysis procedure that they use is based on AOAC protocol 982.30 (Association of Official Analytical Chemists International, Arlington, Va.), and utilizes the steps of acid hydrolysis to break down the proteins to their amino acid constituents followed by AQC derivatization and then HPLC analysis.

A reference sample of pure (>99%) SAMC was also provided, which allowed the HPLC equipment to be calibrated to allow the SAMC content of the protein to be analyzed in addition to the other amino acids. The location of the HPLC peak obtained from this substance was sufficiently distinct to allow it to be discriminated from the other amino acids in proteins.

The results of the amino acid analysis showed that the allyl mercaptan had become bound to the protein as SAMC, and this SAMC had been liberated by hydrolysis and produced a response identical to that of the SAMC reference sample. But, surprisingly, the measured amount of SAMC exceeded the calculated theoretical maximum amount. So some more experiments were performed, including reanalysis of the SAMC reference sample.

It turned out that the SAMC reference sample had originally been analyzed without including the hydrolysis step (the lab assumed that because it was being supplied as a reference this was not necessary). Reanalysis of the SAMC reference sample, using the same hydrolysis procedure that is used for the actual samples, produced a more reasonable result (7.6 mg/ml of SAMC measured, out of a 7.8 mg/ml calculated maximum, based on the amount allyl mercaptan that had been added to the whey protein). A literature search showed that other researchers had also had problems with incomplete hydrolysis of the calibration mixture leading to higher measured values of amino acid content (ANBC177: 318).

The results of the amino acid analysis also could imply that the normal digestive process (which includes the hydrolysis of proteins to amino acids in the acidic environment of the stomach) would produce SAMC molecules. Because ingested SAMC is known to be 100% bioavailable (JAFC53: 1974), the digested SAMC would also be expected to be 100% bioavailable.

Further investigation into the digestive process revealed the complexity involved in the hydrolysis of protein-bound SAMC and other aspects of its digestion. But the investigation into the digestive process, while educational, did not resolve why the measured "bioavailable allicin" value was lower than expected.

It turns out that the acid based hydrolysis in the stomach is less complete than that of the AOAC protocol, primarily because it is at body temperature and is only in the stomach for a few hours, but the AOAC protocol specifies a temperature of 110 degrees C. and a duration of 24 hours.

In mammals, most of the hydrolysis of proteins is performed by peptidase enzymes, and the enzymes in the stomach and the interior of the intestine break the proteins into small fragments (peptides), the smallest of which (e.g. dipeptides) are then preferentially taken up by the "brush boarder" cells that line the intestine. Some tripeptides and quadpeptides are also taken up, but they are hydrolized to dipeptides during their uptake, so that they become dipeptides (or in some cases individual amino acids) within the cytosol of the brush boarder cells (QP552.P4S93:151). Within these brush boarder cells, "dipeptidase" enzymes that are specific to the second amino acid of the dipeptide (and are feedback regulated by the concentration of this amino acid in the cytosol) can further break down the dipeptide into its two amino acids. The individual amino acids then leave the brush boarder cells and enter the blood stream.

Therefore, the digestion of protein-bound SAMC could be expected to produce small peptides in the stomach and intestine, followed by the hydrolysis to individual amino acids by the cells of the intestinal brush boarder, and then to enter the blood stream as SAMC. However, the possibility remains that it enters the blood stream in another form (e.g. as dipeptides containing SAMC), or is otherwise not completely digested.

It is interesting to note that any such dipeptides or partial digestion products would be thiols and they could also metabolize to thiosulfinates (e.g. when exposed to ROS such as $H_2O_2$), and therefore are within the teachings and claims of the present invention. Perhaps such dipeptides do not however metabolize to breath AMS.

My conclusion is that, given that the actual metabolic pathway that results in AMS generation has not been determined (even in the case of garlic related compounds, JAFC53:1974), amino acid analysis for SAMC provides the most reliable way to determine whether protein-bound SAMC is present in any composition of interest.

7.1.3 Additional Experiments Performed and not Performed

As an alternative to starting with allyl mercaptan, some diallyl disulfide was purchased (from www.labdepotinc.com) and some capsules were made. Via exchange reactions, DADS can also be expected to be able to form protein-bound SAMC with the cysteine amino acid residues in the protein. DADS has the advantage of being more stable than allyl mercaptan, and it also has a more mild odor.

But because DADS is already a disulfide, and because the majority of the cysteine available in whey protein is already disulfide bonded (e.g. it is already in the form of cystine), some allyl mercaptan (¼ the amount of DADS) was added to allow the SAMC to form "catalytically" (see section 7.3.1.2).

Because DADS is not water soluble, the DADS was added to the whey protein directly (using an eye dropper to partially distribute it), then the water (containing diluted allyl mercaptan) was added and the mixture was blended. The mixture was allowed to further mix by leaving it in the refrigerator for a day, then poured onto trays for drying, etc.

The resulting tablets had significantly more garlic odor and taste than the tablets that start with allyl mercaptan, so this alternative was not pursued any further. However, for proteins that have predominantly "free" cysteines (not disulfide bonded), the DADS can be expected to form DADS more readily than allyl mercaptan would (because starting with allyl mercaptan requires some form of oxidation (e.g. exposure to air when drying) to allow the disulfide bonds to form, but DADS can participate in exchange reactions with free cysteines directly).

Another potential experiment that was not performed is the use of a detergent to improve the mixing of allyl mercaptan (or especially DADS) with water. Somehow the addition of a detergent didn't sound appetizing, and the mixing of allyl mercaptan seemed good enough. However, it is noted that in a production oriented process the use of a detergent (among various other process improvements that are known to those skilled in the art) could be beneficial.

7.2 Further Research into the Antioxidant and Oxidant Properties of *Allium* Related Compounds.

Due to the somewhat contradictory reports on the antioxidant (and oxidant) properties of allicin and other *allium*-related compounds and also to provide experimental evidence for some novel forms of antioxidants (and oxidants) that the present inventor was developing, further research was performed (both theoretical and experimental) that has led to discoveries providing a more complete understanding of the antioxidant and oxidant properties of *allium* related compounds, including discoveries with practical applications.

7.2.1 Choice of Model Compounds

Hydrogen peroxide ($H_2O_2$) was chosen for use as the model oxidant because it is readily available, sufficiently reactive to produce the desired effects, and sufficiently stable to be readily observed. The availability of an inexpensive real-time probe for $H_2O_2$ measurement (the ABD-3001, which could be leased by the month from Universal Sensors Inc.) was also a consideration.

Not only is $H_2O_2$ produced by a variety of types of cells during an immune system response, but other oxidants can also end up producing $H_2O_2$, as in the production of $H_2O_2$ from superoxide by thiols (JBC279:13272):

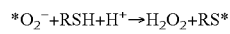

$$*O_2^- + RSH + H^+ \rightarrow H_2O_2 + RS*$$

Another consideration was that $H_2O_2$ has been used by other researchers doing similar experiments, allowing direct comparison of results (see below).

SAMC was chosen as the model *allium*-related compound. Therefore, allyl mercaptan is the model thiol, diallyl disulfide is the model disulfide, and allicin is the model thiosulfinate. Again, this simplifies comparison with previous research.

Red blood cells (RBCs) were used for experiments involving cells because they are easier to obtain than other cell types and provide a somewhat simpler "system" for analysis (no nucleus, no protein synthesis, no mitochondria, no citric acid cycle, . . . ) while having very active cysteine and glutathione metabolism.

Even with these simplifications, it was not practical to continue to rely on the "kitchen laboratory", so an analytical services company (Plant Bioactives Research Institute, Orem Utah) performed the experiments as work for hire, under the remote direction of the inventor. (Lab equipment became less of an issue, but budgetary constraints became more of one, so simplicity was still required.)

7.2.2 Reactions of Allyl Mercaptan with Hydrogen Peroxide

Thiols are known to have various antioxidant properties, including the ability to scavenge hydrogen peroxide ($H_2O_2$). Several studies of the reaction between various low molecular weight thiols (e.g. cysteine, N-acetylcysteine, glutathione) and $H_2O_2$ have been reported, but there does not appear to be a consensus as to the reaction products formed under various conditions or the mechanism(s) by which the products form. An extensive analysis of the reaction of cysteine with $H_2O_2$, including both a review of the literature and new experimental results, is presented in JOPS94:304.

The specific ability of allyl mercaptan in this regard was deemed worthy of being experimentally investigated because further experiments were planned that would rely on this ability. Unfortunately, the real-time probe for $H_2O_2$ measurement was found to drift significantly with time. A literature search revealed that probes (like this one) that use platinum in the probe tip react with thiols and lose sensitivity. Therefore, HPLC alone was used to measure the reactants and products.

Figure 7:
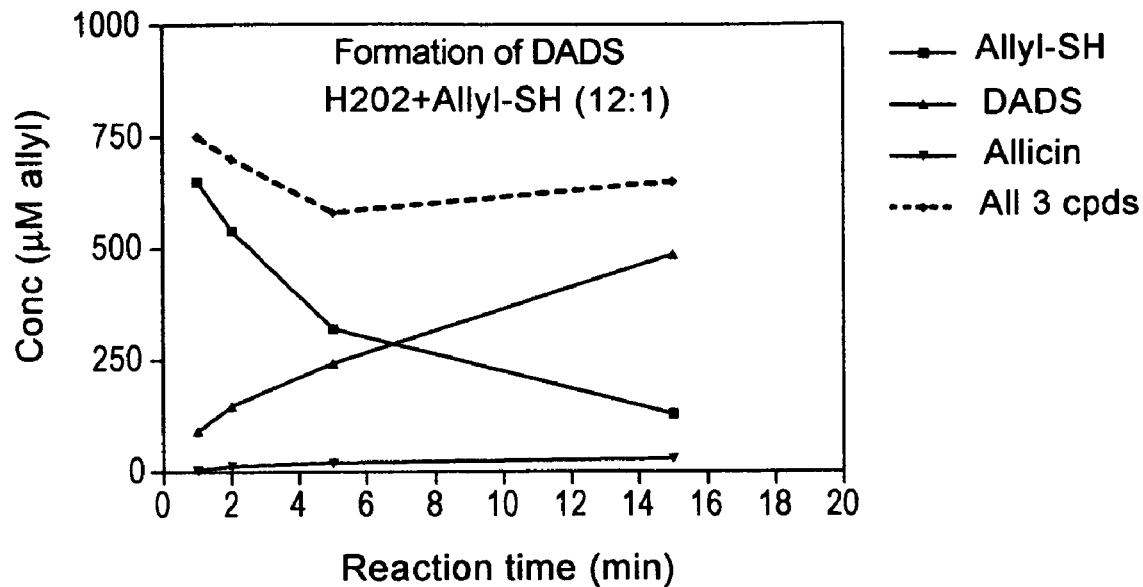
FIG. 7 is a graph showing the significant formation of DADS as a result of the reduction of $H_2O_2$ by AllylSH.

Starting with 0.85 mM of AllylSH and 10 mM of $H_2O_2$ the formation of diallyl disulfide was found to be essentially linear with time over the 15 minute duration of the experiment (see FIG. 7). The results confirm that allyl mercaptan (AllylSH) can serve as an antioxidant in the presence of hydrogen peroxide, reducing the $H_2O_2$ to $H_2O$ and oxidizing the AllylSH to diallyl disulfide (DADS, DAS2 in the figure) in the process.

In FIG. 7, the concentrations are reported as "uM allyl" to take into account the fact that each DADS molecule contains two allyl groups, while each AllylSH molecule has only one. The initial drop in "all 3 compounds" was later determined to be due to the hydrophobic compounds (DADS and to a lesser extent AllylSH) sticking to the glasswork.

Tests at other AllylSH and $H_2O_2$ concentrations confirmed that the amount of product was proportional to the AllylSH concentration, and to the $H_2O_2$ concentration (but the effect of the initial drop was more significant at lower concentrations). Surprisingly, some allicin was found among the reaction products.

Figure 8:
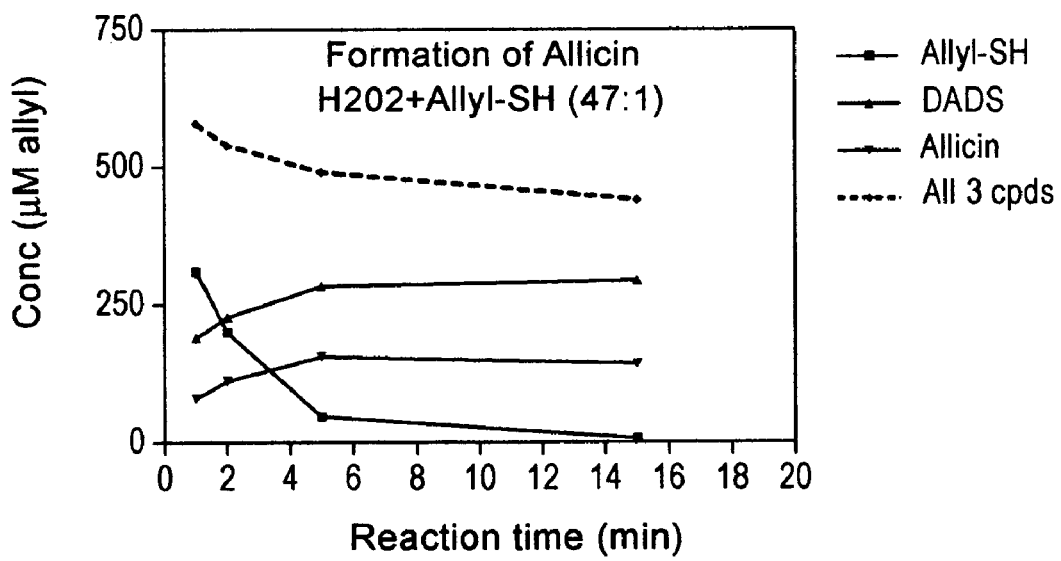
FIG. 8 is a graph showing the significant formation of allicin as a result of the reduction of $H_2O_2$ by AllylSH and DADS, in the presence of high $H_2O_2$ concentrations.

Another test with a significantly higher initial concentration of $H_2O_2$ (40 mM) provided a much higher allicin yield (32%, 143 uM allyl) (FIG. 8).

For convenience, the relevant molecular formulas are repeated below:

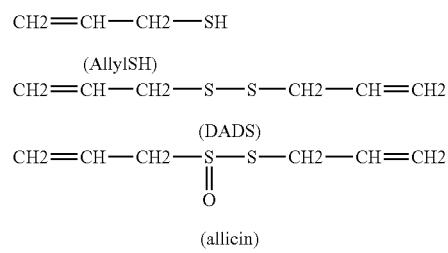

While not meaning to be bound to a particular theory, the following reaction mechanism is proposed for the production of allicin from AllylSH in the presence of $H_2O_2$ without DADS as an intermediary:

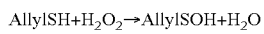

(Alternatively, AllylS⁻ could be involved in either reaction step, yielding OH⁻ instead of $H_2O$, without affecting the following conclusions.)

According to this theory, because the formation of allicin is doubly dependent on the concentration of AllylSOH (a sulfenic acid), which in turn is dependent on the concentration of $H_2O_2$, the resulting allicin concentration is a strong function of the $H_2O_2$ concentration.

Later, I found a paper describing the formation of thiosulfinates from cysteine and $H_2O_2$ that validates and extends these results.

The analysis (and experimental data) presented in JOPS94:304 shows that at low to moderate concentrations of $H_2O_2$, the direct formation of the disulfide predominates (illustrated as Scheme I in the JOPS94:304 reference), but at high concentrations there are competing paths for the sulfenic acid (illustrated as Scheme II in the JOPS94:304 reference), including as one alternative the reaction with another molecule of the sulfenic acid, yielding a thiosulfinate. But even at high $H_2O_2$ concentrations, their experimental data shows that the formation of the disulfide dominates (FIG. 7 of the JOPS94:304 reference), leading them to conclude that the alternative paths tend to also ultimately yield the disulfide (in other words, their Scheme II actually yields a higher disulfide concentration than Scheme I alone would produce). The analysis (and experimental data) presented in JOPS94:304 shows that the direct formation of cysteine disulfide is likely to involve the following two steps (their Scheme I):

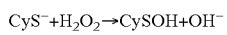

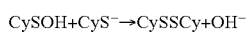

It is reasonable to assume that the direct formation of DADS from AllylSH in the presence of $H_2O_2$ can proceed via analogous reaction steps, with the net equation:

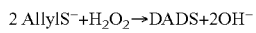

While not meaning to be bound to a particular theory, the following reaction mechanism is proposed as an alternative final step for the production of allicin from AllylSH in the presence of $H_2O_2$ with DADS as an intermediary:

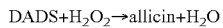

In practice, both reaction mechanisms can proceed in parallel, with any individual AllylSOH molecule reacting with either an AllylSH, an AllylSOH, or a DADS, depending on which it encounters first.

According to this theory, because both the formation of DADS and the subsequent formation of allicin are dependent on the concentration of $H_2O_2$, the resulting allicin concentration is a strong function of the $H_2O_2$ concentration. Therefore, when considering the significance of this reaction in a biological environment, note that any $H_2O_2$ concentration gradient will produce a stronger gradient of allicin formation.

An immediate question is whether a sufficiently high concentration of $H_2O_2$ is likely to ever be present in a biological system to achieve significant allicin production. Normally, the concentration of $H_2O_2$ is kept quite low (primarily due to the enzymes catalase and glutathione peroxidase), but various types of cells are capable of producing an "oxidative burst", typically as a way of attacking an invading organism. The neutrophil is a good example of a cell that can generate a high concentration of $H_2O_2$ when participating in an immune response.

Given that the $H_2O_2$ emitted from a small source (e.g. a neutrophil) will diffuse in three dimensions, the $H_2O_2$ concentration will also be a strong function of distance from this source. Therefore, the localization of allicin formation will be a very strong function of the localization of the $H_2O_2$ emission.

The neutrophil has an amazing ability to generate $H_2O_2$, as is indicated by experimental evidence (e.g. JBC259:399 "Quantitative and Temporal Characteristics of Extracellular $H_2O_2$ Pool Generated by Human Neutrophils"). Even when diluted in saline solution by approximately a factor of ten thousand (a diluted concentration of $3\times10^6$/ml vs an estimated packed cell density of $3\times10^9$/ml), the $H_2O_2$ concentration produced by stimulated neutrophils was shown to reach 12 uM. This corresponds to an undiluted $H_2O_2$ concentration of 120 mM. Note that a dilution of a factor of ten thousand corresponds to a linear separation distance between the neutrophils in the solution of slightly over 20 cell diameters.

Thus, the two $H_2O_2$ concentrations illustrated in FIGS. 7 and 8 can be considered representative of both the environment a short distance (e.g. several cell diameters) away from an activated neutrophil (FIG. 7, 10 mM $H_2O_2$) and the highly localized environment adjacent to an activated neutrophil (FIG. 8, 40 mM).

The neutrophil is presented here as a prototypical type of cell that can generate extracellular ROS, but various other types of cells can also generate extracellular ROS (including not only cells of the immune system but also even some "normal" cells that can participate in an immune system response when activated).

This experiment has demonstrated the non-enzymatic generation of allicin from allyl mercaptan (or DADS) exposed to $H_2O_2$ concentrations similar to those that occur local to intense oxidative stress in a biological system.

Normally, the primary defense from $H_2O_2$ damage is provided by the enzymes catalase and glutathione peroxidase (PHRE59:527). But catalase saturates when the $H_2O_2$ concentration is high, so it provides limited or no protection adjacent to an active neutrophil. Glutathione peroxidase requires the involvement of glutathione and produces GSSG which in turn must be reduced back to GSH by glutathione reductase, so after some initial protection it is also likely to saturate. This indicates that during intense oxidative stress the availability of non-enzymatic antioxidant protection may be more important than would otherwise be expected.

ROS emitted by cells can cause nearby cells also to produce ROS, which can create a destructive feedback cycle (Q11.N5V928:327). This feedback cycle results in the formation of intense oxidative stress more frequently than would otherwise be expected.

The present inventor emphasizes that the ability of allyl mercaptan and diallyl disulfide to produce allicin in the presence of high concentrations of $H_2O_2$ converts this non-specific oxidant which can produce a wide range of toxicities (and is implicated in the formation of a variety of more potent oxidants, such as the extremely reactive hydroxyl radical, *OH) to allicin, a much more specific and selective oxidant (see below). In particular, the normal immune system response to an infection can be potentiated through localized allicin formation because the allicin can fight the infection by inhibiting critical microbial enzymes (as shown in AAC32:1763), but has low toxicity to host cells. In the terminology of microbiology, the "selective index" of this process is extremely high.

This method is in contrast to the prior art method of targeted allicin delivery that was described in section 4.2.5.4, where alliinase conjugated to an antibody is used to produce allicin only at the location of a tumor. In the prior art, the location is determined by the specific antibody and the timing is determined by the timing of the injection of alliin. In the present invention, the location is determined by the location of the oxidative stress itself (e.g. the ROS generated by the host's immune system response), and the timing is determined by the timing of the oxidative stress.

Another advantage of the present invention over the prior art is that the metabolically produced thiol (e.g. allyl mercaptan) and to a certain extent the disulfide (e.g. DADS, see below) serve as beneficial antioxidants in between the oxidative stress events.

7.2.3 The Intracellular Reduction of SAMC and GSSG Drives Intracellular and Extracellular Antioxidant Activities 7.2.3.1 The Intracellular Formation of Allyl Mercaptan, Cysteine, Etc.

This experiment largely repeated what was already known about SAMC metabolism by red blood cells (PM59:A688), but it provided an opportunity to confirm the previous results and to prepare for further experiments.

Figure 9:
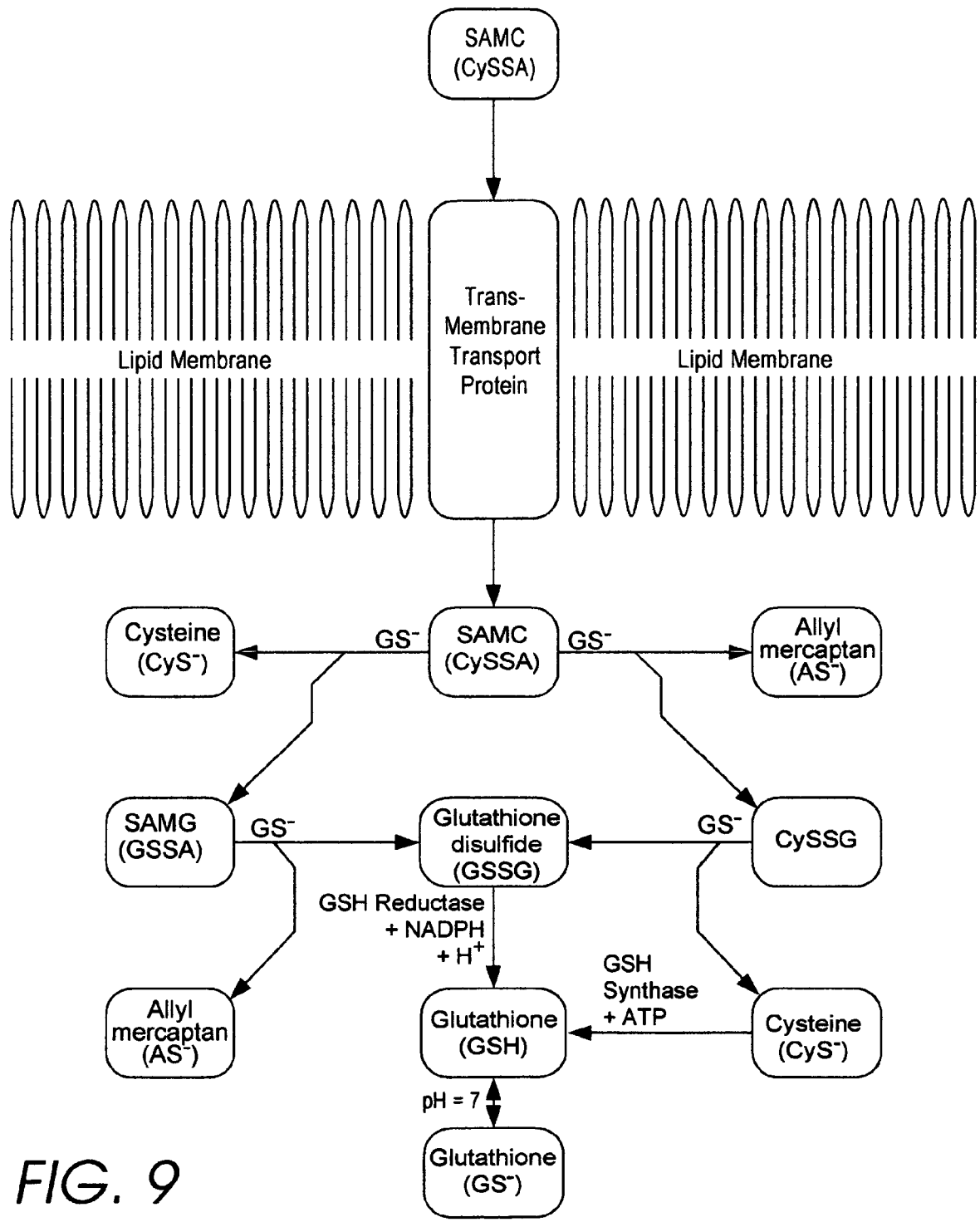
FIG. 9 is a diagram showing the intracellular metabolism of SAMC and some of the thiol-disulfide exchange reactions involved.

FIG. 9 illustrates the anticipated metabolic pathway of a low concentration of SAMC administered to red blood cells (RBCs), concentrating on the most significant thiol-disulfide exchange reactions (those involving GSH, the highest concentration thiol in the cell). Even this simple system involves three types of thiols (and their anions) and will also tend to have three types of mixed disulfides and three types of homogeneous disulfides present.

In FIG. 9, each allyl group is represented as "A" in the formulas. The thiols present are Cysteine (CySH, CyS⁻), reduced glutathione (GSH, GS⁻) and allyl mercaptan (ASH, AS⁻). The mixed disulfides are CySSA, CySSG, and GSSA. For simplicity, the formation of the disulfides CySSCy (cystine) and ASSA (diallyl disulfide, normally abbreviated as DADS) are not shown in FIG. 9, which can be justified if the incoming concentration of SAMC is low.

Because the cellular environment is highly reductive and the concentration of GSH is typically much higher than that of CySH or ASH, the concentrations of CySSCy and DADS can be expected to be quite low. For example, if the concentration of CyS⁻ is 10% that of GS⁻, then the probability of a disulfide molecule encountering a CyS⁻ and participating in an exchange reaction with it will only be 10% that of the disulfide molecule participating in an exchange reaction with GS⁻. This will lead to an equilibrium where the concentration of disulfides containing CyS will typically only be 10% the concentration of disulfides containing GS. Because the formation of CySSCy involves an exchange reaction between CyS⁻ and a mixed disulfide containing CyS (both of which have low concentrations), the probability of its formation is quite low. And once formed, any CySSCy molecule is likely to encounter a GS⁻ before long and produce CySSG and CyS⁻ via an exchange reaction.

The thiol-disulfide reaction rate is pH dependent due to the requirement for a thiol anion. For glutathione, the pKa is approximately 8.5, so at neutral pH the concentration of GS⁻ will be approximately 2% of the concentration of GSH.

Note that the total number of thiols is preserved by each exchange reaction (as is the total number of disulfide molecules). Therefore, it is just the mix that is changed. Each SAMC molecule entering the cell would increase the concentration of disulfides relative to thiols. But due to the enzyme glutathione reductase, the concentration of glutathione disulfide (GSSG) inside the cell is kept low (and is normally regulated within cells to approximately 1% of the GSH concentration), which in turn prevents (via exchange reactions) the concentrations of the other disulfides in the cell from increasing. In effect, the eventual formation of GSSG becomes a "sink" for excess disulfides, because the glutathione reductase enzyme will convert the extra GSSG molecule into two thiol molecules. Therefore, the result is that each new SAMC molecule entering the cell leads to the temporary formation of a GSSG molecule along with the net production of reduced cysteine and allyl mercaptan, through a variety of paths. Also illustrated, some of the cysteine can be used within the cell to produce more glutathione.

For the experiments, 0.25 ml of packed RBCs were suspended in 1.75 ml of phosphate buffer solution (PBS) along with an initial concentration 0.5 mM of SAMC. The formation of AllylSH and DADS was determined at incubation times of 10 and 30 minutes, both with glucose (10 mM) and without glucose in the medium.

Figure 10:
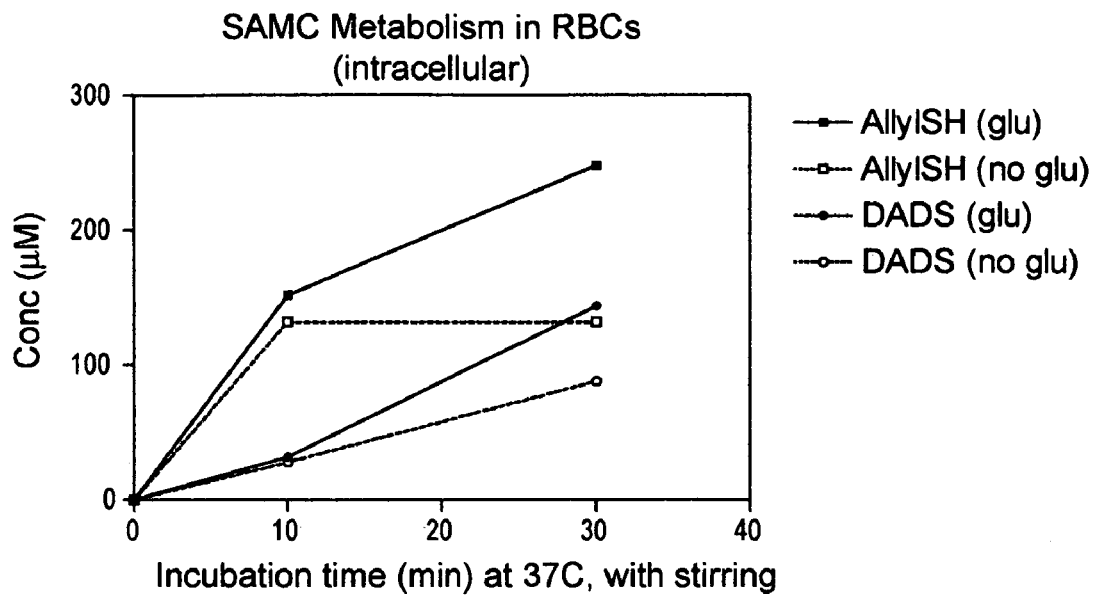
FIG. 10 is a graph showing the significant intracellular formation of AllylSH and DADS from administered SAMC.

The experimental results are presented in FIG. 10, which shows the intracellular formation of allyl mercaptan both with and without glucose added to the medium.

The significant effect of glucose is primarily due to the energy requirement for the reduction of GSSG to GSH by glutathione reductase, and the need for this "reductive power" to increase the concentration of thiols relative to the concentration of disulfides. As can be seen from FIG. 9, in the absence of glutathione reductase activity there will be a buildup of GSSG. Energy is also consumed by any production of additional GSH from the cysteine that has been added to the cell. So, without energy input, the concentration of GSH (and GS⁻) will decline and the ability to reduce the SAMC to allyl mercaptan and cysteine will also decline. (Although not determined, the import of SAMC into the cell may also consume energy and thus decline after ATP and glucose starvation.)

The effect of the depletion of energy in the cells deprived of glucose can be seen in the dramatic lack of increase in AllylSH for these cells after the initial rise. But the cells that were provided with glucose continued to produce AllylSH, with the concentration rising significantly over a 30 minute duration.

FIG. 10 also shows the surprising buildup of diallyl disulfide (DADS) in the cell as the SAMC is metabolized. In retrospect, this can be explained as being due to the known hydrophobic nature of DADS, along with its high membrane permeability, which allows it to accumulate in the cell membrane. (In other cell types, the membranes of the organelles within the cell would also accumulate DADS, but RBCs do not contain organelles.) The absence of glutathione in the cell membrane prevents any exchange reactions between DADS and GS within the membrane, so even if the DADS concentration in the cytosol remains low, the DADS that diffuses into the membrane will tend to stay there and can achieve a significant concentration.

Given the thinness of the cell membrane compared to the diameter of the cell, the concentration of DADS within the membrane itself must be quite high, given that the experimental measurement of DADS (which includes the entire volume of the cell) indicated a high concentration overall.

Interestingly, the formation of DADS from allyl mercaptan and its subsequent concentration in lipid membranes could account for the significant rate of disappearance of allyl mercaptan that is observed after garlic consumption (see section 4.2.5.2). The sequestering of DADS in membranes would significantly decrease the amount of DADS (and allyl mercaptan) in circulation, with perhaps the smaller amount in circulation persisting for a longer time than would otherwise be expected. This continued low-level presence of DADS would also explain the continued production of breath acetone that is observed during bioavailability tests (JAFC53: 1974). DADS is known to be a potent inhibitor of the CYP2E1 enzyme (NUCA25:241) that breaks down the acetone that is normally produced in the body, thereby increasing the concentration and the level of breath acetone, which is in this case believed by the present inventor to be a function of CYP2E1 inactivity (TAP146:255).

Even though DADS preferentially concentrates within membranes, the solubility in water is sufficient to allow it to diffuse within water, so a percentage of the DADS will diffuse inside the cell and also into the extracellular medium.

An estimation of the DADS concentration in the cell membrane can be made based on the partition coefficient. The partition coefficient for DADS has previously been determined to be 25.0 for n-octanol/water (JAFC50:6143), so a rough estimate of the membrane concentration would be 25× the concentration measured in the extracellular fluid. For comparison, the partition coefficient for alpha-tocopherol (vitamin E, which is concentrated in lipids, QP722.A8A586: 133) is 550 (JAFC50:6143) and the partition coefficient of allicin (which has been shown to be readily permeable through lipid membranes) is 12.3 (BBA1463:20). Although no published partition coefficient for allyl mercaptan was found, the partition coefficients were in the range of 0.3 to 0.4 for the other small molecular thiols reported in JAFC50:6143. Without wanting to be bound to a particular theory, the present inventor notes that a value within this range is not necessarily inconsistent with the tendency to separate when allyl mercaptan is mixed with pure water, because if allyl mercaptan is significantly less hydrophilic than the water itself is, the result would be a separation between the allyl mercaptan and the water.

Figure 11:
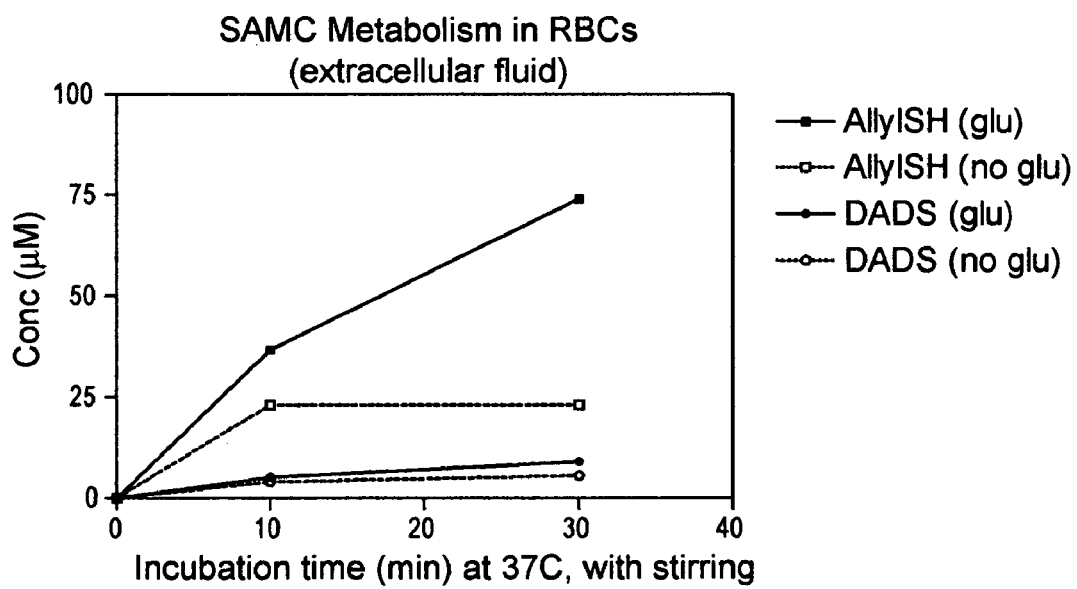
FIG. 11 is a graph showing the significant extracellular presence of AllylSH and DADS as a result of lipid membrane permeability.

FIG. 11 shows the experimentally determined extracellular concentration of DADS both with and without glucose added to the medium. The maximum concentration in the extracellular fluid was 0.009 mM (DADS (glu) at 30 minutes), which calculates to an estimated membrane concentration of 0.225 mM. The corresponding concentration of AllylSH in the extracellular fluid was 0.074 uM, which with an assumed partition coefficient of 0.35, calculates to 0.026 uM within the cell membrane.

7.2.3.2 Allicin Formation within the Cell Membrane

Because allicin is known to react rapidly with thiols (and AllylSH is a thiol), the formation of allicin from AllylSH in the presence of $H_2O_2$ was suspected of being limited by a significant reverse formation of DADS from the allicin:

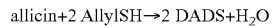

allicin+2 AllylSH→2 DADS+$H_2O$

The environment within the membrane had now been determined to have a higher concentration of DADS than AllylSH, due to the lipophilic nature of DADS, so it was decided to perform another experiment to see if less $H_2O_2$ was needed for allicin production when the starting DADS concentration was significantly higher than the starting AllylSH concentration (which is the opposite of the starting condition of the experiment with $H_2O_2$ that was previously performed).

Figure 12:
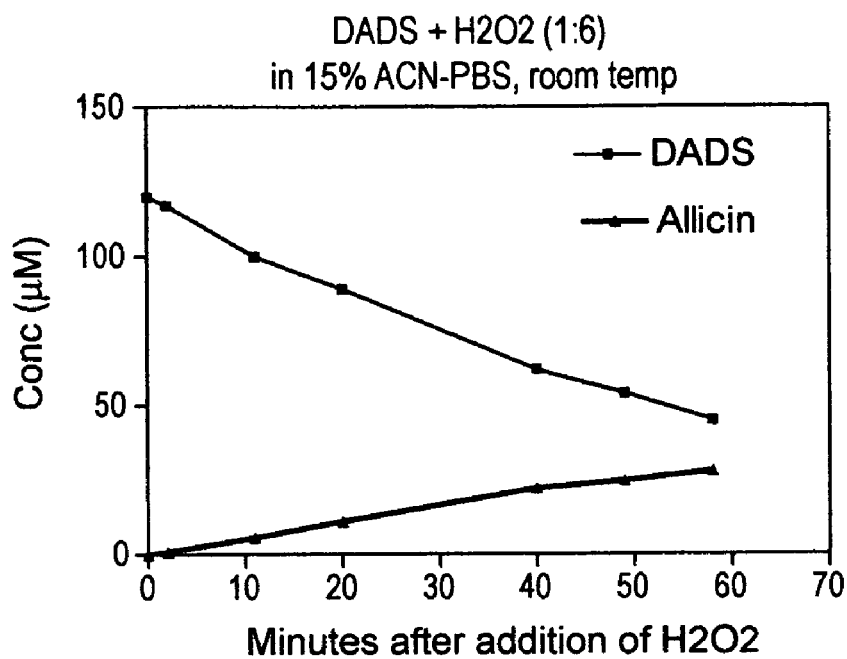
FIG. 12 is a graph showing the significant formation of allicin as a result of the reduction of $H_2O_2$ primarily by DADS, in the presence of moderate $H_2O_2$ concentrations.

An experiment starting with 0.2 mM of DADS in the presence of 5.0 mM of $H^{20}_2$ and performed at room temperature proved this to be the case (FIG. 12). In the absence of AllylSH the rate of allicin formation was increased and was essentially linear with time.

Figure 13:
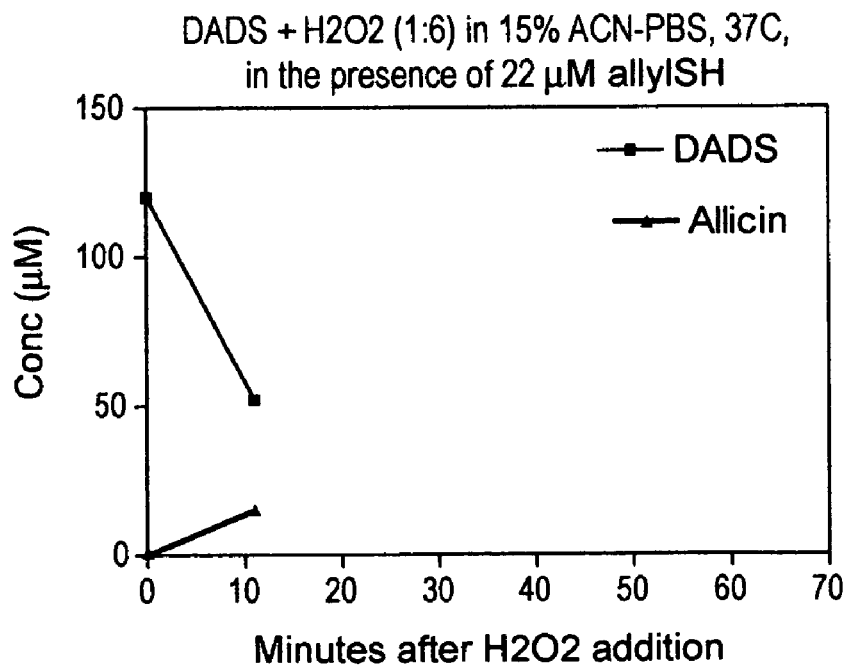
FIG. 13 is a graph showing the significant formation of allicin as a result of the reduction of $H_2O_2$ primarily by DADS, in the presence of moderate $H_2O_2$ and AllylSH concentrations.

Another experiment was performed at approximate body temperature (37 degrees C.) and calculated membrane AllylSH concentration. Starting with 0.2 mM of DADS and 0.022 mM of AllylSH in the presence of 5.0 mM of $H_2O_2$ the allicin yield was 0.015 mM at 11 minutes (FIG. 13).

In comparison with the previous experimental discovery of significant allicin formation from AllylSH in the presence of high $H_2O_2$ (e.g. in the extracellular environment adjacent to an activated neutrophil, see section 7.2.2), this new aspect of the present invention indicates the potential use of the formation of allicin (or other form of thiosulfinate) within the cell membrane as a defense against $H_2O_2$ and other ROS, particularly during oxidative stress events. The production of allicin has now been shown to occur at a significantly lower $H_2O_2$ concentration than was used in the previous experiment, which would extend the anti-inflammatory range to a significantly greater distance from the source of ROS than was calculated in section 7.2.2.

7.2.3.3 Extracellular Antioxidant Activity Linked to the Intracellular Antioxidant Network Interestingly, as shown in FIG. 11, AllylSH was also found in the extracellular fluid. This was not unexpected by the present inventor. AllylSH is a small, non-polar molecule and although it is usually grouped with the "water soluble" garlic components (as opposed to the "oil soluble" components, when such a distinction is being made) it was also expected to have reasonable permeability through lipid membranes. (If its partition coefficient is as close to 1 as that reported for other small thiols, the permeability through lipid membranes would be excellent, especially because it is normally non-ionized at pH 7.)

In fact, one of the primary goals of these experiments was to determine whether the intracellular allyl mercaptan (produced, in effect, by the reductive power provided by glutathione reductase) would diffuse through the membrane to the extracellular fluid, thereby providing an extracellular antioxidant that remains coupled (via the return diffusion of DADS and its subsequent reduction) to the intracellular antioxidant network.

This antioxidant mechanism would be analogous to that observed in some cell types that actively import cystine, reduce it internally to cysteine, and export the cysteine into the cellular environment (see section 4.4.1 above).

There is further evidence that red blood cells have extracellular antioxidant abilities that are not shared by other types of cells (e.g. endothelial cells), and can provide protection when introduced into tissues where they would not normally be present (e.g. on the surface of the lung), via a mechanism that is coupled to the intracellular antioxidant network (S227: 756). One possible mechanism for this is that vitamin C (JCI63:53) in its reduced state passes through the membrane of red blood cells into the extracellular environment, with the oxidized molecules being actively transported back into the cells for reduction by glutathione.

But the membrane permeability of DADS and AllylSH would be a general property of lipid membranes, and the intracellular antioxidant network is a general property of cells, so this mechanism would be expected to be operative in a broad range of cell types (essentially, every type of metabolically active cell).

Figure 14:
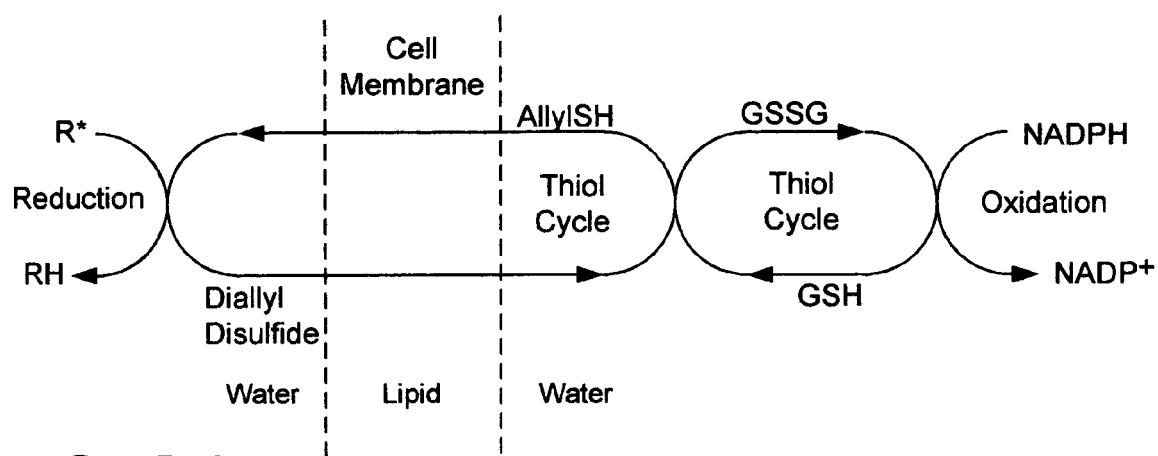
FIG. 14 is a diagram of the transmembrane antioxidant cycle illustrating the transmembrane coupling of an extracellular antioxidant with the intracellular antioxidant network.

The ability of DADS to enter the cell through the cell membrane and be metabolized to AllylSH was already well established (PM59:A688). The new experimental results showing the efflux of AllylSH from the cell have now completed the loop, as is shown in FIG. 14.

In effect, this couples the intracellular antioxidant network to the extracellular environment by using diffusion and exchange reactions to semi-randomly distribute the oxidized product until it shows up as intracellular GSSG, which is then rapidly removed by the enzyme glutathione reductase (with 2 GSH produced in the process). By the law of mass action this contributes to the creation of a generally reductive environment at the expense of the energy provided to glutathione reductase to drive the system.

These experimental results show that this transmembrane diffusion of both the (unoxidized) thiol into the extracellular medium and the corresponding return diffusion of the (oxidized) disulfide into the cell does in fact occur, and this constitutes a significant aspect of the present invention.

7.2.4 Investigation into the Anomalous Behavior of Allicin as an SH Reagent

Figure 15:
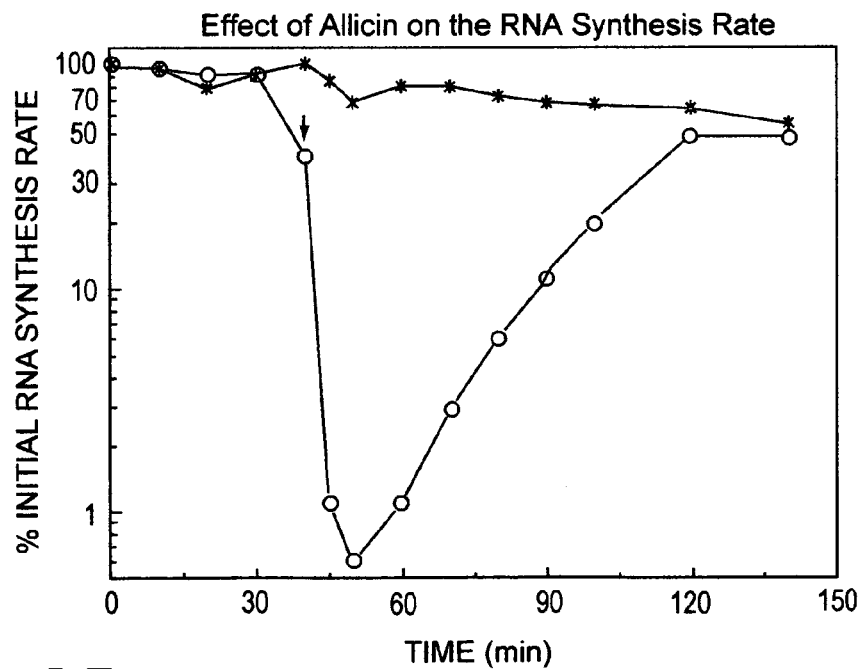
FIG. 15 is a graph showing the inactivation of an SH-sensitive RNA synthesis enzyme by allicin, based on the experimental results presented in AAC32:1763.
Figure 16:
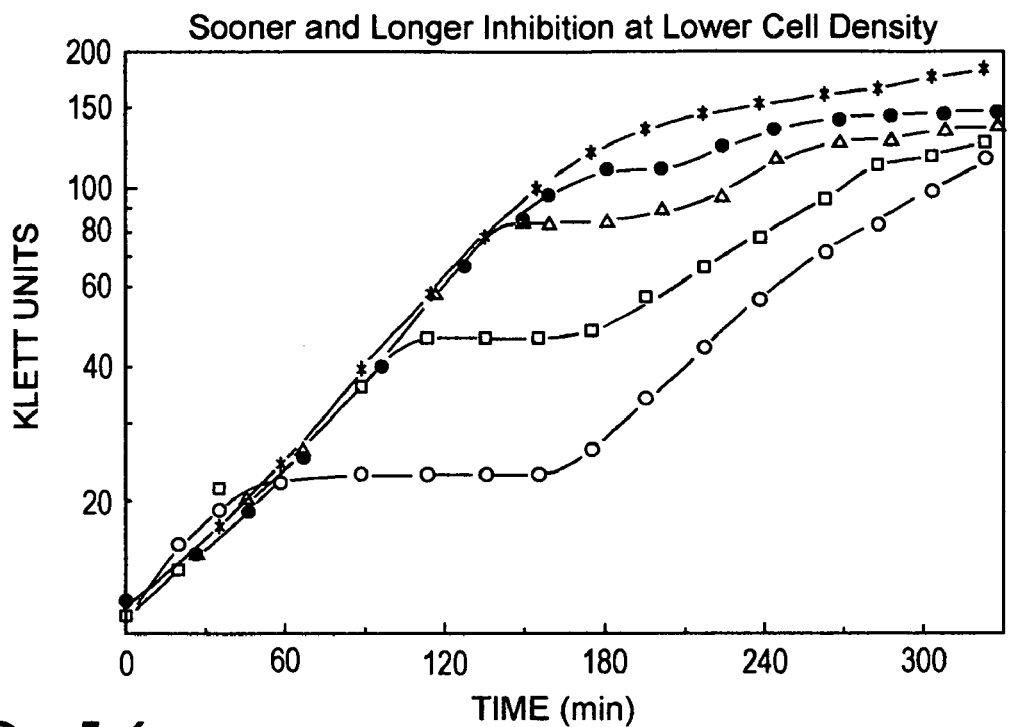
FIG. 16 is a graph showing the effect of culture density on the inactivation and recovery of growth, based on the experimental results presented in AAC32:1763.

Some researchers have questioned whether the enzyme inhibition by allicin is actually due to sulfhydryl blocking. In a study on the allicin inhibition of bacterial growth (AAC32: 1763), the effect on RNA synthesis is so dramatic that the authors suggest that allicin must be acting not as a general inhibitor of sulfhydryl-dependent enzymes but rather as a specific inhibitor of RNA synthesis. The allicin treatment 40 minutes into the experiment rapidly reduces the rate of bacterial RNA synthesis to below 1% of that of control cells, as is shown in FIG. 15 (which is derived from FIG. 4 of the AAC32:1763 reference). Other anomalies noted were the lack of a simple linear or logarithmic relationship between allicin concentration and growth inhibition. Instead, the effect of allicin concentration is highly dependent on the culture density, with a lower density culture being inhibited both sooner and for a longer duration (at a fixed concentration of allicin), as is shown in FIG. 16 (which is derived from FIG. 2 of the AAC32:1763 reference), with the lowest density shown by the line with open circles. And the effect observed with increased allicin concentration was not a change in the degree of growth inhibition but instead was an increase in the duration of the growth inhibition phase. When growth resumed, it was at a somewhat lower rate, which was determined by the initial allicin concentration.

Another group which performed an investigation of the inhibition of acetyl-CoA synthase that compared the effect of allicin with that of another well known thiol-group blocker of acetyl-CoA synthase (p-hydroxymercuribenzoate) found that the activity of allicin could not be due to the same SH-blocking mechanism because its activity was not affected by the reducing agent dithioerythritol (which prevents other SH-blocking agents from being active)(FEBS261:106). They also determined that the inhibition was spontaneously reversible by passing the mixture through a gel filtration column. Their conclusion was that allicin must be a specific, non-covalent, inhibitor of acetyl-CoA synthase.

However, the present inventor has determined by research and experiment that the experimental observations that previously appeared anomalous are in fact consistent with a different form of exchange reaction (thiol-thiosulfinate) that has a similar enzyme blocking effect to the thiolate-disulfide exchange reaction that occurs with other SH-blocking agents.

The following presentation first develops the evidence for the proposed enzyme inhibition mechanism for allicin (and other thiosulfinates), then compares this with the known properties of another "anomalous" SH-reagent (S-aryl sulphenylthiosulphates). These properties will then be shown to explain the experimental results that have intrigued the previous researchers.

7.2.4.1 The Mechanism by which Allicin Reacts so Rapidly with Thiols

The rapid reaction of allicin with cysteine (<1 minute half-life) that was reported in PM59:A688 was in surprising contrast to the slower reaction of DADS with cysteine (45 minute half-life) that they also report. (See TABLE I in section 4.2.5.1 above.) If the reaction mechanisms both proceed by a thiol-disulfide exchange reaction, both reaction rates would be expected to be similar and to be rate-limited primarily by the concentration of $CyS^-$ ions. This is a general property of thiol-disulfide exchange reactions, which are rapid but require the thiol to be ionized.

The rate of exchange reactions involving cysteine residues has previously been determined experimentally by observing the formation of mixed disulfides from a starting mixture of cysteine+glutathione disulfide, and also in a companion experiment starting with a mixture of glutathione+cysteine disulfide (EJB2:327). In both cases, the reactions were rapid and achieved equilibrium concentrations in only 15 minutes (at 37 degrees C.). This reaction rate is apparently compatible with the observed half life of DADS with cysteine of 45 minutes (at 25 degrees C.). In each case, the reaction rate is primarily determined by the concentration of $CyS^-$ ions, while being affected to a lesser extent by other conditions such as temperature.

At a pH of 7, only approximately 2% of the cysteine is ionized (the pKa of CySH is 8.44 (JOPS94:304)). It is interesting to note that the ratio of the half-life of allicin (less than 0.5 minutes) to the observed half-life of DADS is on the order of 1%, which is reasonably close to this percentage. This led the inventor to investigate whether the reaction with allicin could involve un-ionized cysteine directly, and therefore not be a thiol-disulfide exchange reaction. Because the concentration of un-ionized cysteine is approximately 50 times that of $CyS^-$, this suggested an explanation for why allicin reacts so much faster than DADS.

Although the reaction of allicin with cysteine has been well established (being first reported by Cavalitto in 1944) (JACS66:1952) and was confirmed in PM59:A688, no detailed investigation of the reaction mechanism appears to have been performed prior to the investigation of the reaction of allicin with the cysteine residue of glutathione by Miron et al (WO:01/36450). These results were very interesting.

First of all, these authors conclude that the forward reaction is:

2 GSH+Allicin→2 AllylSSG+H$_2$O

They named AllylSSG "S-Allylmercaptoglutathione" because it consists of the mixed disulfide of allyl mercaptan and glutathione.

The present inventor's reasoned attempt at a reaction mechanism yielded:

Allicin+GSH→AllylSSG+AllylSOH     1.

AllylSOH+GSH→AllylSSG+H$_2$O     2.

Miron et al (WO:01/36450) also have shown that the reaction rate has a strong dependence on pH over the pH range of 5 to 7 and concluded that this indicates that the glutathione is in the form of a mercaptide ion ($GS^-$). But the required participation of a mercaptide ion in the reaction is inconsistent with the hypothesis that the present inventor's had formed that reaction with allicin could involve un-ionized cysteine directly. It was also inconsistent with the forward reaction mechanism advanced in the present disclosure.

Another consideration is that the pH dependence presented in WO:01/36450 shows that the reaction rate (K in their FIG. 6) varies from almost 0 at pH=4.5 to almost 100 at pH=7, which is inconsistent with the formation of a mercaptide ion because the pKa of glutathione is approximately 8.5, so the glutathione will be almost completely un-ionized throughout this pH range. If the transition was associated with ionization, it would be expected to have occurred primarily in the pH range of 8 to 9.

The present inventor however has found a different explanation, not previously appreciated, for this pH dependence. Glutathione can convert to a thiazoline form (eliminating a water molecule in the process) at low pH (or even medium-low pH), and then it is no longer a thiol at all! (QP801.G6C6, pages 21-29). At low pH, the infrared absorption spectrum (QP801.G6C6, page 24) clearly shows the absence of any cysteinal moiety and the establishment of the characteristic thiazoline peak at 2610 angstroms. The pKa of this transformation is 5.3 which, means that the transition between forms occurs gradually within the pH range of 5 to 7 (QP801.G6C6, page 29), thus offering an alternative explanation of the pH dependence that is reported in WO:01/36450.

Confirmation of the feasibility of the reaction not involving any $GS^-$ ions was eventually achieved when the present inventor found a description of the reaction of S-monoxides (thiosulfinates) with thiols yielding mixed disulfides (QP551.T6913, page 95):

$$\underset{O}{RS\overset{\parallel}{S}R} + 2\,R'SH \longrightarrow 2\,RSSR' + H_2O$$

Substituting R=Allyl and R'SH=GSH yields the desired overall reaction.

Thus, the rapid reaction of allicin relative to diallyl disulfide has now been explained. It is a thiol-thiosulfinate reaction, not a thiol-disulfide reaction.

Experiments were performed which confirmed that the reaction rate between cysteine and allicin is independent of pH over the range of 8-10 and also that the reaction rate between cysteine and diallyl disulfide has the expected dependence on pH, with the reaction rate dramatically increasing between pH 8 and 9 (the pKa of cysteine=8.5). Interestingly, it was also determined that the reaction rate between cysteine and allicin remained high at least up to pH 10, implying that allicin can also react rapidly when the ionized form of the thiol ($CyS^-$) predominates.

Why is all of this important? For one thing, it shows that allicin can directly convert an exposed SH group on an SH dependant enzyme to a mixed disulfide, independently of whether it is ionized or not, thereby inactivating the enzyme. This explains the amazing effectiveness of allicin as an enzyme inhibitor. Other SH-blocking reagents require high concentrations (e.g. over 10 times the concentration of the enzyme that they are inhibiting) in order to inhibit the enzyme quickly. But allicin can be effective at a ratio as low as 1 to 1 (see below).

How else is this different from how a thiol-disulfide exchange reaction can inactivate an enzyme? Because here the enzyme has lost a way to defend itself.

For a thiol-disulfide exchange reaction to occur, the thiol needs to be ionized to a thiolate ion ($RS^-$). Because the thiol is part of the enzyme, the enzyme is in control of whether the thiol is likely to be ionized at the physiological pH (typically near 7) by controlling (e.g. through evolution) the pKa of the thiol. The pKa of the thiol will also depend in part on the other portions of the enzyme that are near the thiol, and may change as the enzymatic reaction proceeds.

Interestingly, Wills (BIJ63:514) points out that Cavallito (JACS66:1952) found that 1:125,000 allicin completely inhibited the growth of fourteen out of the fifteen strains of bacteria tested, but that half that concentration had no effect on any strain tested. He notes that some vital oxidation enzymes are powerfully inhibited by allicin with a threshold within this range and that this can adequately explain the antibiotic action of allicin.

It seems that the affected enzymes have not diverged significantly during bacterial evolution. This adds credence to the claim that bacteria do not develop resistance to allicin (MI2:125).

Allicin is primarily bacteriostatic (although it can be bactericidal at higher concentrations). By preventing the replication (or by significantly slowing it down), the body has more time to kill the microbes. But is also interesting that this confers a low toxicity to allicin because its cytostatic effect on the host's cells merely delays their replication until after the infection has been controlled. Although some of the host's enzymes may also become inhibited, no damage is done, in that the mixed disulfide can be converted back to an exposed SH group by a future thiol-disulfide exchange reaction. In other words, the microbes are killed because the host's immune system eventually kills them. Allicin just helps in the process.

By combining a simple mechanism that affects all cells in a fundamental way (and therefore cannot easily be avoided) with a sophisticated mechanism that distinguishes between host and infectious cells, allicin and the immune system efficiently work together to defeat the microbes with minimal damage to the host. It is an important aspect of the present invention that these special properties of thiosulfinates as enzyme inhibitors have now been established on a theoretical basis, which enables the design on a rational basis of future *allium*-related (thiosulfinate based) enzyme inhibitors.

Although for the purpose of illustration this description concentrates on enzymes which are inhibited by SH-blocking, there are also enzymes which are activated by SH-blocking, and there are proteins that are controlled in various ways by SH-blocking. The present invention is equally applicable to these and can provide mechanisms to activate and control them, as will be readily understood by those skilled in the art.

7.2.4.2 Various Inhibition Properties Explained

For the purpose of explaining and illustrating the inhibition properties of thiosulfinates, a comparison will be made with another class of SH-blocking reagents (S-aryl selenenylthiosulphates) which exhibit similar behavior and have previously been extensively characterized. After justifying the comparison and presenting the characteristics of these SH-reagents, the original observations of anomalous behavior of allicin will be addressed and resolved. The theory presented in this section is not fundamental to any aspect of the present invention, but is believed by the present inventor to be worthy of including within the teachings.

The primary justification for the comparison is merely to show that such other enzyme inhibitors with these characteristics exist. However, without wanting to be bound to a particular theory, an informal comparison of the structural characteristics between the S-aryl selenenylthiosulphate and thiosulfinate molecules will show that they are more related than would otherwise be apparent.

A limited number of reports in the literature provide evidence for the similarity in chemical behavior of thiosulfinates and sulfoxides. Thiosulfinates, which have the general structure RS(O)SR', can spontaneously and reversibly interconvert to sulfoxides of the structure ROSSR' (JACS96:3929). In effect, the oxygen atom and the two sulfur atoms form a more linear configuration, instead of the oxygen atom being double bonded to one of the sulfur atoms.

It is interesting to note that when Cavallito et al initially proposed the thiosulfinate structure for allicin (JACS66:1952), they also considered the sulfoxide structure, but preferred the thiosulfinate option in part because thiosulfinates are more water soluble. But allicin has also been shown to be extremely soluble in lipids (with a partition coefficient of 12.3, it even prefers lipids to water). The present inventor notes that perhaps the high diffusion rate of allicin through lipids is due to it converting to the more lipophilic sulfoxide structure while within the membrane.

The sulfoxide can be considered as an instance of the more general structure RXSSR' where X represents any atom from the 16th column of the periodic table (the chalcogens, i.e. O, S, Se, . . . ). Substituting a sulfur atom for the oxygen atom in this general equation results in a trisulfide. Interestingly, the trisulfide DATS (diallyl trisulfide) was previously shown to react with cysteine almost as rapidly as allicin does (PM59:A688, its table summarized in section 4.2.5.1 above).

Similarly, substituting Se for X produces the structure RSeSSR', which is the structure of the S-aryl selenenylthiosulphate thiol blocking reagent $SnO_2Ph-Se—S—SO_3^-$ that has been extensively characterized (BIJ221_797), along with its selenosulfide analog ($pNO_2Ph-Se—SO_3^-$).

Figure 17:
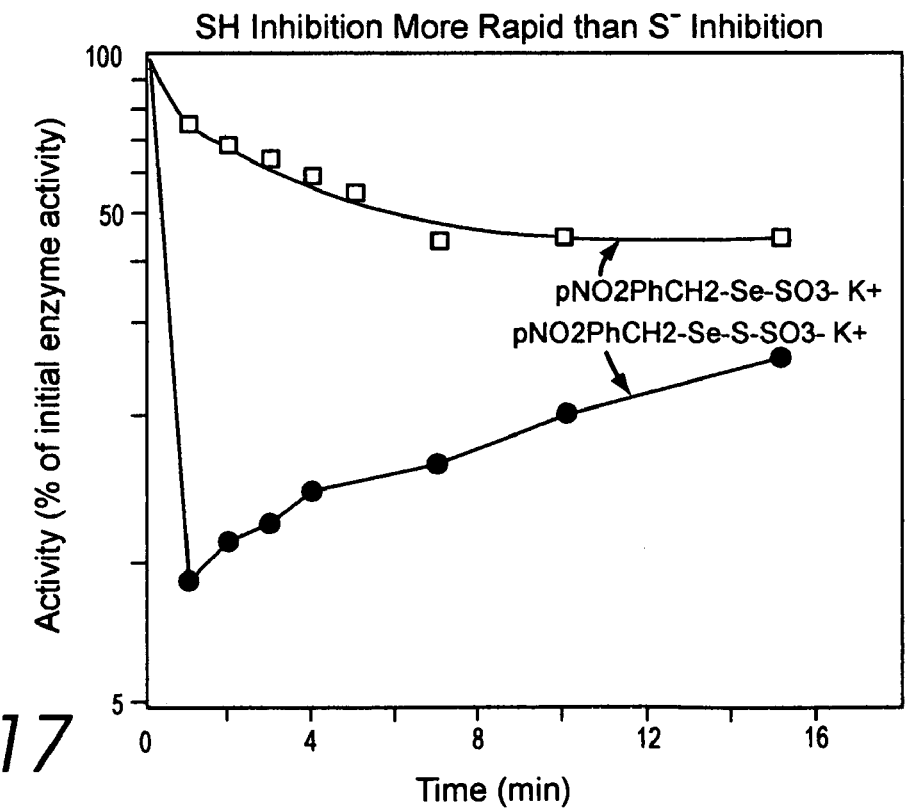
FIG. 17 is a graph showing the time-dependent inhibition of papain by two classes of enzyme inhibitor, based on the experimental results presented in BIL221:797.

FIG. 17 (derived from FIG. 1 of BIJ221_797) shows that the selenosulfide reacts similarly to the expected behavior of a disulfide, smoothly approaching at a reasonable rate the limit of ~50% inhibition of the associated SH-dependent enzyme. The moderate rate is presumably due to the pKa of the SH group of the enzyme being unfavorable, because the thiol needs to be ionized ($PS^-$) in order to participate in the exchange reaction.

or other exchanges with similar probability, for example

The inhibition limit of 50% is also expected given that in a closed system the respective concentration of thiols and of disulfides (and in this case, also the selenols and selenosulfides) do not change, they just get swapped around. If the inhibitor concentration is not in excess (which is the case here), the random mixture of thiols, selenols, disulfides, mixed disulfides, and selenosulfides will still keep the quantity of (thiols+selenols) equal to the quantity of (disulfides+mixed disulfides+selenosulfides). The net result is that roughly half of the enzyme molecules can be expected be blocked at any given time.

The corresponding plot for the S-aryl selenenylthiosulphate is significantly different, both quantitatively and qualitatively. The initial reaction is nearly instantaneous and almost completely inactivates the enzyme (>90% by the first data point). Then the amount inactivation actually decreases, perhaps approaching the same 50% limit as that of the selenosulfide.

The instantaneous inactivation of the enzyme implies that the reaction rate is not limited by the pKa of the SH group, but instead the unionized thiol (SH) can participate in the exchange reaction. The reversal of inactivation can also be seen as being due to the continued participation of all of the compounds in exchange reactions. Given that the quantity of thiols+selnols is comparable to the quantity of disulfides+mixed disulfides+selenosulfides, and that the thiols (and selenols), when ionized (but only when ionized) can reduce the enzyme back to its active "SH" state, the rate of reactivation can be seen to be moderated by the limited concentration of RSe⁻ and R'S⁻ available.

Thus, informally speaking, after an initial "burst" of activity the S-aryl selenenylthiosulphate molecules have been completely consumed and replaced with the various thiols, selenols, disulfides, mixed disulfides, and selenosulfides. Thus, the system rapidly settles into a dynamic state where the enzymes are continuously being inhibited and activated via exchange reactions involving all of these compounds and it approaches its final equilibrium at a moderate rate.

Thus armed, we can now return to the task at hand.

7.2.4.3 Reinterpretation of the Formerly Anomalous Experimental Results

For the purpose of this section, the enzyme inhibition abilities of allicin will be assumed to be those presented in BBA1379:233 (the most comprehensive study available), augmented by consideration of the comprehensive study of the characteristics of S-aryl selenenylthiosulphate presented above.

First, we address the observations in AAD32:1763 (In Vitro Mechanism of Inhibition of Bacterial Cell Growth by Allicin).

The dramatic effect on RNA synthesis that was observed (reproduced in FIG. 15) is in line with the dramatic, instantaneous inhibition of papain shown in BBA1379:233, where it was noted that "the rate of inhibition was very fast, therefore, it was impossible to make a time-dependent inhibition study". The degree of inhibition that was observed is also consistent with the degree of papain inhibition shown in BBA1379:233 (~99%). So neither of these are out of line for allicin, they are just different than what would be expected based on the performance of other SH-enzyme inhibitors.

The concentration dependent behavior is explained by the "suicidal" nature of allicin, in that each allicin molecule can inhibit one and only one target enzyme molecule. Given that each allicin molecule can inhibit an enzyme molecule the first time that it encounters it (the allicin is never turned away because the "SH" isn't currently in its "S⁻" state), the allicin is consumed rapidly. But each bacterium can continue to synthesize RNA until it runs out of its pool of nucleotides, hence the lower density cell cultures (with more allicin per cell) run out of nucleotides sooner and exhibit the shorter lag period (reproduced in FIG. 16).

Now it gets even more interesting. For each enzyme molecule that gets inhibited by allicin, an enzyme activator (AllylSH) is also released, according to the equation:

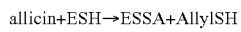

allicin+ESH→ESSA+AllylSH

The original activated enzyme (ESH) has become inactivated by the blocking action of an allyl mercapto radical that is now covalently bonded to the enzyme's previously exposed cysteine (ESSA), but an AllylSH has also been released, which will diffuse around for a while. In a low concentration of cells, this diffusion time will be longer than that observed when the cellular concentration is high. Also, whenever the AllylSH encounters a blocked enzyme, 98% of the time it will be in its AllylSH state and only 2% of the time will it be in its AllylS⁻ state. Therefore, most of the time it will not be able to participate in an exchange reaction, so the enzyme will remain inactivated. But eventually, it will encounter an enzyme molecule when it is in its S⁻ state and it will be able to reactivate the enzyme via an exchange reaction. Thus both the shorter lag time and the longer inactivation time observed for lower cellular concentrations fits the model for allicin, even though this is different from that of other SH-dependent enzyme inhibitors. The lower final growth rate is also consistent with the continued presence of DADS, which serves as a less reactive (but longer lasting) enzyme inhibitor than the allicin.

The behavior of allicin when inhibiting acetyl-CoA (FEBS261:106) is also explained by the experimental results reported in BBA1379:233, where several types of enzymes were tested to determine the specificity of allicin inhibition of known SH-sensitive enzymes. It was clearly shown that in each case allicin was behaving as an SH-reagent, although the ability of other SH-reagents to recover the enzyme activity depended on the nature of the enzyme. In particular, dithioerythritol (the reagent that yielded unexpected results in FEBS261:106) was shown to be able to recover activity of the enzyme "TBAD" but not of the enzyme "HLAD", while the alternative SH-reagent "2-ME" was able to recover enzyme activity. (In other words, the ability of an SH-reagent to recover enzyme activity tells as much about the enzyme as it does about the nature of the initial inhibitor.)

The recovery of enzyme activity after gel filtration is also in line with the observations in BIJ221:797, where it was observed that S-aryl selenenylthiosulphate recovered activity during chromatography due to the separation of the continuing inhibitor (which would be DADS in the case of allicin) from the inhibited enzyme (presumably allowing the AllylSH still present to reactivate the enzyme, in the case of allicin).

7.2.5 Antioxidant Vs. Pro-Oxidant Properties of Garlic and Allicin Explained.

Why do garlic and allicin have predominantly antioxidant properties? Because they are quickly metabolized to allylSH, which has the same antioxidant properties as any thiol, including the ability to detoxify most forms of reactive oxygen and reactive nitrogen. In other words, although allicin commonly shows oxidant properties when tested outside of a living organism, when instead it is metabolized by animals or otherwise allowed to break down to allyl mercaptan, the long term effect is that of an antioxidant.

Why do garlic and allicin have occasional pro-oxidant properties, even long after consumed? Because even though they were quickly metabolized to allylSH and other metabolites such as DADS, allicin can be formed again enzymatically by monoxygenase enzymes or non-enzymatically in response to oxidative stress.

Why do raw garlic and allicin have toxic properties when initially consumed? Because the oxygen atom of the allicin molecule makes it somewhat unstable and capable of producing reactive oxygen through various reaction mechanisms. Because DADS is a stable molecule, the loss of the extra oxygen atom is not unfavored (informally speaking, any reaction with another molecule is likely to leave the oxygen atom on the other molecule, with the DADS molecule floating away). Note that the tissue damage from allicin that has been observed (JN131:1109S) must involve a different mechanism from the reactions with thiols that have been extensively discussed herein (e.g. enzyme inhibition) because the exchange reaction with thiols is readily reversible and does not damage them.

With regards to the present invention, the thiol compounds allyl mercaptan, cysteine, and glutathione are antioxidants, while the enzymatically produced allicin is pro-oxidant. Thus, all of the discussion about the exceptional ability of allicin to inhibit enzymes should be contrasted with the fact that almost all of the time within almost all of the biological system, these thiol compounds will be keeping the SH-sensitive enzymes active. So the net effect of their presence is normally the maintenance of high enzyme activity.

That is not to say that the occasional formation of allicin is not beneficial.

There are times of stress when enzyme inhibition is called for and allicin is especially beneficial for this. In particular, its ability to preferentially oxidize thiols provides a mechanism for inhibiting enzymes in a nondestructive way, which can provide medicinal benefits (e.g. the inhibition of microbial replication). Because this inhibition is nondestructive (and normally temporary) and the original SH configuration can be easily restored, there is minimal toxicity to the host.

7.3 More about Antioxidants

The conventional view of reactions involving oxidants and antioxidants emphasizes the role of electron transfer, with the driving force being the difference in the oxidation/reduction (redox) potentials of the reactants. In some cases, an attempt has been made to relate the redox potentials of other types of reactions to that of electron transfer reactions. However, it is important to note that there is no single "redox state of a person" or even a "redox state of a cell" but rather there coexist a number of different redox couples, the redox states of which are not necessarily linked to each other (RB170.O96:285). Even if an overall equilibrium state could be predicted from the relative oxidation/reduction potentials of the various reactants, biological subsystems are rarely in equilibrium. (True equilibrium is achieved only in death, and perhaps not even then.)

7.3.1 Thiol Transfer

The transfer of a thiolate group that occurs during a thiol-disulfide exchange reaction is directly analogous to the transfer of an electron that occurs during an oxidation-reduction reaction. Just as the oxidation/reduction potential determines the equilibrium state associated with electron transfer reactions, an analogous oxidation/reduction potential for a thiol-disulfide couple can determine the equilibrium state for their thiol transfer reactions (absent other effects, such as steric restrictions) (EJB2:327).

The present inventor notes that within an organism, the majority of thiolate groups are either a cysteine, a cysteinal residue on a peptide (e.g. glutathione), a cysteinal residue on a protein, or some other thiolate group (e.g. an allyl mercapto group) with behavior in exchange reactions that is similar to that of cysteine. Therefore, to a first order, the equilibrium result of exchange reactions is a nearly uniform distribution of thiols and mixed disulfides. (Note that although the rate of an exchange reaction depends on the pKa of the thiol and the local pH, this rate only affects the rate at which equilibrium is approached, not the final equilibrium point.)

Researchers have found it useful to define for the entire set of thiol <—> disulfide redox pairs within an environment a redox status (REDST) with its formula being the square of the total thiol concentration divided by the total disulfide concentration. (The squaring of the thiol concentration is due to each disulfide being formed from two thiol molecules, and how this effects the dynamics of the reaction rate.) In humans, the REDST declines with age by approximately a factor of 4 between the third and the ninth decade of life (AEMB543:191) and is a major indicator of the status of biological aging.

The utility of the REDST concept comes in part from the distribution of thiol and disulfide concentrations naturally becoming equilibrated within an environment through the action of thiol-disulfide exchange reactions. In other words, although the total concentration of thiols and the total concentration of disulfides is not changed by an exchange reaction, the probability of any thiolate group (e.g. a regulatory cysteine residue in an enzyme) being part of a mixed disulfide (i.e. being "blocked") is a shared property within an environment, and any change in REDST (e.g. from the addition of an oxidant) shifts this probability for every such thiolate group. Thus, the manipulation of the REDST is a potential mechanism to broadcast a control signal within an environment, analogous to the use of hormones within an organism.

7.3.1.1 Common Confusion Associated with Various Types of Redox Potentials

But, in the opinion of the present inventor, the use the term "redox" for the potential associated with the thiol-disulfide couple has led to the confusion of many researchers. This confusion manifests itself, for example, in the extension of the general observation that the cellular environment is very "reductive" (which is true, in and of itself) to the common statement that this inhibits the formation of disulfide bonds in proteins within the cellular environment (which couldn't be less true).

Even the most recent textbooks commonly make statements such as: "The interiors of cells are for the most part reducing environments: they furnish electrons in the form of hydrogen atoms. . . . The chief effect of this (difference) is that cysteine residues in proteins are usually fully reduced to —SH groups inside the cell but are readily oxidized to disulfide S—S bridges when the protein is secreted" (QP551.P48:92, published in 2004).

Without further qualification, the term "reductive" is generally taken to refer to electron transfer reactions, and the cellular environment is certainly reductive in this sense. For example, the concentration of GSH, which will readily donate electrons, is typically in the range of 1-5 mM within cells (ARB52:711), while the concentration of intracellular oxidants will typically be less than 1% of this.

But thiol-disulfide reactions do not involve the reduced form of the thiol (e.g. GSH) but instead involve the ionized form (e.g. GS$^-$). So the relevant concentrations for evaluating how "reductive" the environment is, in the thiol-disulfide sense, is the concentration of the ionized form. For cysteine (and hence GSH) this is approximately of $\frac{1}{30}$ the concentration of the reduced form (at a pH of 7, given that the pKa of cysteine is approximately 8.5). For the specific case of glutathione within a cell, if the concentration of GSH is 1 mM, the concentration of GS$^-$ will be approximately 0.03 mm and the concentration of GSSG will be approximately 0.01 mM. (In other words, the concentrations of GS$^-$ and GSSG are in the same order-of-magnitude range.) It has been shown that these concentrations are in fact nearly optimum for the formation and maintenance of the correct disulfide bonds within proteins (BICH9__5015) and that even after the denaturation of a protein, it will spontaneously adopt the proper conformation (including the formation of disulfide bonds) when exposed to these glutathione concentrations, and without requiring the involvement of any enzymes. So, instead of being "fully reduced", the cysteine residues in the proteins within cells actively participate in disulfide bonds.

The process of the proper disulfide bond formation within a protein molecule illustrates that both the formation and dissolution of disulfide bonds are part of the process. Although an incorrect disulfide bond can easily form early in the process (e.g. between the wrong pair of cysteines), it will not be long lived, because it will tend to be under stress. If a thiolate ion drifts by, the thiol-disulfide exchange reaction will essentially always split this incorrect bridge (the separational pull will determine how the complex splits). However, once the proper conformation is achieved the disulfide bond will normally be under little stress and will not tend to be split by passing thiolate ions. This does not exclude there being multiple possible conformations for some properly functioning proteins, with each conformation possibly stabilized by disulfide bridges. In other words, "any protein disulfide bond that can be reduced by GSH . . . must be strained, or the protein conformation must change" (QP522.G58F85:205). Thus, even to the extent that the GS⁻ concentration produces a reductive environment (in the thiol transfer sense), it does not cause the reduction of properly folded proteins.

7.3.1.2 Antioxidant Effects of Thiol Transfer

In addition to forming bridges within a protein molecule (or a multi-polypeptide complex), disulfide bonds can provide structure and strength between proteins (and between other types of structural molecules within an organism). For example, hair and nails obtain their strength from richly interconnected disulfide bonds ("links") between proteins (e.g. keratins). Interestingly, the formation of a "permanent wave" involves the introduction of stress to hairs (by rolling them on curlers) then applying a reducing agent (to allow the stressed links to split), then the formation of new links conforming to the new hair curl (e.g. by oxidation from the surrounding air). A more medically relevant example is the hardening (and cracking) of skin that is associated with arsenic poisoning (keratoses, EHP112:1104) because the increased level of links in the skin keratins is probably due to the glutathione depletion that is associated with arsenic clearance from the body.

Disulfides are more oxidized than thiols and therefore the concentration of disulfides relative to thiols is higher in the more oxidative environment outside of cells than it is within cells. Thus, although extracellular antioxidants serve important functions, in some cases the dominant mechanisms are different from those within cells. This is especially true because most reactions within cells involve enzymes, but comparatively few extracellular reactions do (observation of the present inventor).

The ability of thiols to serve as reducing agents is well known, but, interestingly, disulfides can also serve to break intermolecular disulfide bonds that are under stress (with a thiol serving in a catalytic role), especially in the extracellular environment, as the following example illustrates. If an inter-protein disulfide bond is under stress (PS-SP in the equations below), a passing thiolate ion is likely to participate in a thiol-disulfide exchange reaction that will allow the stressed bond to separate. Although the thiolate has now become disulfide bonded to one side of the formerly stressed protein link, the other side has become an exposed thiolate ion on its protein. This thiolate ion will now tend to react with any passing disulfide molecule (e.g. ASSA in the equations below, representing diallyl disulfide, which is usually abbreviated as DADS). This exchange reaction will have the effect of leaving one half of the formerly passing disulfide attached to the former thiolate, and a new thiolate ion will be released to drift away. Hence, the net effect is that the original thiolate ion has been replace by a new thiolate ion, the former stressed link has become two blocked cysteines, and a formerly floating disulfide molecule has disappeared.

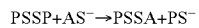
PSSP+AS⁻→PSSA+PS⁻

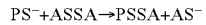
PS⁻+ASSA→PSSA+AS⁻

net: PSSP+ASSA→2 PSSA

The ability to increase the concentration of extracellular thiol and disulfide molecules (e.g. by providing AllylSH, DADS, and SAMC) is an important feature of the present invention, and it has now been illustrated how the extracellular disulfides contribute to the extracellular antioxidant activity, in addition to the extracellular thiols.

Note that although each individual thiol-disulfide exchange reaction has involved both an oxidation and a reduction, there is a net antioxidant effect (in terms of reversing the damage previously caused by oxygen exposure) because the stress that has been caused by the possibly inappropriate link between a pair of proteins has been replaced by a less stressful configuration. Given that there is some optimal level of inter-protein links in, for example, healthy skin, the maintenance of a level of thiols (and disulfides) comparable to that of a young person can maintain the extracellular environment closer to that of a young person.

The present inventor notes that cells themselves go through a life cycle, and that after cellular division, the newly formed cells are actually young, even in an old individual. Every new cell is the descendent of its parent, therefore all young cells are derived from old ones, with the ultimate parent having been perhaps a billion cellular generations ago. Therefore, to the extent that a cell can be considered young, this is due to it being the product of a recent division. Apart from the shortening of telomeres of differentiated cells (which has no significant effect until the telomeres are substantially shortened) these "young" cells in an "old" body express their "old" characteristics in response to signaling from their environment (e.g. the total thiol/disulfide concentration and the current REDST). Therefore, the parameters of the cellular environment of the typical young person can provide a target for the demonstrably safe and potentially therapeutically beneficial concentrations of thiols and disulfides to be achieved through the administration of *allium* related compounds to the host.

7.3.2 Coming Full Circle

The inhibitory effect of oxidized sulfhydryl groups on cellular reproduction was first explored well before allicin was discovered in the 1940's. This was extensively investigated, along with the corresponding growth promotional effects of thiols (which reduce sulfhydryl groups), in the 1920's and 30's and was shown to be a general property of cells. Experiments with plant root tips, paramecium, larvae, tumors transported into mice, and the severed legs of hermit crabs all showed that the administration of thiols (e.g. in the growth medium) significantly increased the growth (or healing) rate while the administration of an SH oxidant even more significantly inhibited growth (PPLAS13:261, PPLAS15:59). Modern experiments lead to similar results and conclusions (BBRC242:1) regarding both the growth and the death (by apoptosis) of cells and organisms.

These early observations, along with the new understanding of the actions of thiosulfinates, lead the present inventor to propose that a massively reductive change in the redox state within the cell is the primary intracellular signaling mechanism for the instigation of the multitude of actions involved with cellular division. Similarly, the converse change to a massively oxidative redox state is proposed to be the primary intracellular signaling mechanism for the instigation of apoptosis (the controlled dismantling of the cell during programmed cell death).

By administering either thiols or SH oxidants, the early experiments changed the probability of cellular division by a relatively small, but significant, amount. More recently, the amazing ability of allicin to oxidize the SH groups on enzymes has been shown to completely inhibit the growth of bacteria and other types of cells.

The present inventor proposes that this is a general property, and that essentially every type of cell will be found not to be able to divide in the presence of allicin (or similar thiosulfinates). The present invention provides a mechanism of delivering the precursors to allow said thiosulfinates to be locally formed as a result of the natural immune system response, while providing beneficial (and growth promoting) thiols to the rest of the organism the rest of the time.

8. EXAMPLES

Preparations of comestible or non-comestible formulations according to the invention may be made by a number of conventional methods. Nutritional wafers are within the scope of the invention. Compositions for oral dosage can include inactive components which provide for easier or more pleasant oral administration. Oral compositions may also include other active ingredients.

Methods of administration include non-oral means such as topical ointments, nasal, sublingual intravenous and parenteral or any other method that will present the active metabolites or their prodrugs to the cellular environment of a host. The host may be any type of animal with an immune system similar to that of a mammal.

8.1. Example 1

A Nutraceutical Beverage

Of the beverage formulations listed above, a favorite among the volunteer testers is the apple juice. This is prototypical for a wide variety of beverage formulations, as indicated in the list above.

First prepare a 1/400 dilution of allyl mercaptan by adding 1.25 ml (1/4 teaspoon) of food grade allyl mercaptan to 500 ml of distilled water.

Food grade allyl mercaptan is available from a variety of sources, including Penta International Corporation, Livingston N.J., USA. The cost for a 100 ml bottle is approximately $400 (which is less than 1.5 cents per serving). In practice, the production cost is dominated by the price of the apple juice. Kosher grade is also available, as an option.

Interestingly, laboratory grade allyl mercaptan is available from LabDepot, Inc. (www.labdepotinc.com) for only $107.94 per 100 ml, but for this use I decided to go with the food grade product (but not to pay extra for Kosher). Diallyl disulfide is also available from the same source, for $83.72 per 100 ml.

Upon adding the allyl mercaptan to the water, you may notice that that it initially floats on the surface because its solubility is only 1 in water (vs. 5 in ethanol) and its density, at 0.925, makes it lighter than water. But if left overnight at room temperature, it seems to uniformly distribute in solution, giving the liquid a slight milky color.

The best apple juice to use is one with minimal processing, but good results have been obtained with both filtered or unfiltered, and pasteurized or not. My preference is "Andronico's 100% Organic" from the local supermarket.

For the apple juice, add one half-teaspoon (2.5 ml) of 1/400 diluted allyl mercaptan to each 8 fluid ounces of beverage and let it sit overnight. Shake before using.

The theoretical maximum dosage (per 8 oz serving) is $1/400 \times 1$ g/ml$\times 0.925 \times 2.5$ ml$=5.75$ mg of allyl mercaptan. This is roughly the equivalent in "total thioallyl content" to 6.3 mg of allicin, because allicin yields 2 AllylSH per molecule, and the ratio of their formula weights is 2.19 (162.26/74.13).

This is a reasonable dosage because human consumption is typically 10 mg/day among Americans who eat fresh garlic (a 5-gram clove a day). However, it would be unreasonable to have a dosage significantly above this, because a person could reasonably expect to be able to consume several glasses of the apple juice at one sitting. Although in the future it may be determined that a dosage beyond this is beneficial, the dosage provided in this example seems to the present inventor to be a good per-serving upper limit for nutraceutical use, for now.

8.2. Example 2

Dietary Supplement Capsules

Dietary supplement capsules were produced by mixing one cup (250 ml) of whey protein powder with one cup of 1/100 dilution allyl mercaptan in a blender for 30 seconds. Interestingly, even after this short interval, the resulting mixture smells as milk-like as it does garlic-like. The mixture is pored into a non-stick baking pan and a stainless steel screen is placed on top.

After drying is completed (a couple of days), a spice grinder is used to produce a powder which is then put into #1 size gelatin capsules using the "Cap-M-Quik" from CAP-M-Quik Corporation, Berry Creek Calif. The yield is 250 capsules.

The calculated dosage is $1/100 \times 1$ g/ml$\times 0.925 \times 250$ ml$\times 1/250 = 9.25$ mg of allyl mercaptan per capsule. This is roughly the theoretical equivalent in "total thioallyl content" to 10.1 mg of allicin, because allicin yields 2 AllylSH per molecule, and the ratio of their formula weights is 2.19 (162.26/74.13).

These are the capsules that I am currently taking, two a day (four during flu season). Several of the evaluation volunteers have also tried them (free of charge) for a year or more, and have typically reported that they either "didn't get sick this year" or "only got slightly sick once" with a cold or flu.

After having consumed these capsules (and the other experimental formulations of nutraceuticals and capsules described above) for two years, a medical check-up and laboratory report showed these changes from a similar checkup two years previous:

| Weight | 155 lbs | (was 175) |
|---|---|---|
| Blood Pressure | 140/80 | (was 150/80) |
| Pulse rate | 60 | (was 70) |
| Temperature | 97.6 | (was 98.6) |
| HDL Cholesterol | 60 mg/dL | (was 45) |
| LDL Cholesterol | 128 mg/dL | (was 152) |
| Triglycerides | 128 mg/dL | (was 290) |

Another change is that I can now focus my eyes at a short distance (my optometrist confirmed that I now have 20/20 vision at 12 inches), which I had lost the ability to do in my late-forties.

I should mention that, based on what I was learning, I also made the following dietary changes during this 2 year interval:

Stopped taking a 500 mg vitamin C capsule each day
Stopped taking a 200 iu vitamin E capsule each day
Changed from a high content vitamin pill to a lower content one (One-A-Day)
Doubled red meat consumption frequency to 2 meals a week.
Doubled fish consumption to 2 meals a week
Doubled chicken consumption to 4 meals a week
Increased consumption of soft cheeses (e.g. brie) to one meal a week Decreased consumption of soy and/or potatoes to less than once a week Changed from occasional Stouffers Vegetable Lasagna to Stouffers Meat Lasagna Reduced consumption of fruits and vegetables somewhat (compensation for meat)

Increased consumption of avocados to almost one a week

Reduced alcohol consumption from 2 glasses of wine/day to 1 glass (sometimes 2)

Previously, I had thought that my "semi-vegetarian", low saturated fat diet was healthy, but I changed to a "low-meat" higher protein quality diet.

These results, although they have not yet been confirmed by a larger trial, are the main reason why I think that the current dosages are appropriate, even though the "allicin bioequivalence" test results show a lower than expected response.

8.3. Increased Dosage of Dietary Supplement Capsules

For a month I consumed 20 of the dietary capsules per day (roughly the theoretical equivalent in "total thioallyl content" to 200 mg of allicin). There were no undesirable side effects observed.

The two observed effects were an increase in taste sensitivity (some "hot" foods that I enjoy had become "too hot"), and a decrease in fatigue from exercise.

This is a case where it was appropriate for me to do the experiment myself, given that very few people have ever consumed the equivalent of 20 cloves of raw garlic per day.

9. USE OF OTHER *ALLIUM* RELATED ORGANOSULFUR COMPOUNDS

The present invention has been illustrated according to the use of the allyl mercaptan to produce protein-bound SAMC, and its subsequent conversion in vivo to other organosulfur compounds such as the thiol allyl mercaptan and the thiosulfinate allicin. But other thiosulfinates incorporating other types of mercapto radicals have also been shown to have similar biological properties.

For example, the thiosulfinates from onion tend to contain propyls instead of allyls. Just as the compound diallyl disulfide can be oxygenated to allicin, the onion derived compounds di-n-propyl disulfide and n-propyl allyl disulfide can be oxygenated to their corresponding thiosulfinates, which may explain their antibiotic effectiveness against *Salmonella typhimurium* and *E. coli* (AM17:903).

Similarly, the organosulfur compounds derived from cabbage tend to contain methyl groups, with methyl methanethiosulfinate the thiosulfinate $CH_2S(O)SCH_3$, corresponding to oxygenated $CH_3SSCH_3$) showing remarkable antimicrobial properties (JFP60:67).

A survey of the nematicidal activity of various sulfur compounds from *Allium grayi* Regel and *Allium fistulosum* L. var. *caespiitosum* concluded that those which have a disulfide, trisulfide, thiosulfinate, or thiosulfonate group are potential nematicides and antimicrobials (ABC52:2383). The most effective compound found was dipropylthiosulfinate $CH_3CH_2CH_2S-S(O)CH_2CH_2CH_3$.

In general, it is expected that mercapto radicals containing up to 5 carbon atoms in a linear or branched configuration, when disulfide bounded to cysteine, will share many of the properties that are attributed to SAMC (and its derivatives) in this description. Therefore, these constitute alternative substances that may be disulfide bounded to protein-bound cysteine for administration to hosts for digestion. Studies of radioprotective substances have shown that thiol compounds with more than 5 carbon atoms are ineffective in protecting animals from radiation exposure. The explanation advanced here is that when thiols that are larger than this are consumed, they eventually form mixed disulfides with glutathione which are excreted from cells via the GS-X Pump (QP606.G59G59: 199). Therefore, the limit to the size of the mercapto group being administered is ultimately limited by whether it activates the GS-X pump when conjugated with glutathione, which is currently estimated by the inventor as corresponding to a limit of 5 carbon atoms.

The requirement of the present invention for the *allium* related compound to be able to metabolize into a thiol and a thiosulfinate or mixed thiosulfinate can be satisfied by a variety of organosulfur compounds in various compositions. SAMC has the advantage that is a known derivative of garlic that has been successfully consumed by millions of people. And SAMC related organosulfur compounds (such as allicin) have been extensively investigated. But the present invention is intended to also apply to the more general class of compounds that have been presented in this section.

10. FURTHER COMPARISON WITH THE PRIOR ART

The applicability of prior art can be evaluated in two contexts. Prior art involving compounds with similar molecular structures can be distinguished from the present invention by criteria such as the new medicinal applications of these compounds that are taught herein, the method of administration, and the dosage range. Conversely, prior art involving similar medicinal applications can be distinguished from the novel compounds that are taught herein, their methods of administration, and their dosage ranges. In other words, the present invention involves both new ways to use old compounds and new compounds to use for old medicinal applications, as can be seen from the following consideration of prior art.

10.1 A Method for Removing the Smell of Alliums from Foodstuffs.

Some research has been published on techniques for removing the smell of *allium*-specific volatile sulfur compounds from foods (JAFC50:3856). The research concentrated on identifying foods that could "capture" the volatile compounds, and a wide variety of types of foods were tested, with prune, burdock, basil, eggplant, and mushroom being shown by gas chromatography to be able to capture 100% of the odorous compounds.

Further investigation of the mechanism of capture by phenolic compounds (e.g. those in mushrooms) indicated that the addition of thiols to phenolic compounds is catalyzed by enzymes present in raw foods (they term this "enzymatic deodorization"). They further determined that disulfides could be degraded by heating and propose that the degradation products could also be removed by performing an enzymatic addition reaction to o-quinone after heating. The third mechanism of capture that they describe is the affinity to molecules either due to hydrophobicity or by the trapping by porous polymers present in foods.

This prior art is not applicable to the present invention because no attempt was made to preserve the medicinal properties of the volatile sulfur compounds, or to even establish the nutritional qualities of the resulting food products. In fact, no organosulfur compounds are being added to the food at all, instead they are removing the odors of the existing compounds in the food, possibly by adding other foodstuffs. The authors did not consider the desirability (or even possibility) of preserving the integrity of the organosulfur groups while eliminating their volatility via disulfide bonds (the preferred method taught by the present invention). The method they taught (covalent bonding to phenols) does not produce a compound that would be expected to metabolize to thiols, thiosulfinates, or mixed thiosulfinates.

10.2 Treatment of Proteins for Food Quality Improvement

Treatment with SH-containing sulfur amino acids has been shown to be able to prevent food browning or to improve the protein quality by increasing the cyst(e)ine content. For example, the browning of cut surfaces of apples can be completely prevented by soaking them in a 5 mM solution of cysteine for 6 hours (R850.A1A3V289:171). Presumably, some of these amino acids remain bound to the food after treatment, but amino acids per se are not among the *allium*-related compounds that are subject to the present invention.

10.3 Prior Art Drugs 10.3.1 Radioprotective Drugs

Various thiols and disulfides (along with various other chemical substances) have been studied for their radioprotective properties (RR2:392). Most sulfhydryl compounds tested were inactive, but the amino acids cysteine, homocysteine, cysteamine, and the peptide glutathione (along with their disulfides) have been found to be effective.

Their experimental use has shown that their effectiveness is limited to a protection of about 2 to 1 (e.g. the response to radiation is cut in half) and in order to achieve this level of protection a massive dose is administered within a few minutes before the radiation exposure.

Therefore, although these compounds relate generally to those utilized by the present invention (being thiols or disulfides that can be ingested), they are not in the form of protein-bound mercapto radicals when administered and thus go off in a different direction from the present invention.

10.3.2 Other Drugs that Metabolize to *Allium* Related Compounds

There are other drugs that metabolize to thiols or disulfides that are not in the form of bound mercapto radicals when administered. For example, the 1,3-thiazolidine ring system has attracted considerable interest over the years in relation to its occurrence as the initial structural unit in a variety of biologically and pharmacologically relevant compounds (BBA1073:416).

A characteristic feature of the 1,3-thiazolidine ring system is its facility to hydrolytic cleavage, resulting in an opening of the ring and exposing an SH group (BBA1073:416).

In other words, a thiol is produced in vivo from a non-mercapto radical drug.

Another example is provided by the analysis of the metabolism of the lipid-lowering drug probucol (a molecule that contains sulfur, but not in the form of a disulfide), which is proposed to produce (as a side effect, in the opinion of the authors) the disulfide $CH_3SSCH_3$ during the breakdown of spiroquinone to diphenoquinone (their proposed active ingredient in a free radical scavenger cycle).

In other words, a disulfide is produced in vivo from a non-mercapto radical drug.

Because the form of administration is not in the form of a protein-bound mercapto radical, these examples of prior art are non-applicable to the present invention, although in some cases their medicinal applications may overlap.

10.5 Garlic Based Dietary Supplements

Of the existing "garlic" dietary supplements, none contain protein-bound mercapto radicals, and only one is claimed to contain SAMC.

10.5.1 Further Comparison with Aged Garlic Extract (AGE)

Previously, the only dietary supplement claiming SAMC content was Aged Garlic Extract™ from Kyolic Research. According to Kyolic Research "Aged Garlic Extract contains a unique sulfur-containing compound ... SAMC is produced only during aging and is not present in fresh raw garlic ... or in various garlic preparations". (www.kyolic.com/html/kre-search/Abstracts/samcinfo.htm on May 7, 2005)

The "AGE" product contains primarily the water-soluble compounds S-allylcysteine (SAC, 0.62 mg/g) and SAMC (0.14 mg/g), but it also contains lesser amounts of the lipid-soluble compounds diallyl sulfide, triallyl sulfide, and diallyl disulfide (DADS). AGE contains no allicin. The total amount of sulfur compounds is 2.14 mg/g (RM666.G15K6313, page 104). Therefore, SAMC is less than 10% of the total, and for a 100 mg capsule (for example), the SAMC content is only 0.014 mg.

An extensive review of the active components of garlic notes that SAC accounts for less than 3% of the biological activity of AGE (RM666.H33P49:176). Yet the AGE product is very successful, and has been shown in many studies to be beneficial, indicating that its concentration of various sulfur compounds (which include SAMC) is sufficient to be beneficial.

The present invention anticipates that daily dosages may be found to be beneficial even up to, say, 100 mg of SAMC, which is over a thousand times the dosage available in AGE capsules. Even at 100 mg per day, the dosage is much lower than the dosage that has been used successfully in some experiments involving animals, so even higher dosages are anticipated for specific treatments. For example, in a study of the prevention of acetaminophen poisoning in mice (PHYRES3:50), the dosage of SAMC used was up to 200 mg/kg, which would correspond to a dosage of 14,000 mg for a 70 kg adult human. The low toxicity of SAMC allows dosages within this range to be utilized, when necessary (although obviously not within a single capsule!).

Considering that the 14 micrograms of SAMC in a typical AGE capsule corresponds to only 0.2 micrograms per kilogram in a 70 kg adult, it can be seen that there is over six orders of magnitude of additional range available for tailoring the SAMC content to the needs of the product, from nutraceutical to drug.

In a comparison of various of garlic supplements (JN131:955S, written by employees of the manufacturer of AGE), it is proposed that SAC be used as standard for comparison due to its bioavailability. However, the metabolism of SAC appears to be fundamentally different from that of other *allium* related compounds (as indicated by the lack of breath AMS or acetone, see section 4.2.5). The relatively easy detection of SAC itself (e.g. in plasma, PM60:214 FIG. 1) after consumption is due to its lack of rapid disappearance (as opposed to the other compounds, see section 4.2.5). The main elimination pathway for SAC is the formation of N-acetyl-SAC by acetyl-transferase (probably a first pass effect), which is then excreted in urine (PM60:214). In other words, it appears that it is actually the lack of significant metabolism of SAC that accounts for its purported "bioavailability".

10.5.1.1 SAC Vs. SAMC

Chemical Structure of SAC:

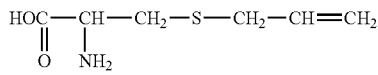

Chemical Structure of SAMC:

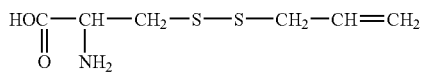

SAC contains a cysteinyl radical bonded to an allyl group, with just one sulfur atom in the molecule. In contrast, SAMC contains a cysteinyl radical bonded to an allyl-mercapto radical, resulting in two sulfur atoms in the molecule (bonded together by a disulfide bond). Therefore SAMC can participate in disulfide exchange reactions, but SAC cannot. Also, via either reduction or thiol-disulfide exchange reactions, an SAMC molecule can ultimately yield both a cysteine molecule and an allyl mercaptan molecule. In general, experimental results have shown that SAMC has more beneficial medicinal properties than SAC does (which is to be expected, because both cysteine and allyl mercaptan have been shown to be beneficial).

But the present invention anticipates dosages on the order of 100 mg of SAMC per day, which is over a thousand times the dosage available in AGE capsules. Even at 100 mg per day, the dosage is much lower than the dosage that has been used successfully in some experiments involving animals. For example, in a study of the prevention of acetaminophen poisoning in mice (PHYRES3:50), the dosage of SAMC used was up to 200 mg/kg, which would correspond to a dosage of 14,000 mg for a 70 kg adult human. The low toxicity of SAMC allows dosages within this range to be utilized, when necessary (although obviously not within a single capsule!).

Considering that the 42 micrograms of SAMC in an AGE capsule corresponds to only 0.6 micrograms per kilogram in a 70 kg adult, it can be seen that there is over six orders of magnitude of additional range available for tailoring the SAMC content to the needs of the product, from nutraceutical to drug.

11. CONCLUDING REMARKS

It has been established by the inventor that bound mercapto groups (especially mixed disulfides) where the mercapto group is bound to a significantly larger molecule such that the mercapto group can be liberated metabolically have advantages over the administration of mercaptans themselves (which typically have a strong, unpleasant taste and smell) or thiosulfinates (which are overly reactive, typically have a short shelf life, and typically are toxic in moderate or large dosages). Therefore the teachings herein apply to any form of bound mercapto group that can metabolize to at least one type of thiol molecule and at least one type of thiosulfinate or mixed thiosulfinate molecule.

The model compound protein bound SAMC has the advantages that it metabolizes to allyl mercaptan and other known derivatives of garlic that have been successfully consumed by millions of people and also to cysteine, which can be deficient in diets. The cysteine itself (an amino acid) is part of the protein, and is not considered to be an added *allium* related mercapto group.

Another advantage of using an organosulfur compound that metabolizes to allyl mercaptan and its derivatives is that related organosulfur compounds (such as allicin) have been extensively investigated. The present invention, however, applies also to the more general class of compounds that have been presented in this section, which are referred to herein as "*allium*-related" organosulfur compounds.

Although the present invention neither teaches nor claims any of the natural sulfur-containing amino acids that are commonly found within mammals (e.g. methionine, cysteine, cystine, homocystine, cysteamine, etc.), considerable attention has been drawn to the important functions of the biothiol cysteine. This is in part to illustrate the properties that are common to biothiols, but it is also the expectation of the present inventor that to the extent that any of these shared effects are regulated (e.g. the level of antioxidants), the increase in thiols provided by the application of the present invention can "spare" some of the cysteine in the body so that it becomes available for other purposes. For example, this may lead to the increased biosynthesis of taurine, without requiring a corresponding increase in dietary cysteine.

More detailed information about the antimicrobial properties, and prevention of damage to the host from the host's immune response to infection is contained in my co-pending U.S. application Ser. No. 10/853,415 entitled "Organosulfur Prodrugs for the Prevention and Treatment of Infectious Diseases and Pathologic Immune System Response" filed May 24, 2004.

More detailed information about various other applications related to the present invention is contained in the US patent application "Personal Care and Medicinal Applications of Products Incorporating Bound Organosulfur Groups" contemporaneously filed herewith by the present inventor.

The present invention has been illustrated primarily according to its application as a nutraceutical or drug with antioxidant, oxidant, antitoxic, and antimicrobial properties, but given the benefit of this disclosure those skilled in the art will realize that it can also be applied to other conditions, such as cardiovascular disease. Therefore, the invention is not to be limited to the above description and illustrations, but is defined by the appended claims.

What is claimed is:

1. A method of providing a recycling extracellular antioxidant whose locality includes both the intracellular and extracellular environments to a mammalian animal in need thereof, said method comprising:
    administering to said mammalian animal a therapeutically effective amount of a composition comprising molecules selected from the group consisting of mercaptans, mixed disulfides formed from mercaptans disulfide bonded to proteins, or a mixture thereof, wherein within said mammalian animal, said composition:
    (a) metabolizes via digestion or thiol-disulfide exchange reactions to form membrane permeable mercaptans that are organic molecules each comprising a sulfur atom and up to 5 carbon atoms in a linear or branched configuration and having a molecular weight of 350 Daltons or less;
        wherein said membrane permeable mercaptans are permeable to cells of said mammalian animal;
        wherein said membrane permeable mercaptans comprise said extracellular antioxidant within said mammalian animal, becoming concurrently oxidized to form disulfides or mixed disulfides;
    (b) wherein said disulfides or mixed disulfides form membrane permeable disulfides or mixed disulfides that enter cells of said mammalian animal;
        wherein said membrane permeable disulfides or mixed disulfides are reduced within the cell to produce said membrane permeable mercaptans of (a);
    thereby providing a recycling extracellular antioxidant whose locality includes both the intracellular and extracellular environments within said mammalian animal.

2. The method of claim 1 where said recycling extracellular antioxidant increases the ratio of the extracellular thiol concentration to the sum of the extracellular disulfide and mixed disulfide concentrations,
    whereby a more reduced extracellular redox status is produced within said mammalian animal.

3. The method of claim 2 where said mammalian animal is a human of age 40 or older and where said more reduced extracellular redox status is equal to or greater than the extracellular redox status of said human was at age 35.

4. The method of claim 1 where said composition comprises:
mercapto groups substantially bound to protein molecules that contain cysteine residues;
where the substantial binding of said mercapto groups to said protein molecules comprises mixed disulfide bonds formed between said mercapto groups and said cysteine residues of said protein molecules.

5. The method of claim 1 where said disulfides or mixed disulfides become further oxidized by reactive oxygen species emitted from immune system cells to form thiosulfinates or mixed thiosulfinates.

6. The method of claim 5 where said thiosulfinates or mixed thiosulfinates are antimicrobial.

7. The method of claim 5 where said thiosulfinates or mixed thiosulfinates inhibit the proliferation of tumor cells.

8. The method of claim 4 where the method of administration is oral administration and said composition is substantially free of thiosulfinates and remains substantially free of thiosulfinate formation during digestion.

9. The method of claim 1 where said membrane permeable mercaptans comprise mercapto radicals that are found in human foods.

10. The method of claim 9 where said membrane permeable mercaptans are allyl mercaptan, methyl mercaptan, propyl mercaptan, or a mixture thereof.

11. The method of claim 2 where said mammalian animal is a human of age 50 or older and where the increase in the ratio of the extracellular thiol concentration to the sum of the extracellular disulfide and mixed disulfide concentrations produces a softening of the lenses of the eyes such that the ability to focus the eyes at a distance of 12 inches becomes equal to or greater than said ability to focus the eyes at said distance when said human was at age 40.

12. The method of claim 2 where said mammalian animal is a human of age 50 or older and where the increase in the ratio of the extracellular thiol concentration to the sum of the extracellular disulfide and mixed disulfide concentrations produces a reduction in body weight such that the resulting body weight is less than or equal to the body weight of said human when said human was at age 40.

* * * * *